United States Patent
Sauer et al.

(10) Patent No.: US 7,211,093 B2
(45) Date of Patent: May 1, 2007

(54) SEW-RIGHT RUNNING STITCH INSTRUMENT

(75) Inventors: Jude S. Sauer, Rochester, NY (US); John F. Hammond, Canandaigua, NY (US); James W. Guelzow, Victor, NY (US); Michael W. Fitzsimmons, Rochester, NY (US); Mark A. Bovard, Mendon, NY (US)

(73) Assignee: LSI Solutions, Inc., Victor, NY (US)

( * ) Notice: Subject to any disclaimer, the term of this patent is extended or adjusted under 35 U.S.C. 154(b) by 609 days.

(21) Appl. No.: 10/757,042

(22) Filed: Jan. 14, 2004

(65) Prior Publication Data

US 2005/0154402 A1    Jul. 14, 2005

(51) Int. Cl.
*A61B 17/04* (2006.01)
*A61B 17/12* (2006.01)

(52) U.S. Cl. .................. 606/144; 606/145; 606/148

(58) Field of Classification Search ............. 606/144, 606/145, 148; 112/169
See application file for complete search history.

(56) References Cited

U.S. PATENT DOCUMENTS

| | | |
|---|---|---|
| 5,431,666 A | 7/1995 | Sauer et al. |
| 5,520,702 A | 5/1996 | Sauer et al. |
| 5,643,289 A | 7/1997 | Sauer et al. |
| 5,669,917 A | 9/1997 | Sauer et al. |
| 5,766,183 A | 6/1998 | Sauer |
| 6,533,796 B1 | 3/2003 | Sauer et al. |
| 2002/0107530 A1 | 8/2002 | Sauer et al. |

*Primary Examiner*—Anhtuan T. Nguyen
*Assistant Examiner*—Timothy Neal
(74) *Attorney, Agent, or Firm*—Stephen B. Salai, Esq.; Brian B. Shaw, Esq.; Harter Secrest & Emery LLP

(57) ABSTRACT

An instrument and method for suturing wound closures is provided having a handle, shaft and suture engagement mechanism. The instrument provides for multiple placements or "bites" of suture in tissues to enable a wide variety of suturing techniques, including the ability to "run" a suture. The instrument further facilitates suture knot tying. The method of this instrument provides for rapid and effective remote suture placement and knot tying.

45 Claims, 53 Drawing Sheets

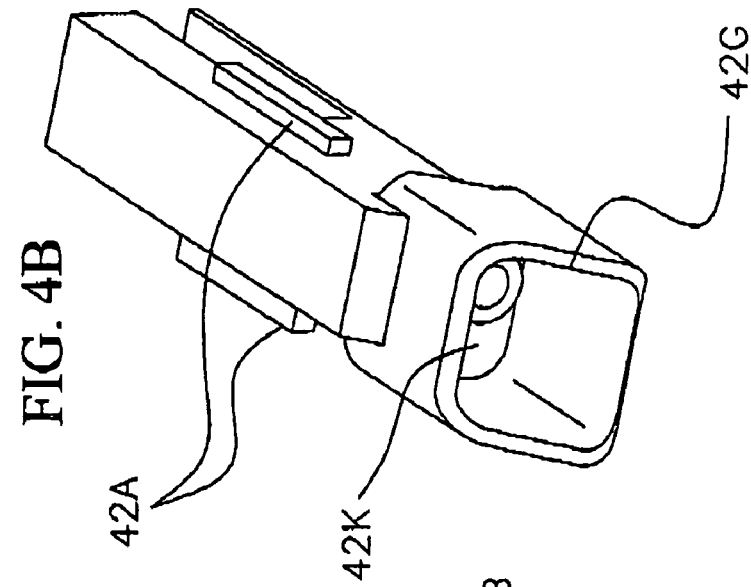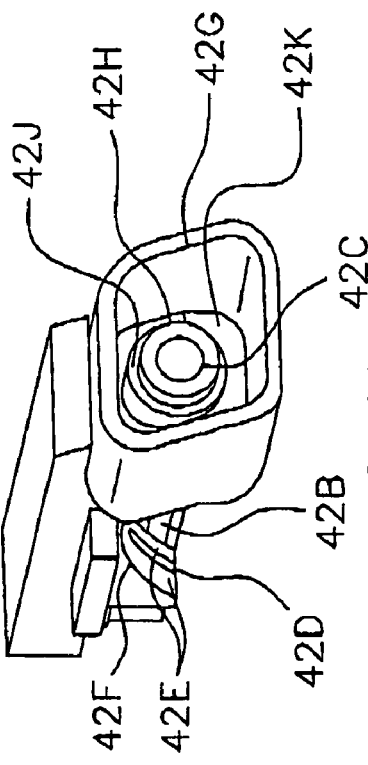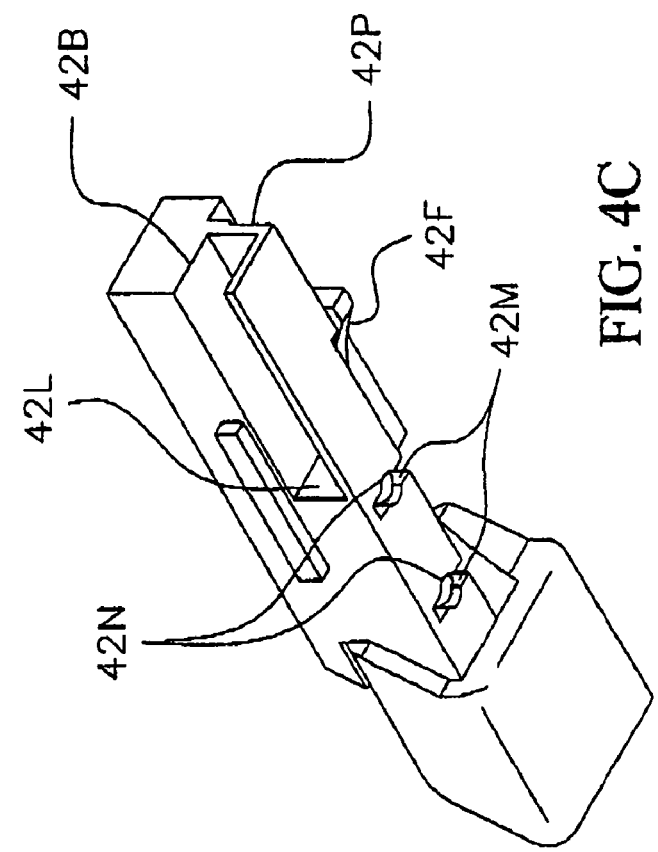

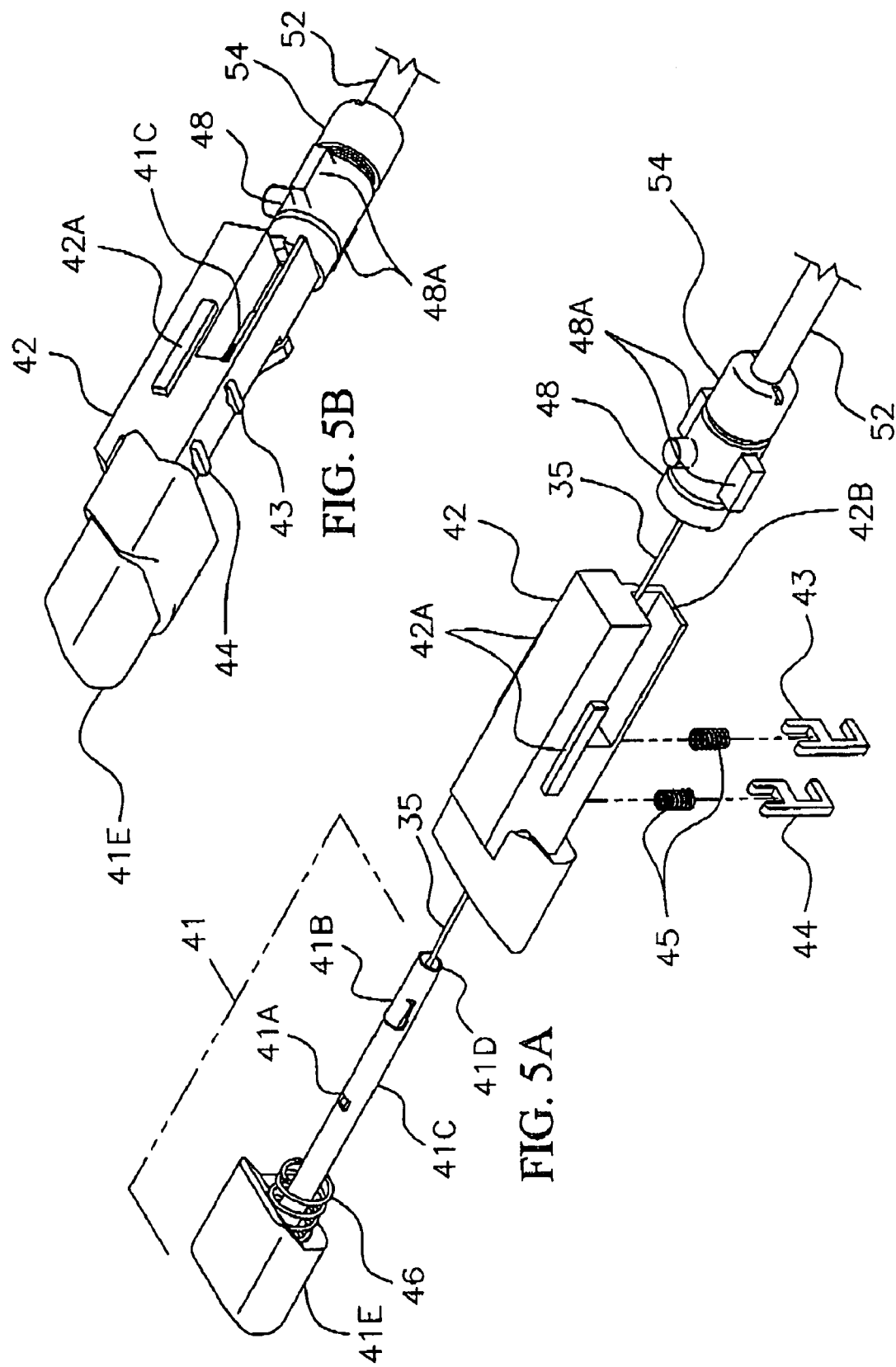

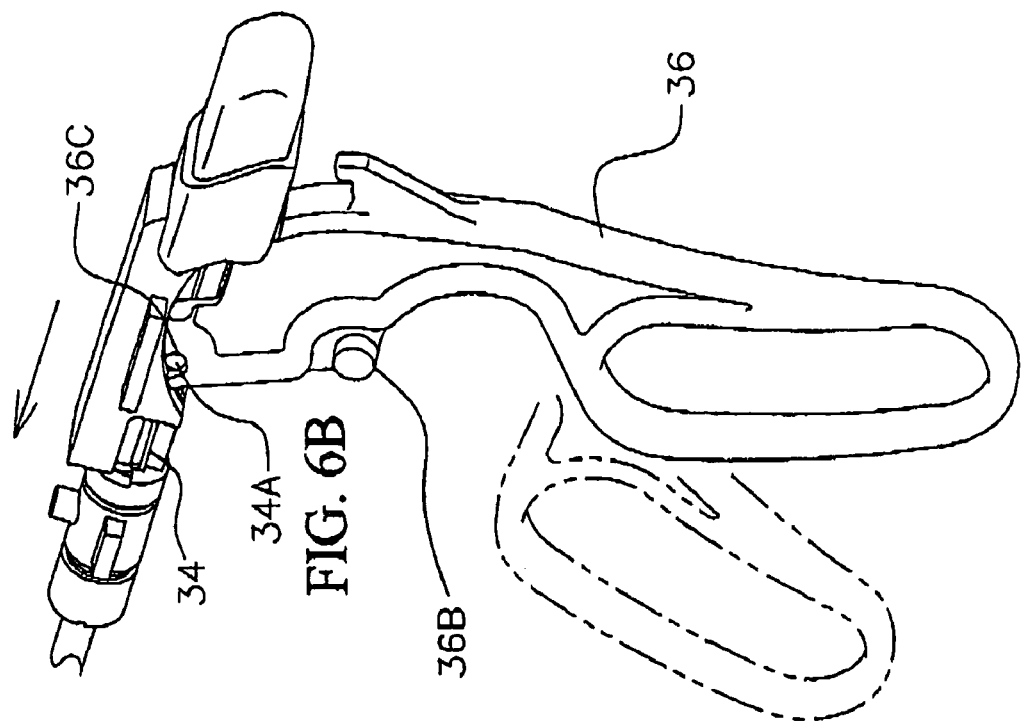
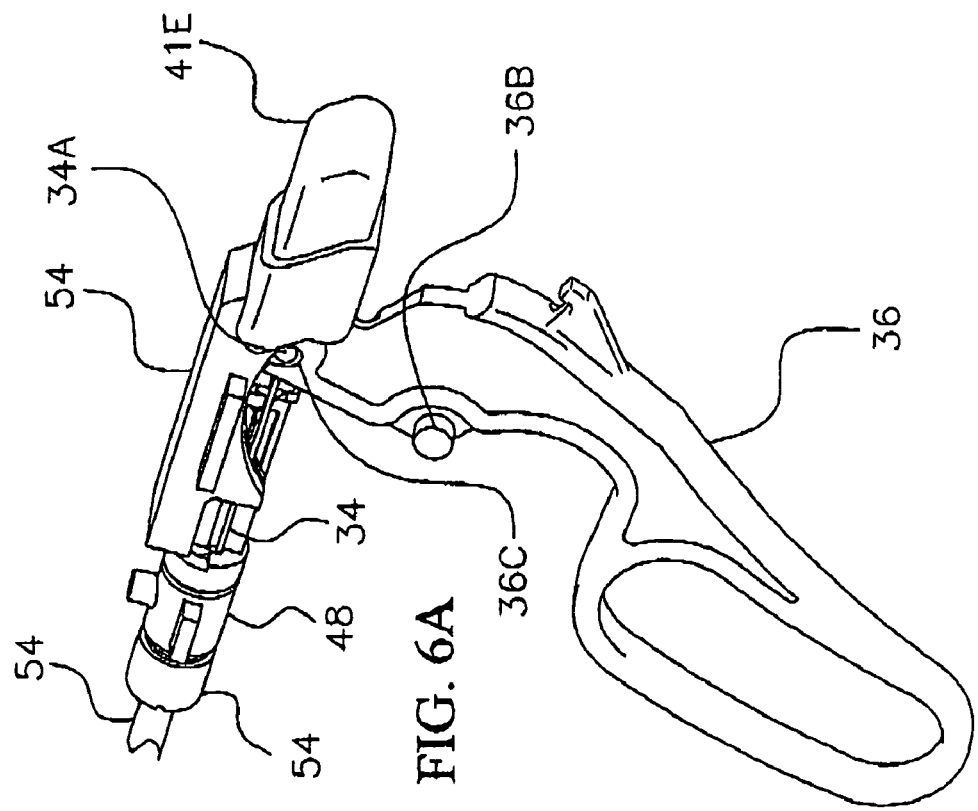
FIG. 6A
FIG. 6B

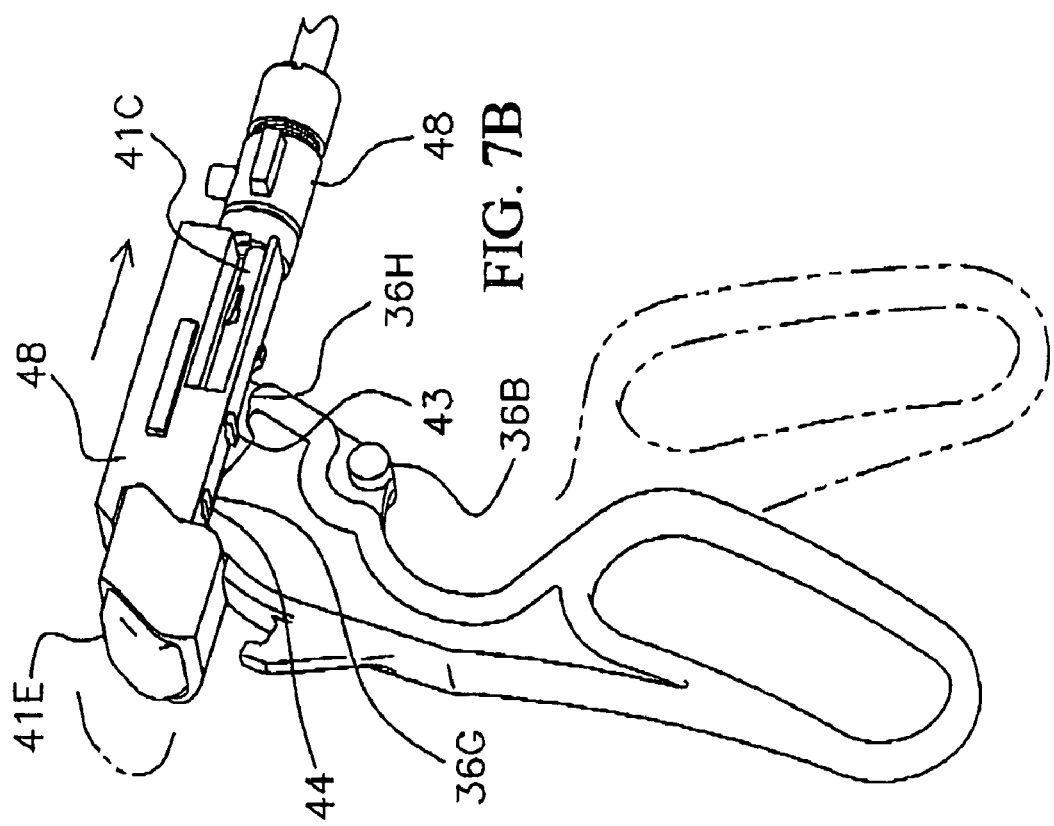
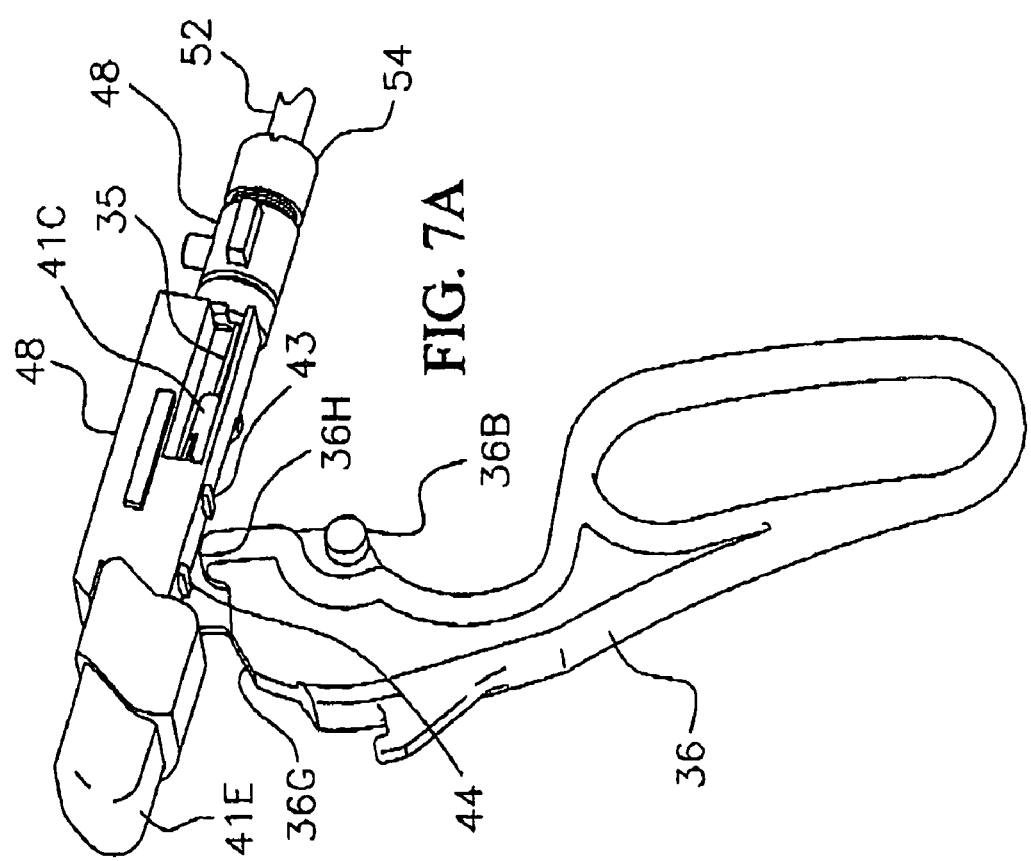

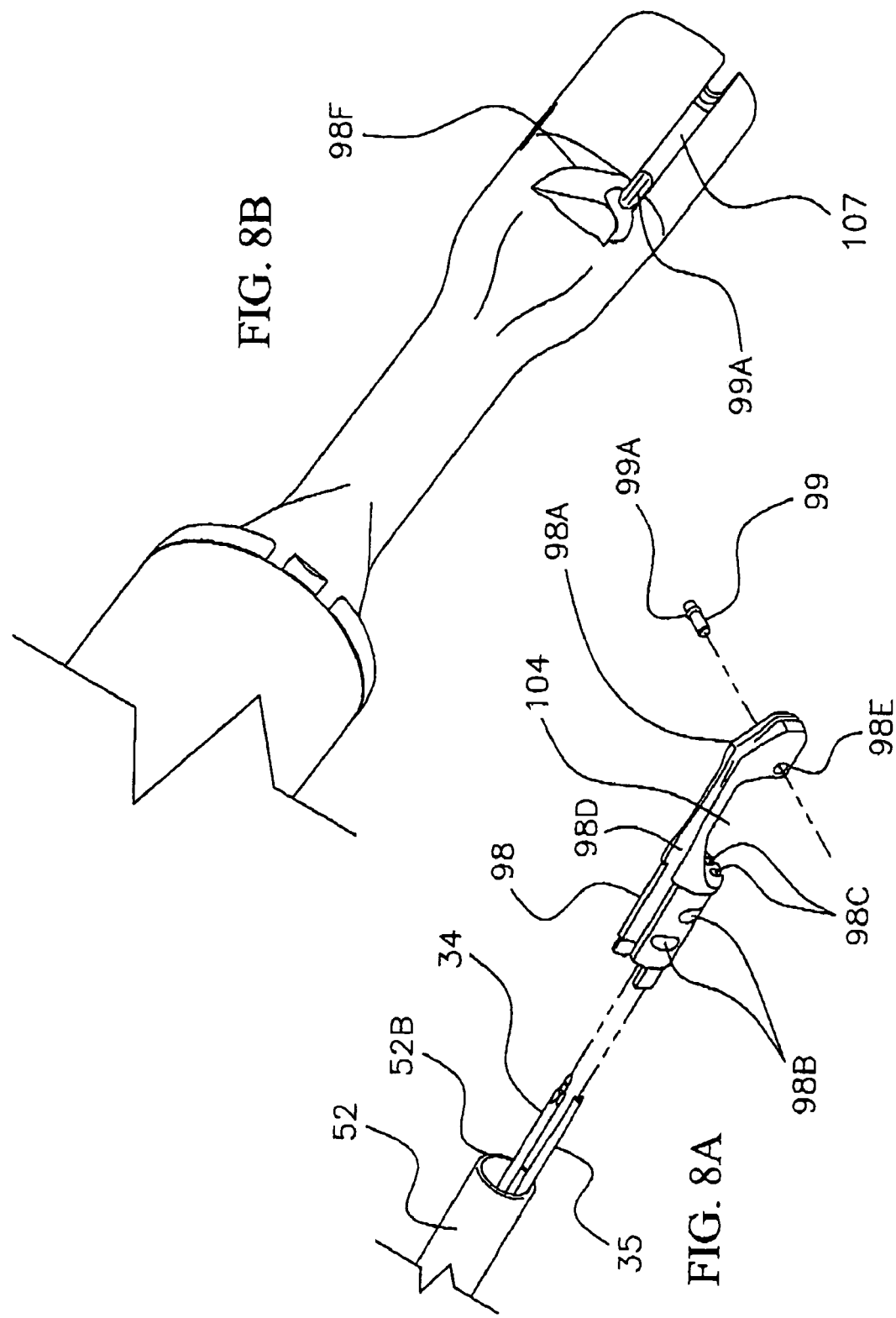

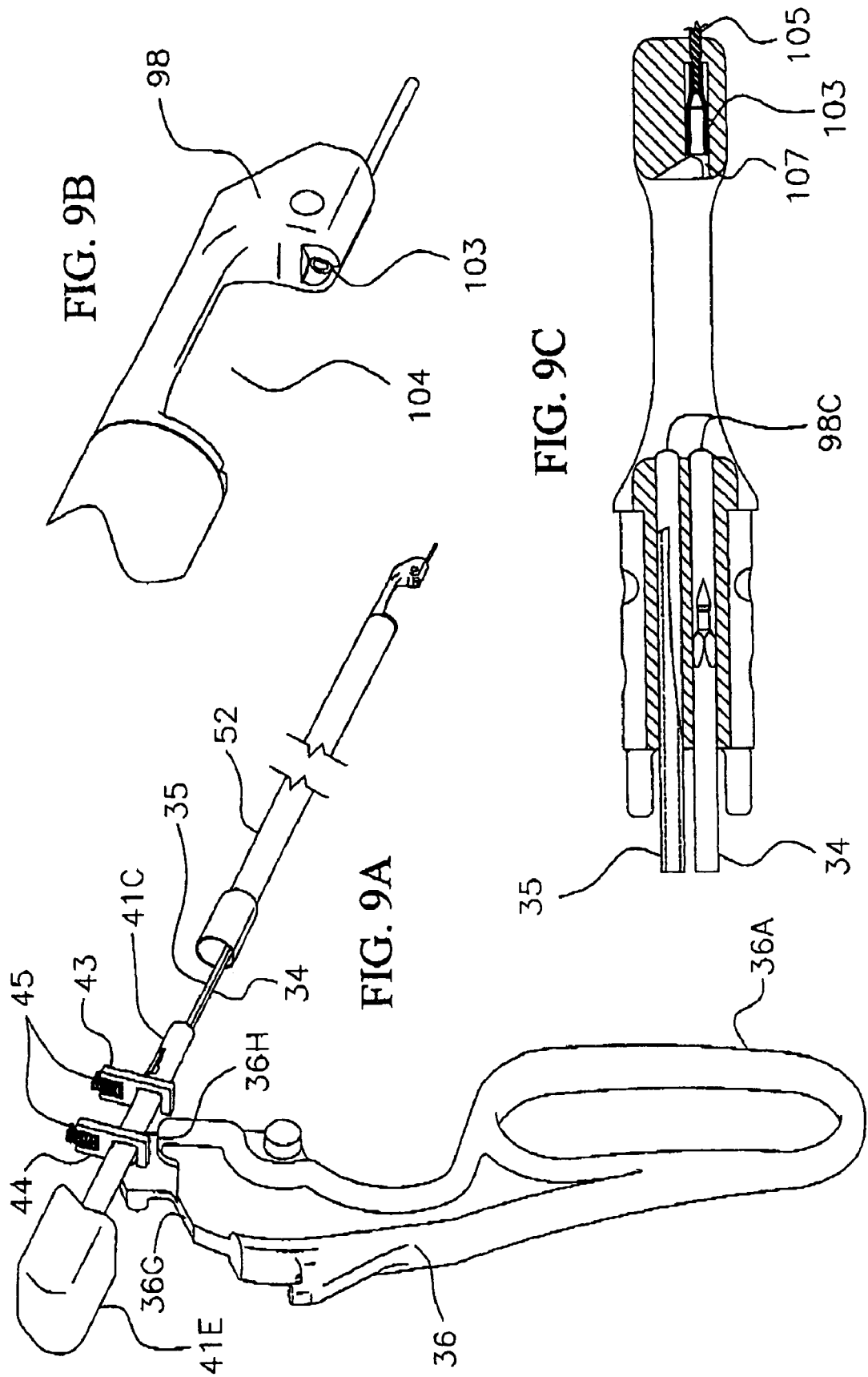

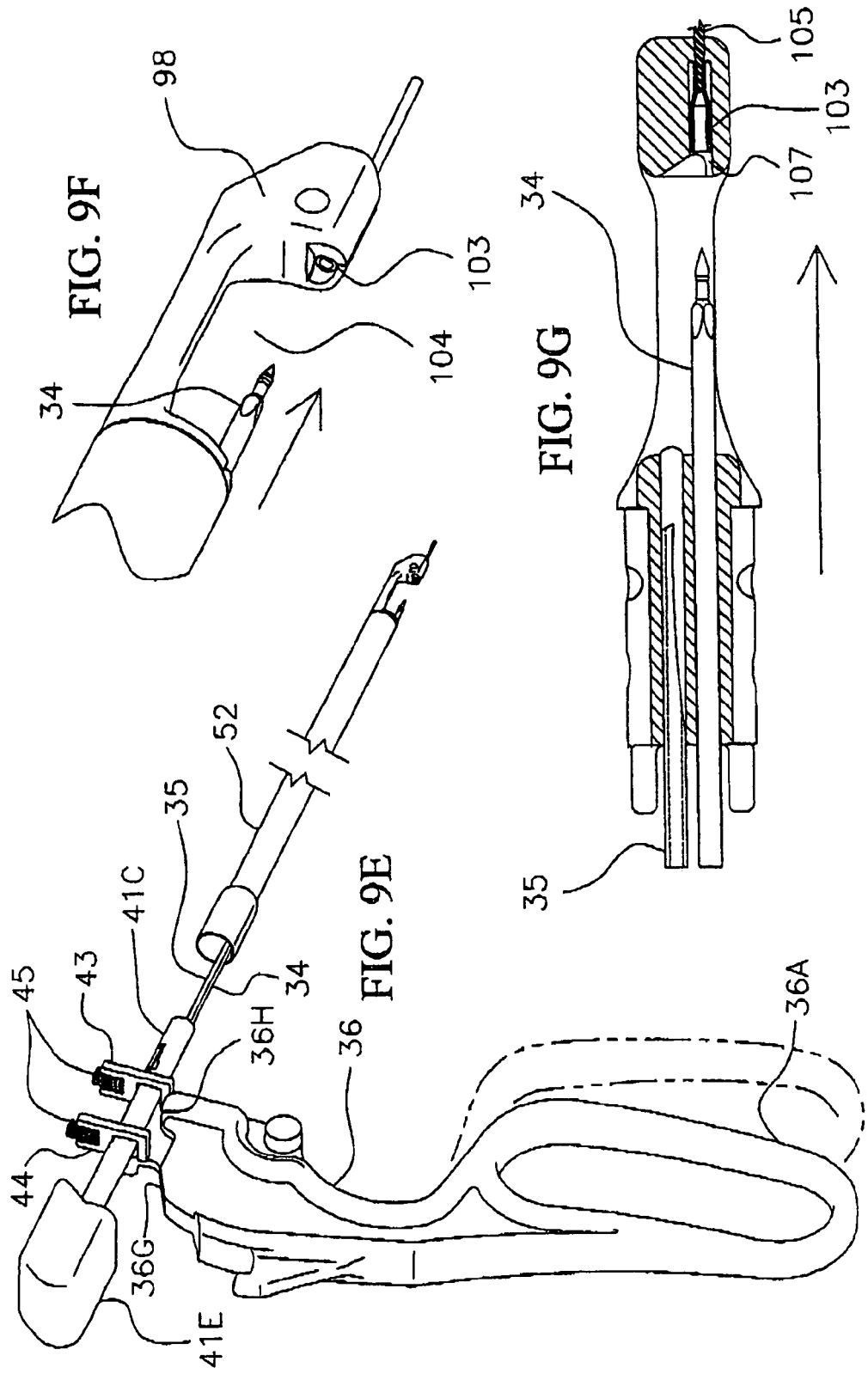

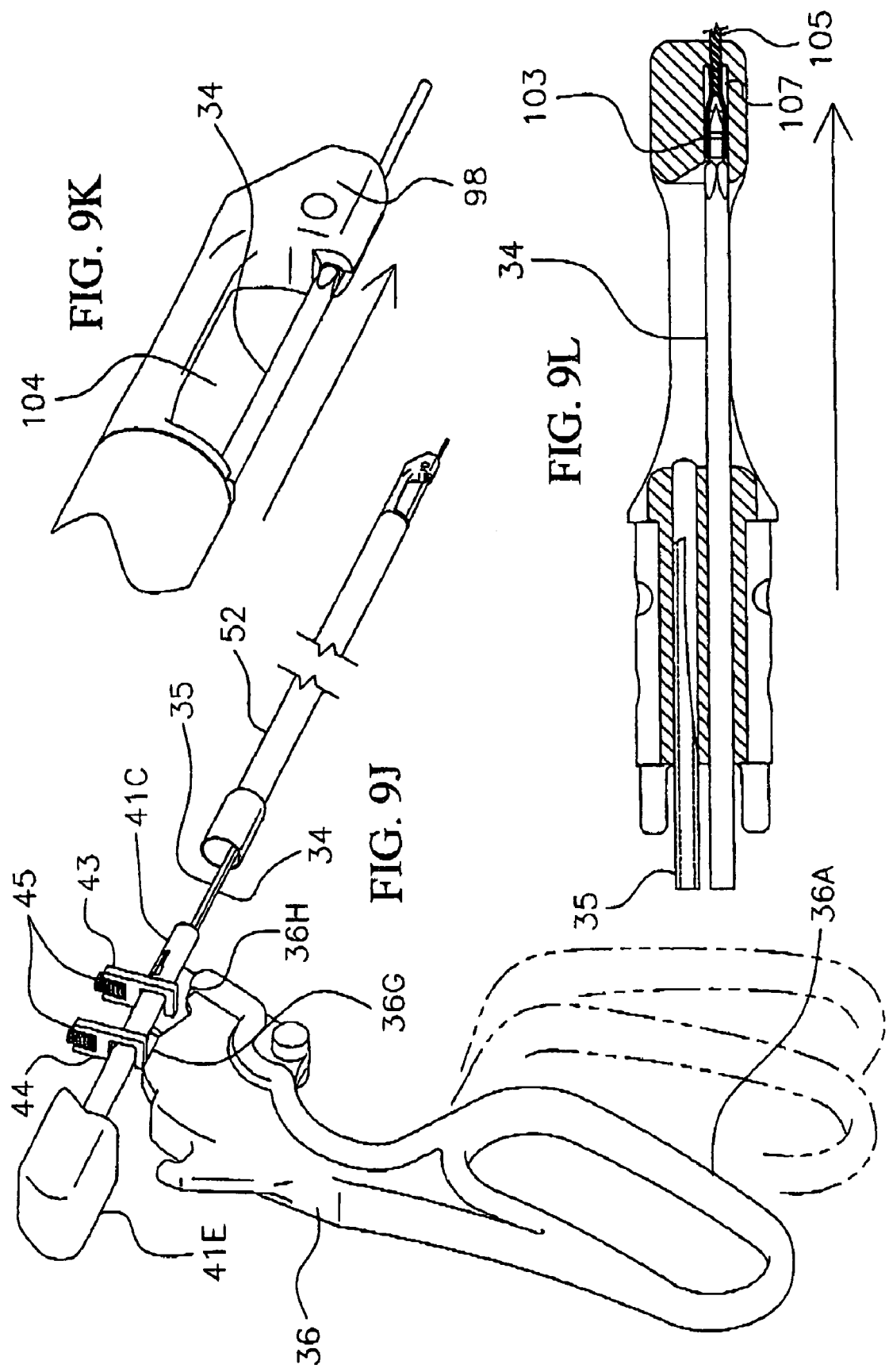

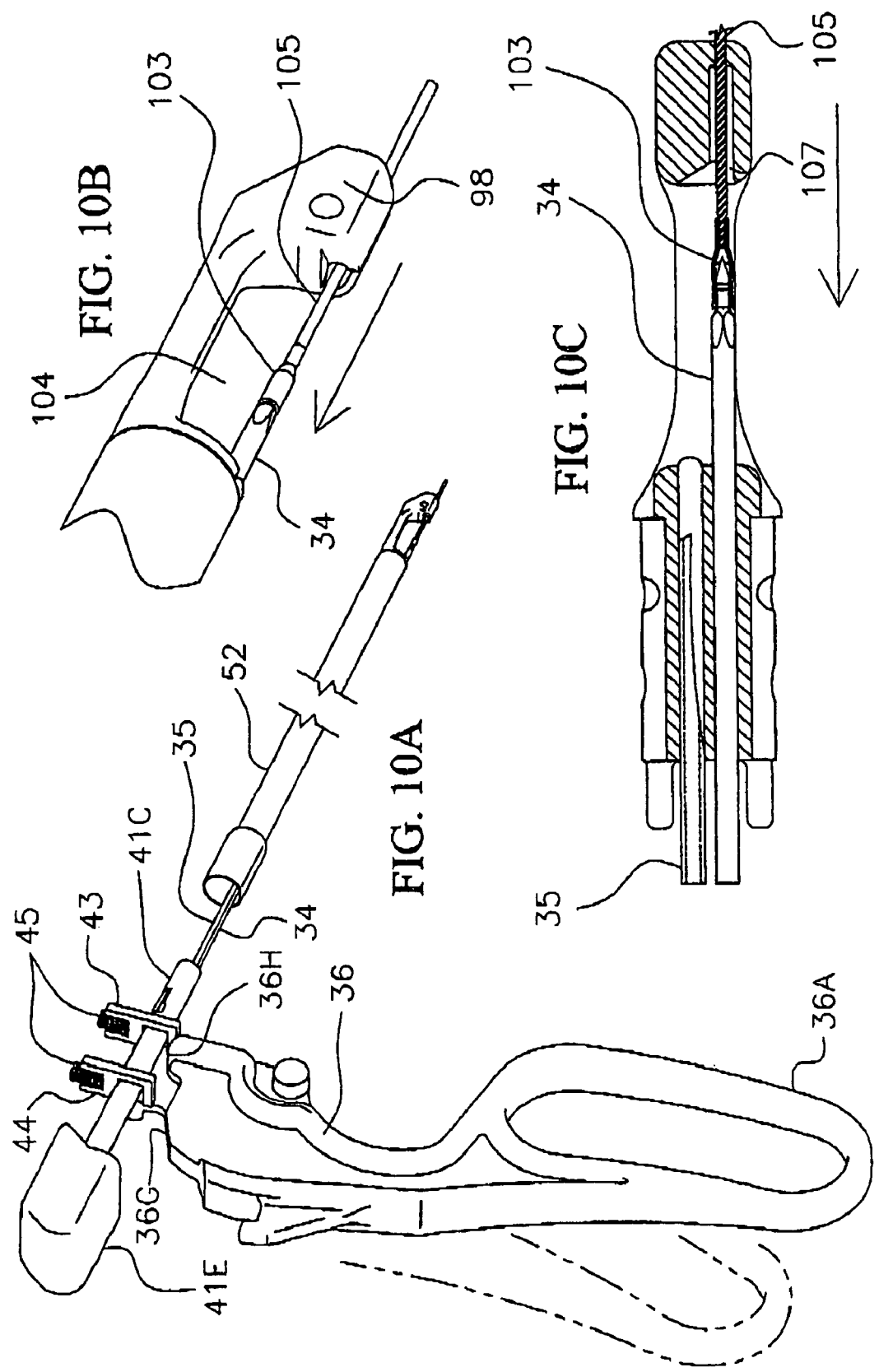

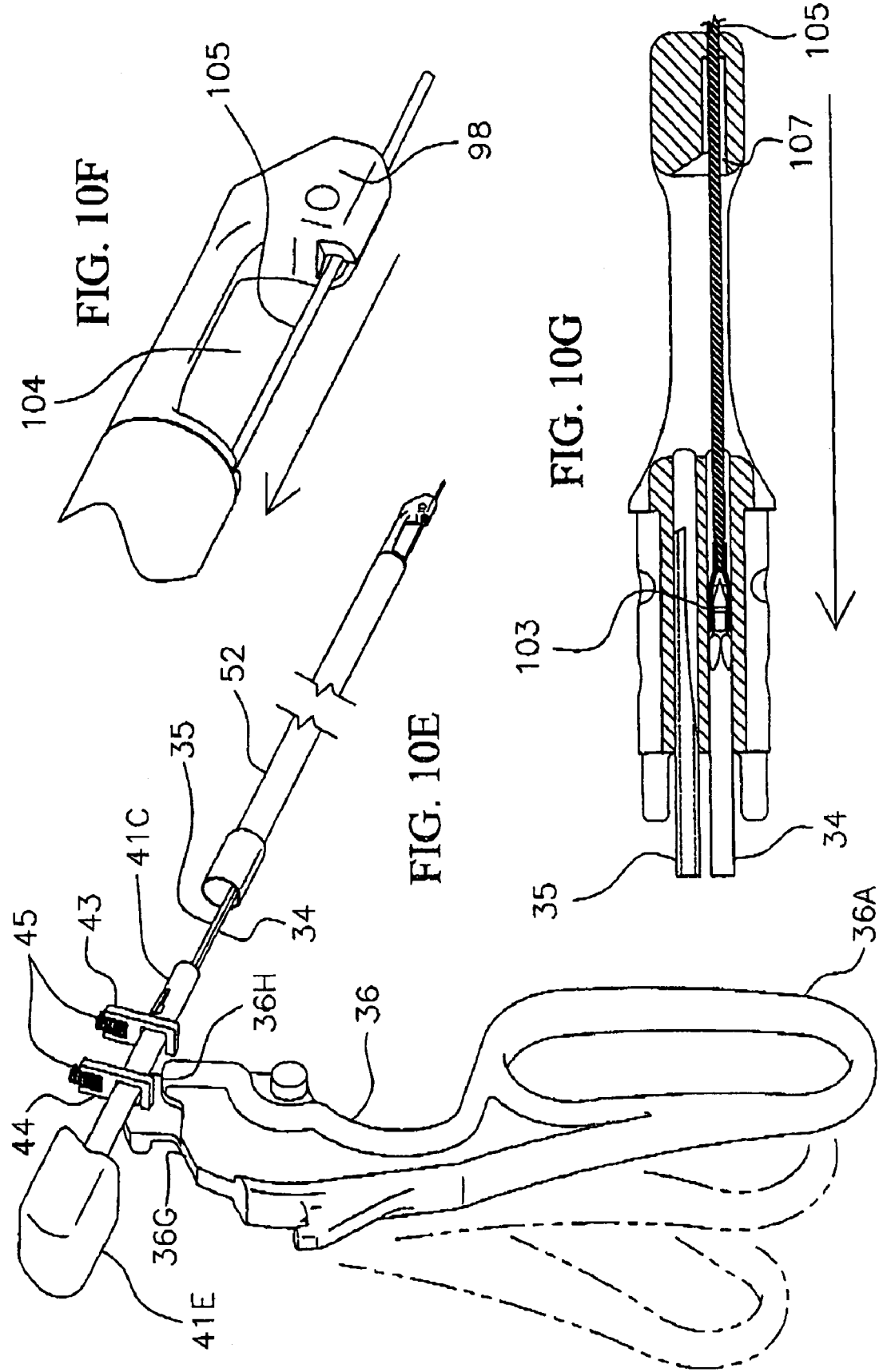

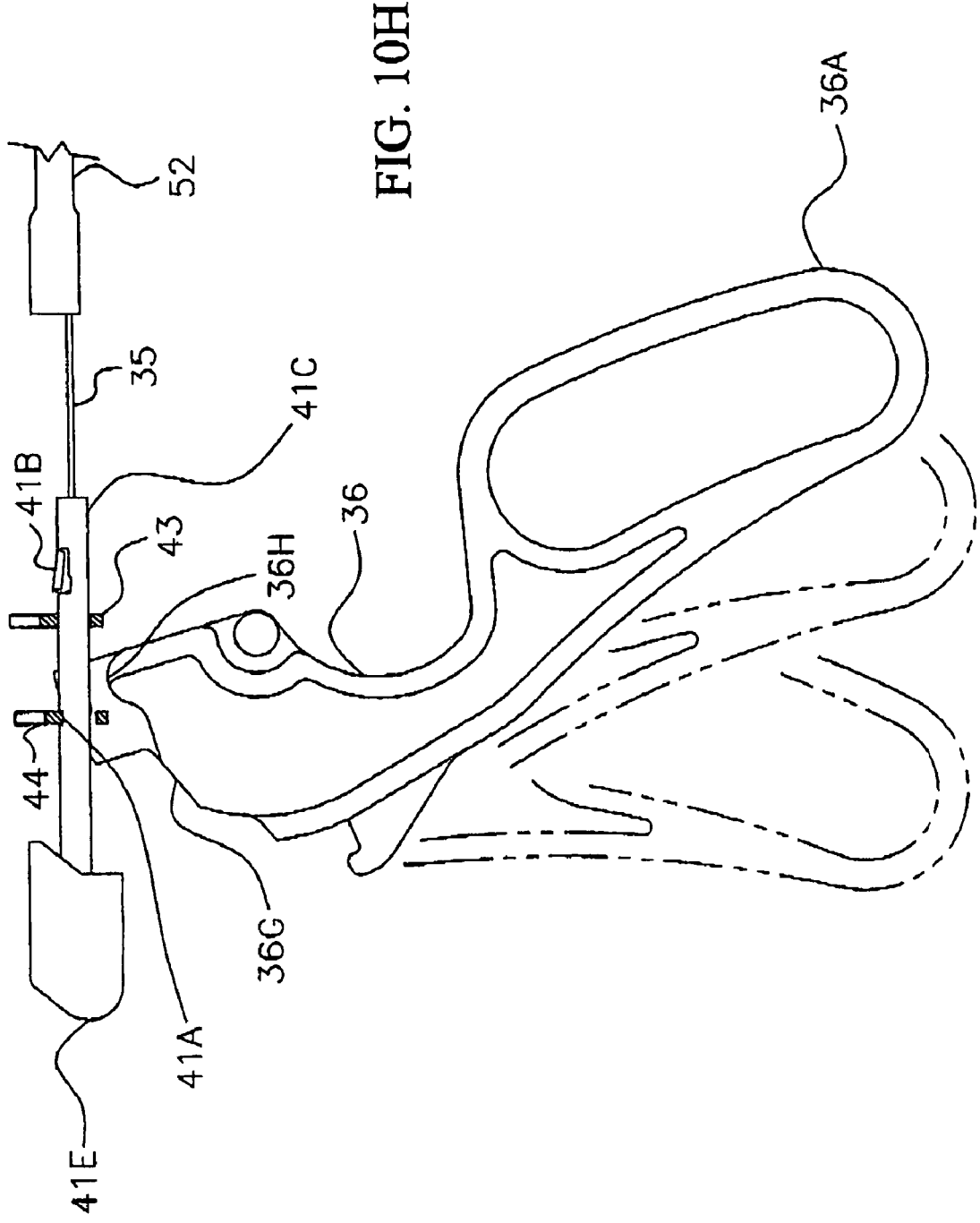

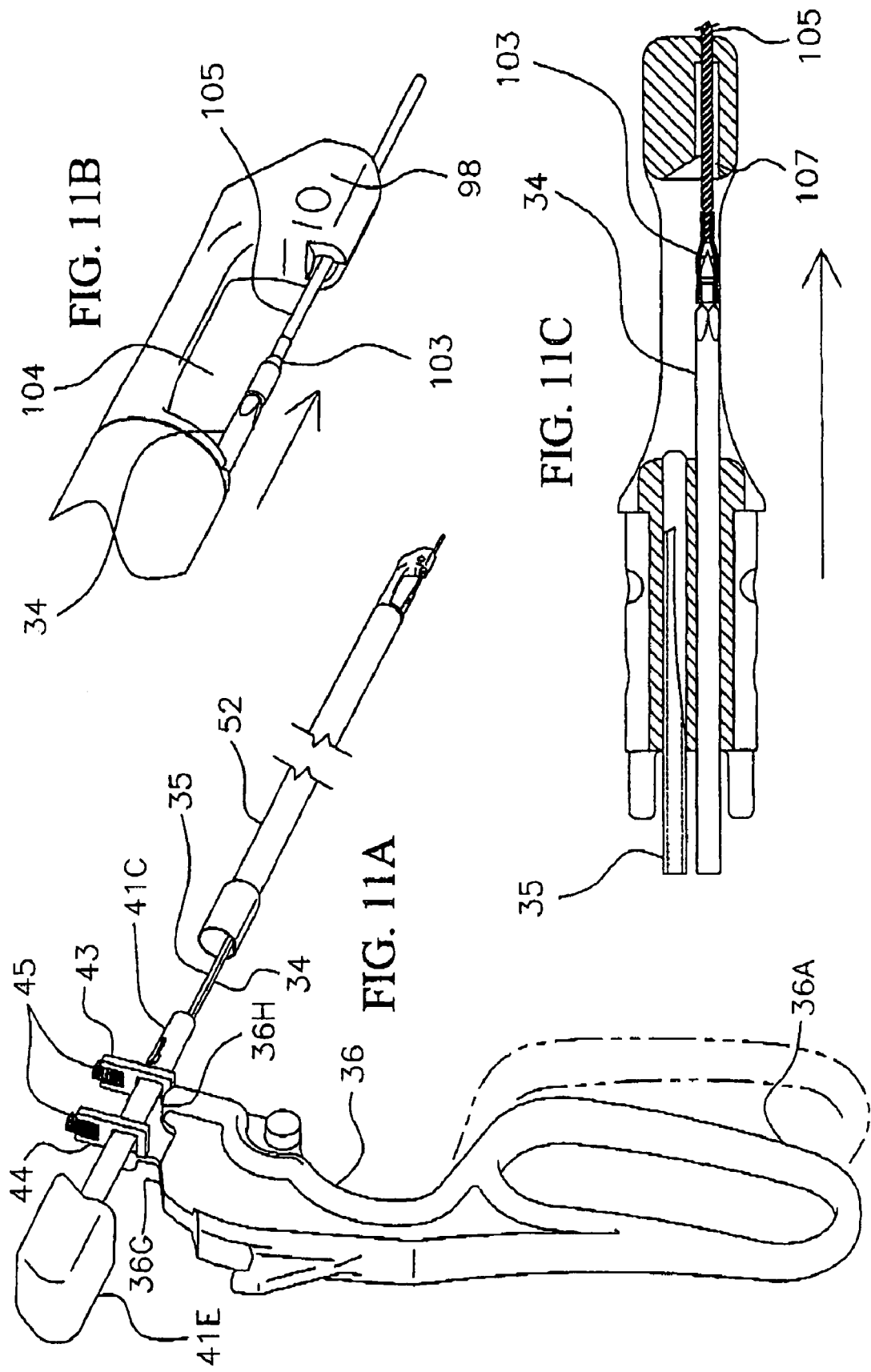

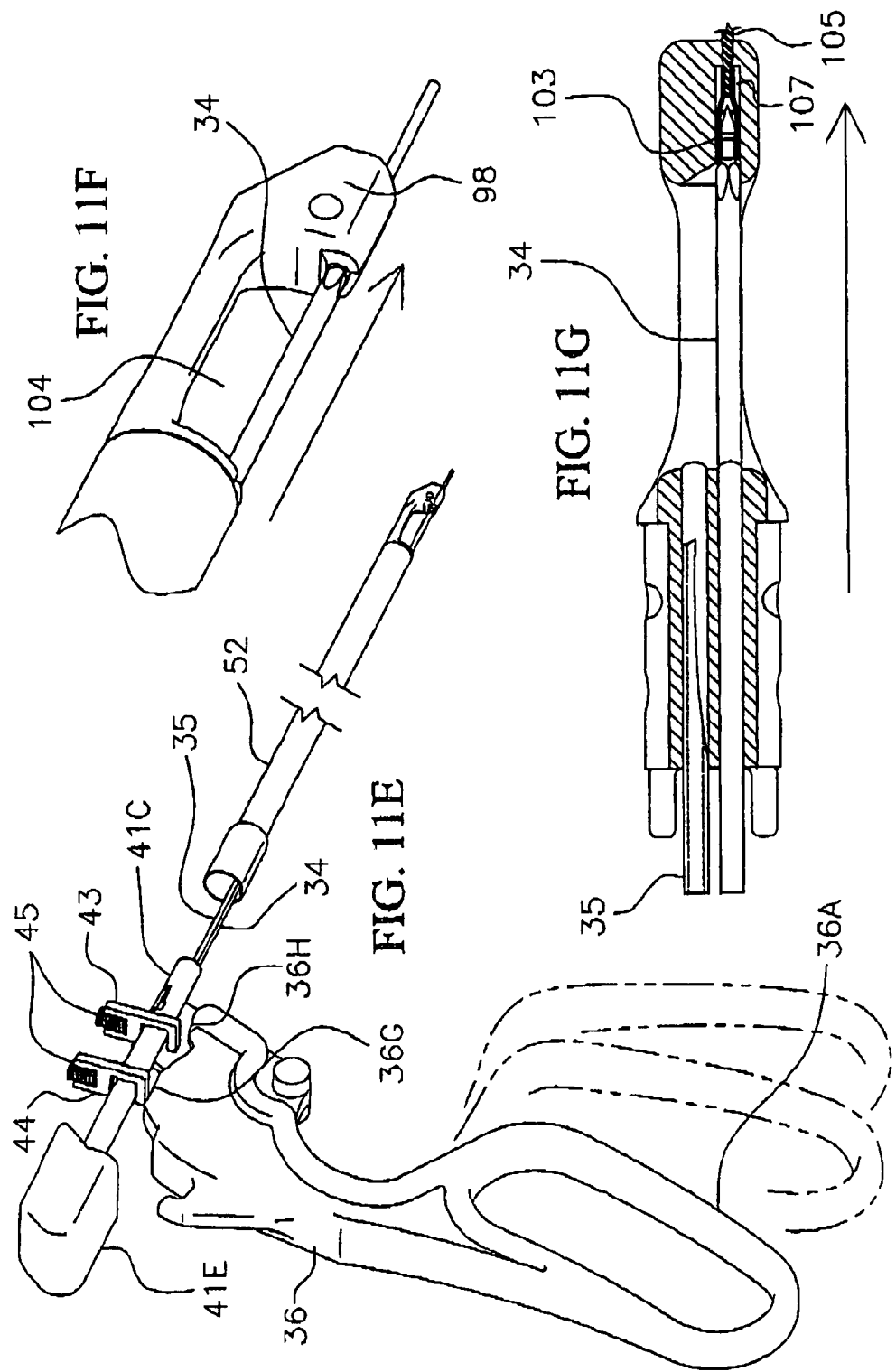

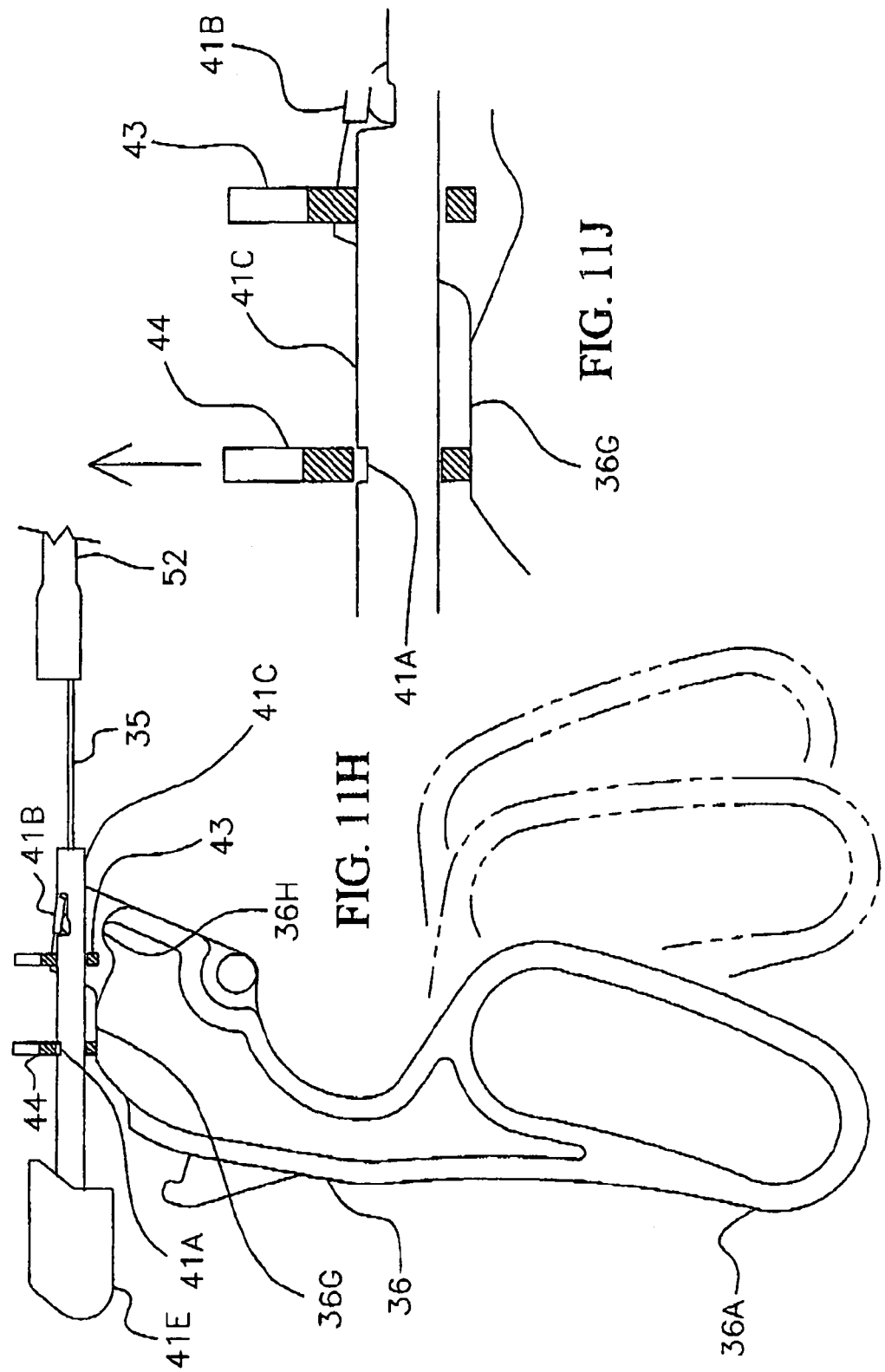

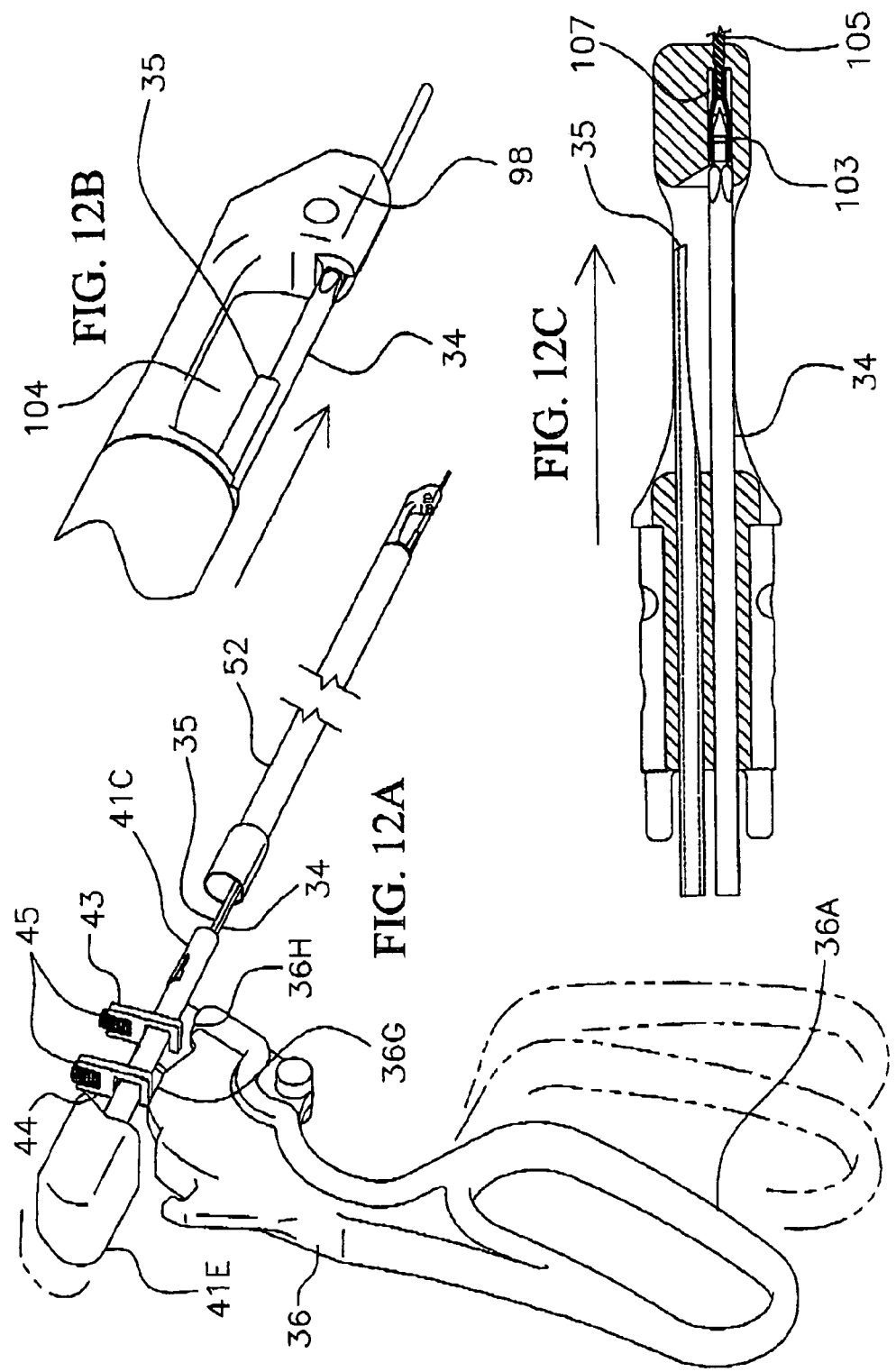

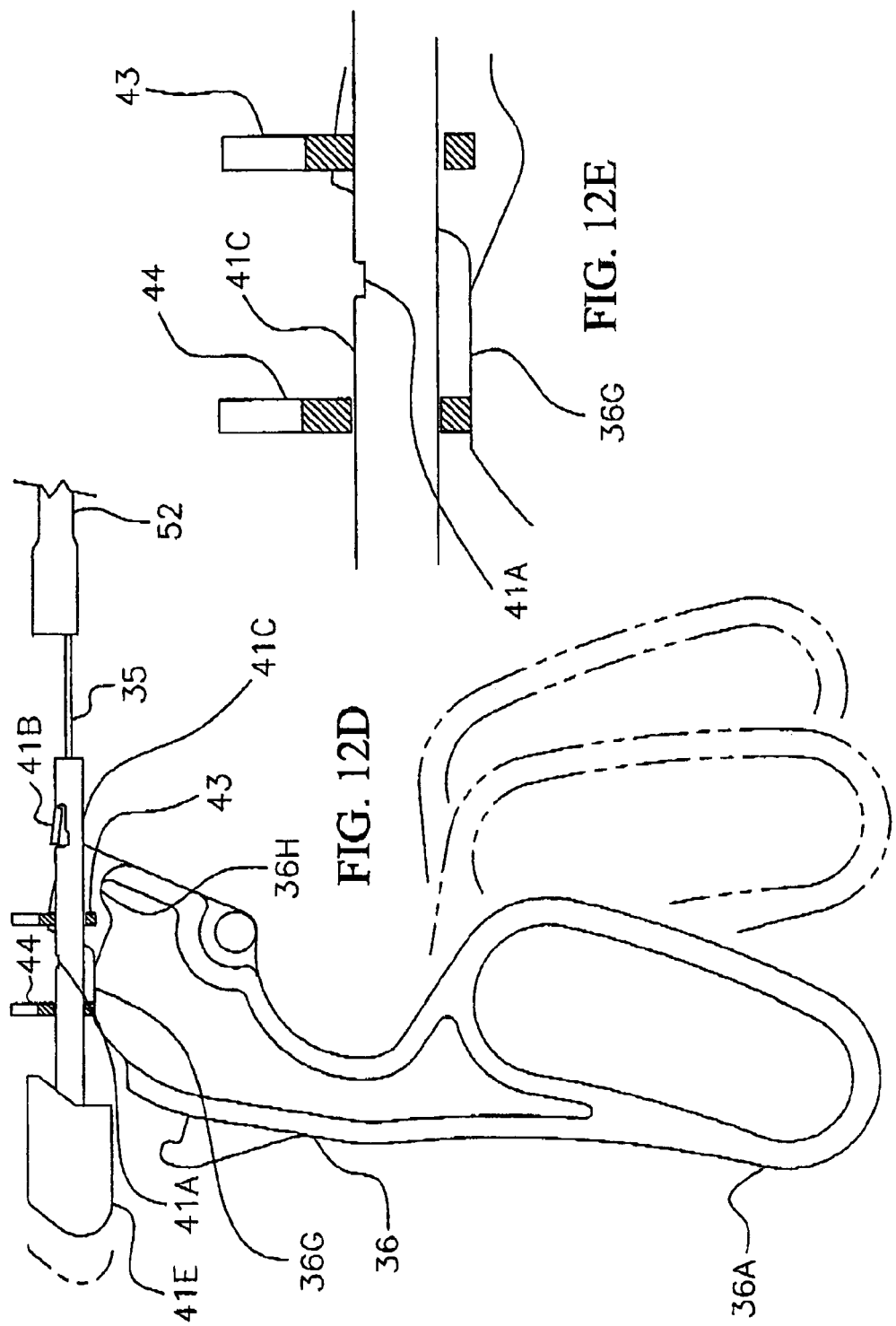

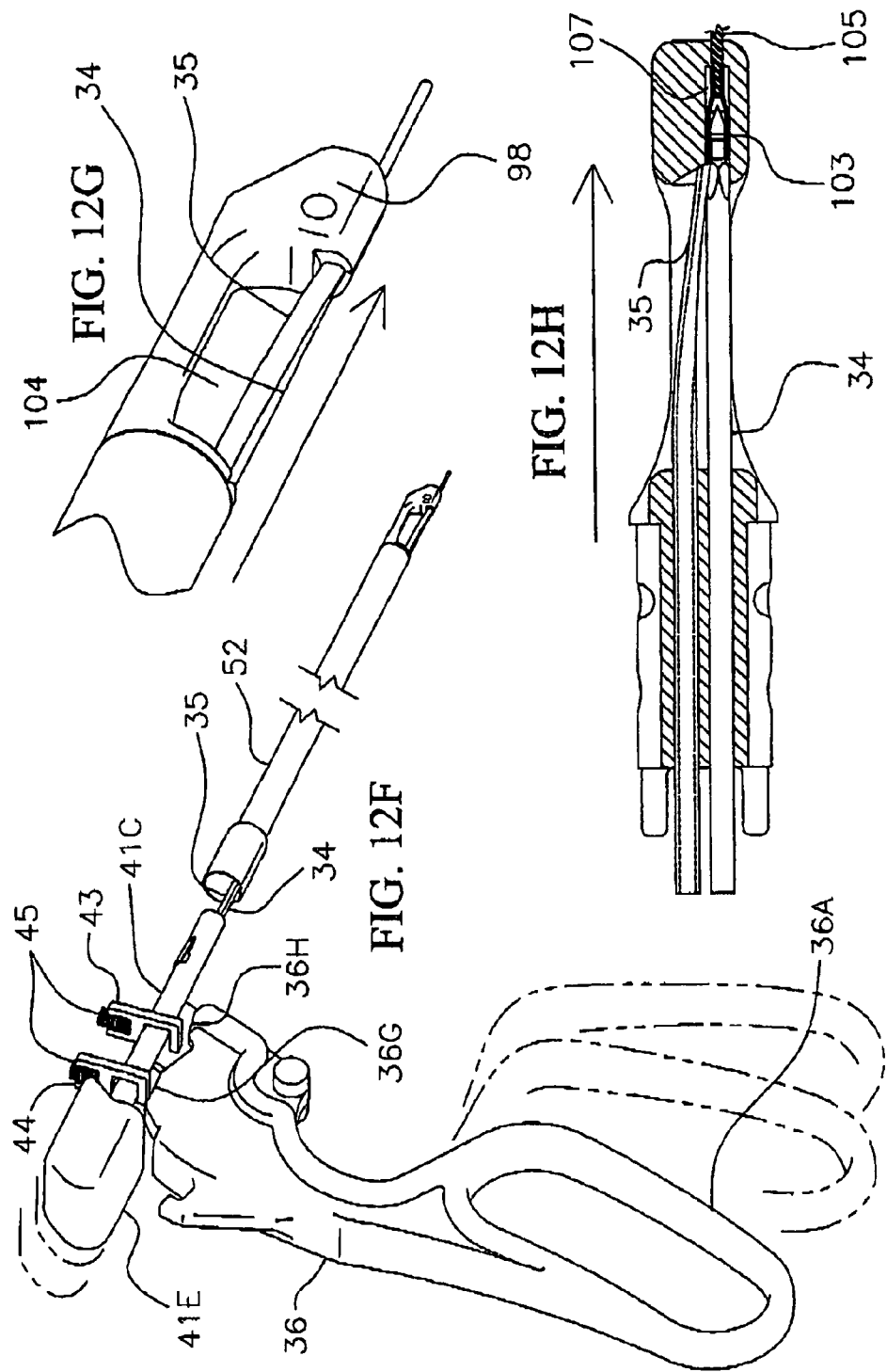

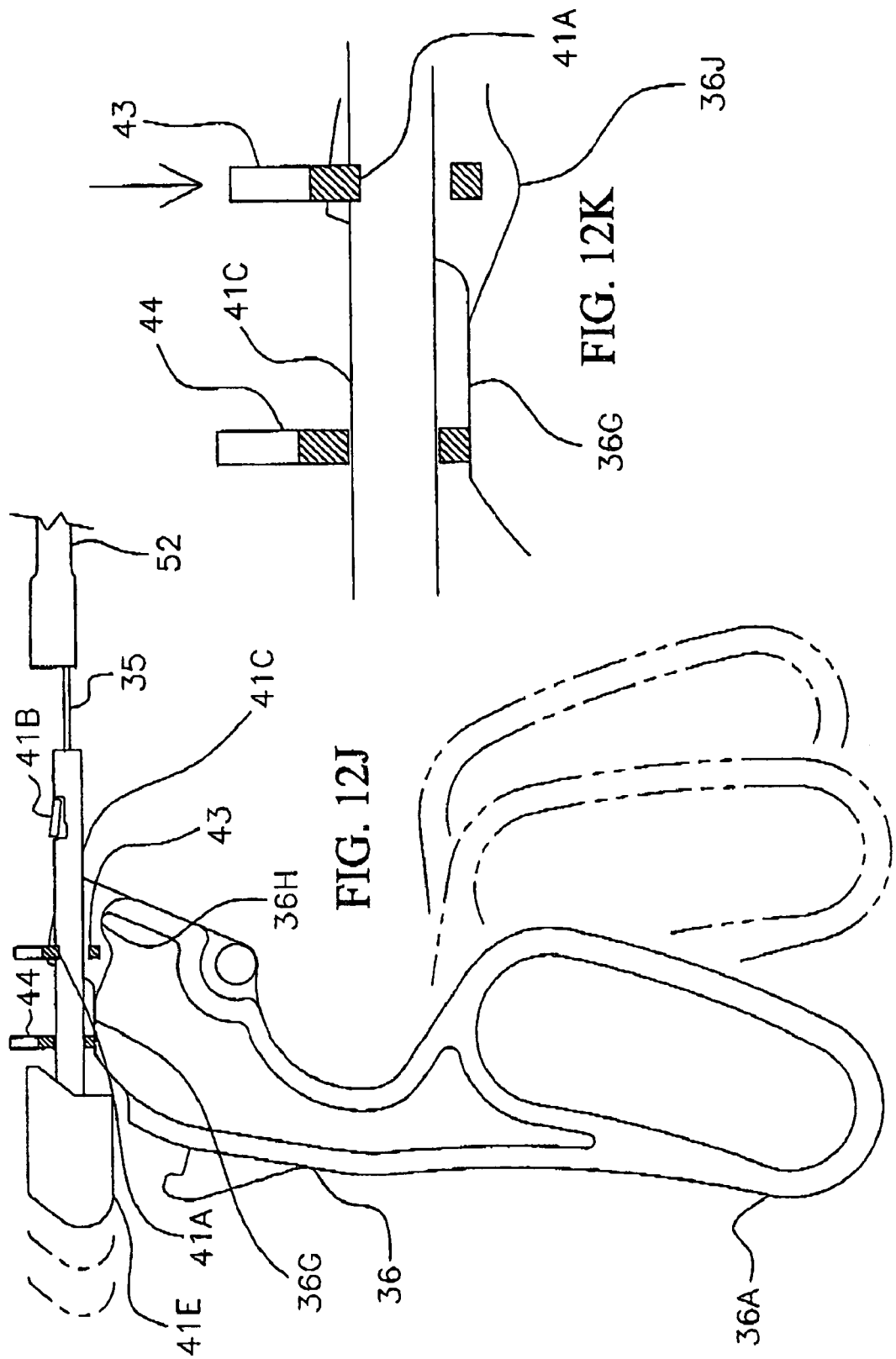

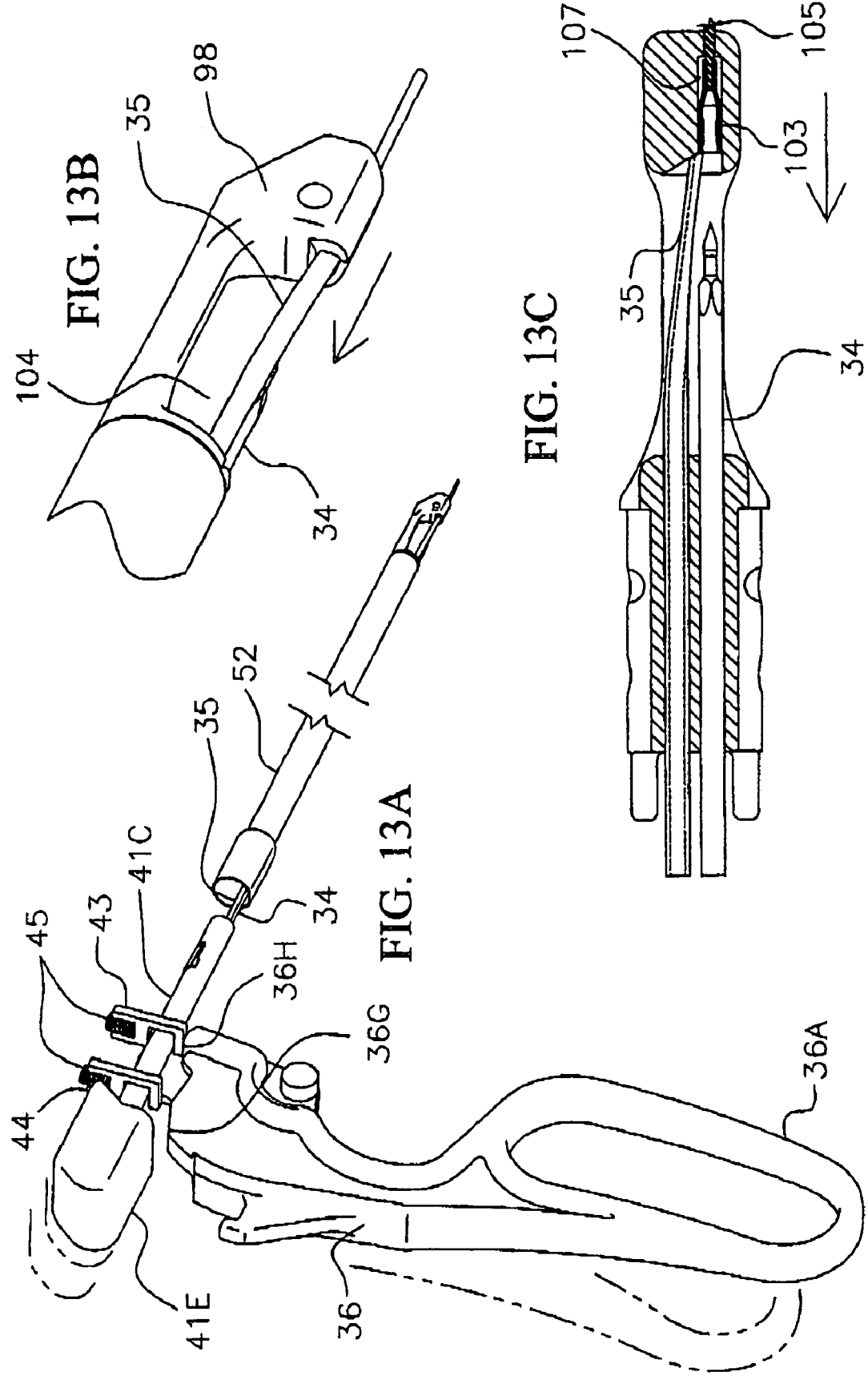

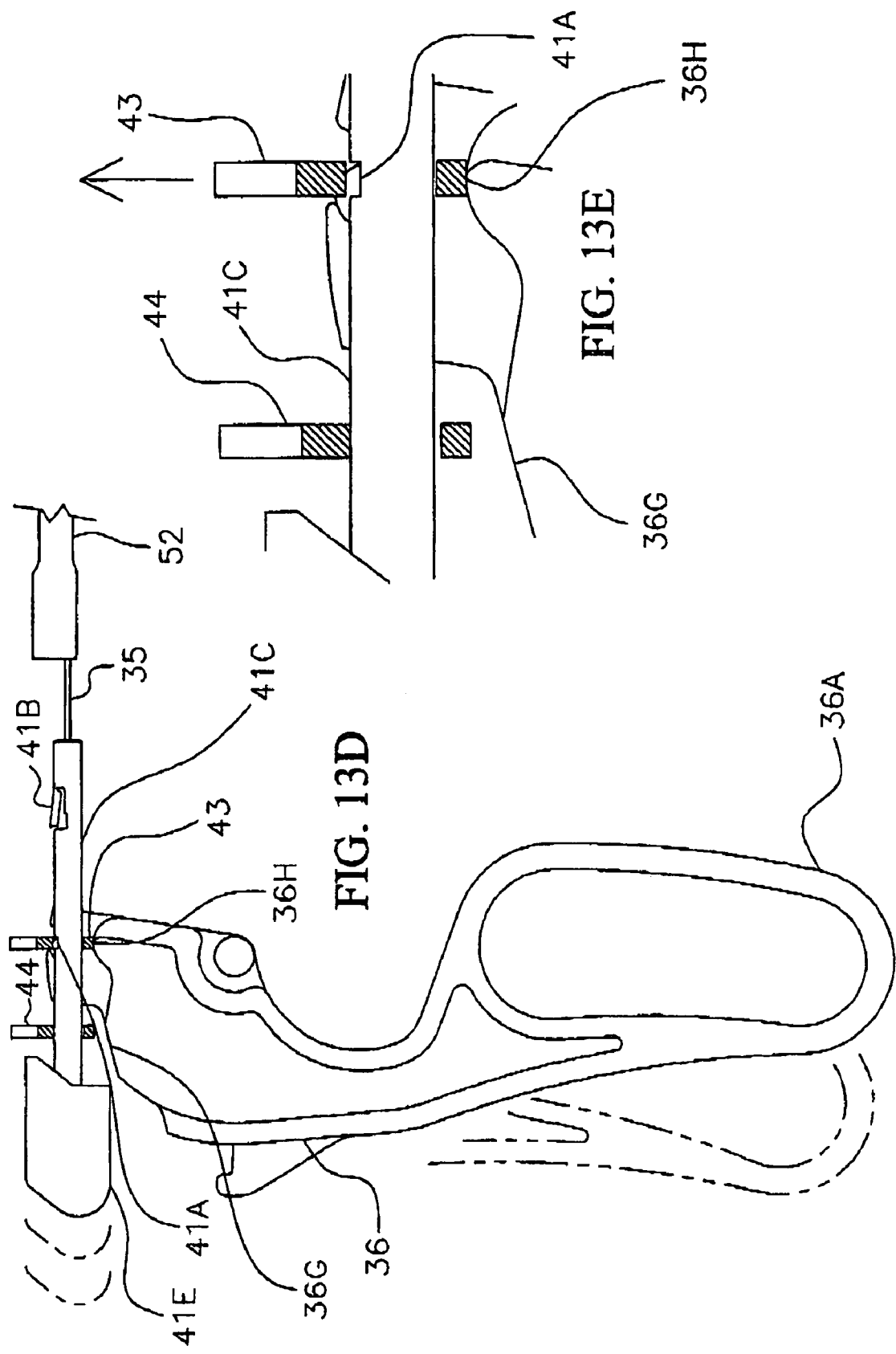

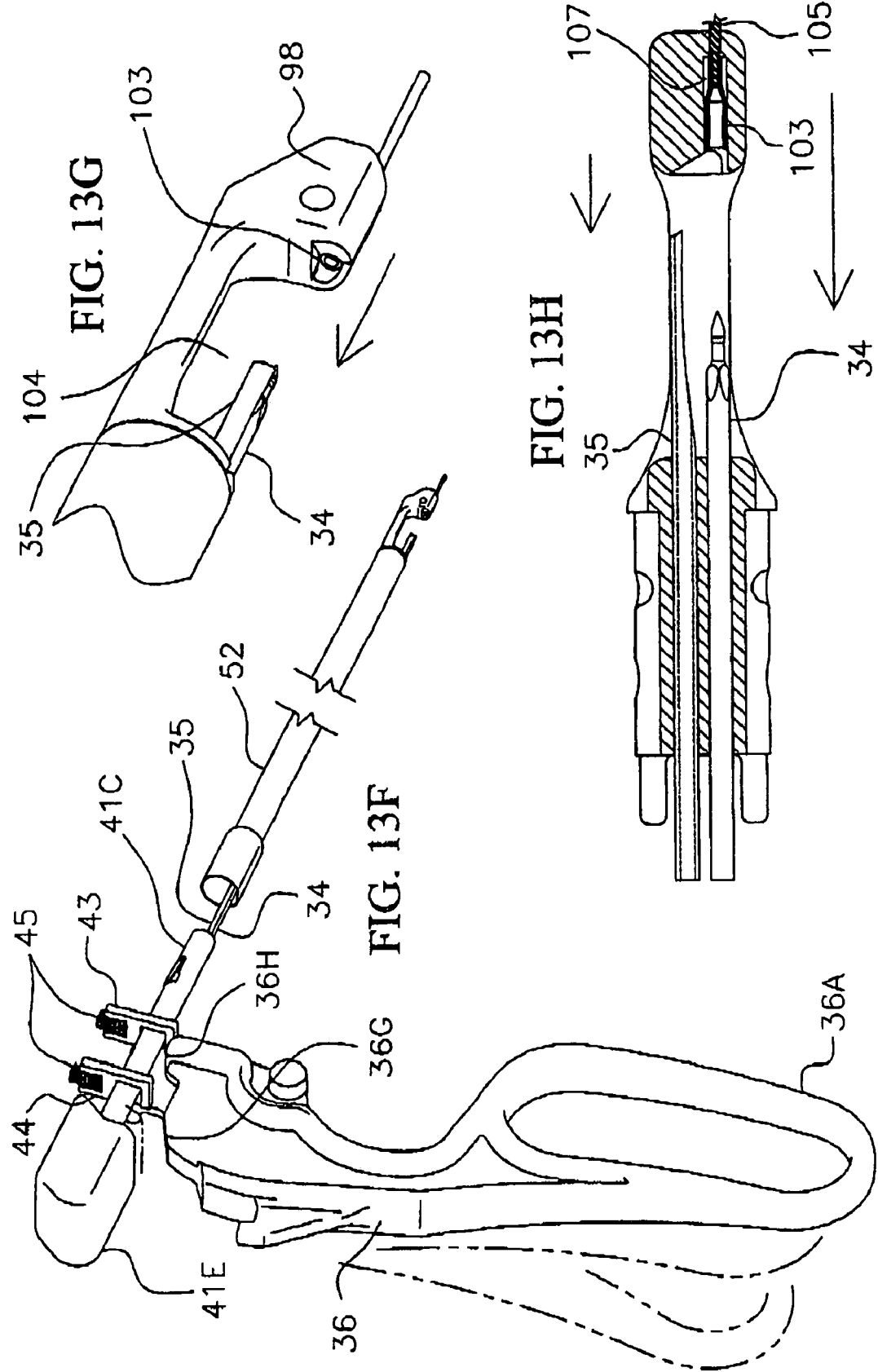

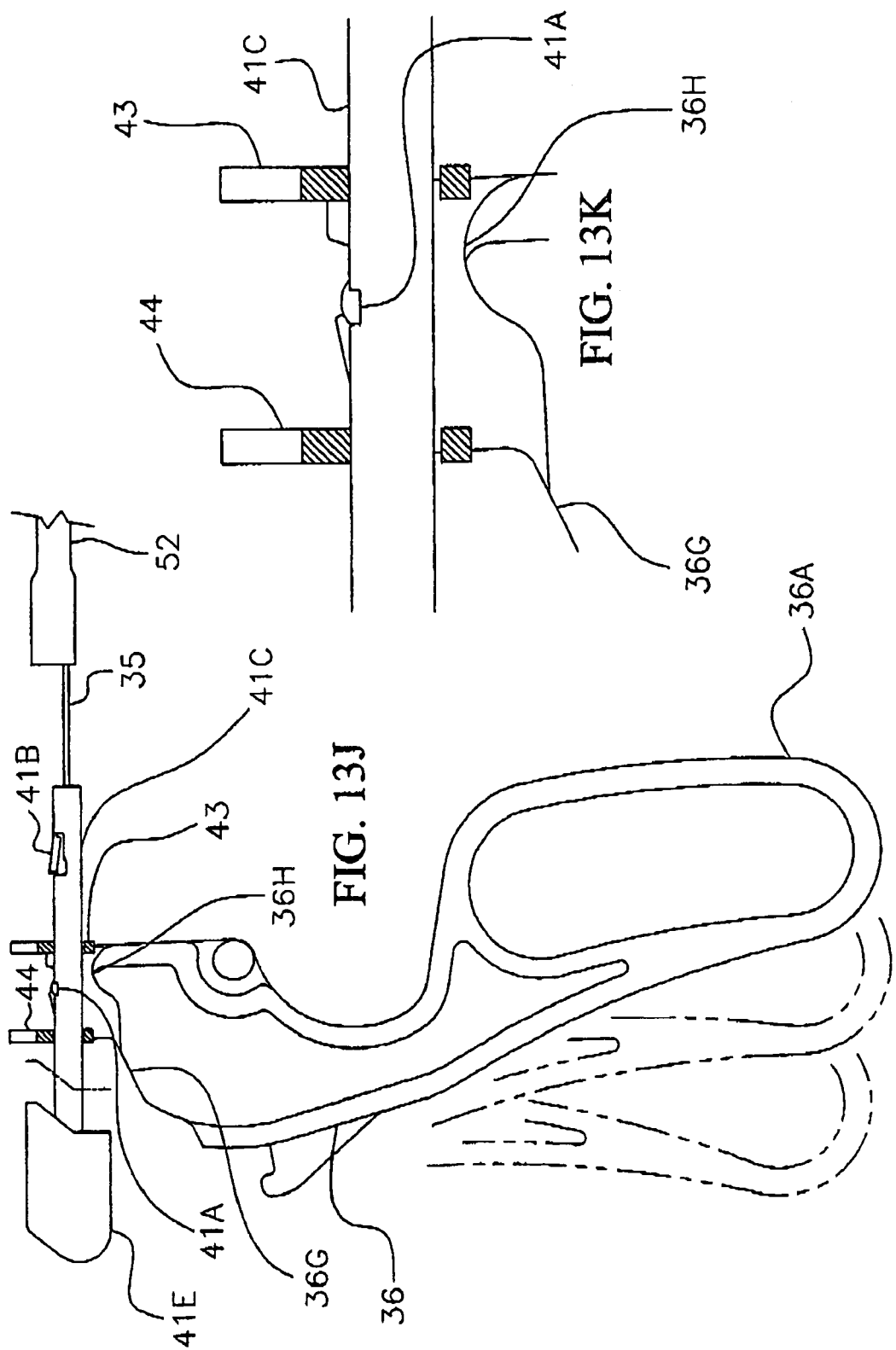

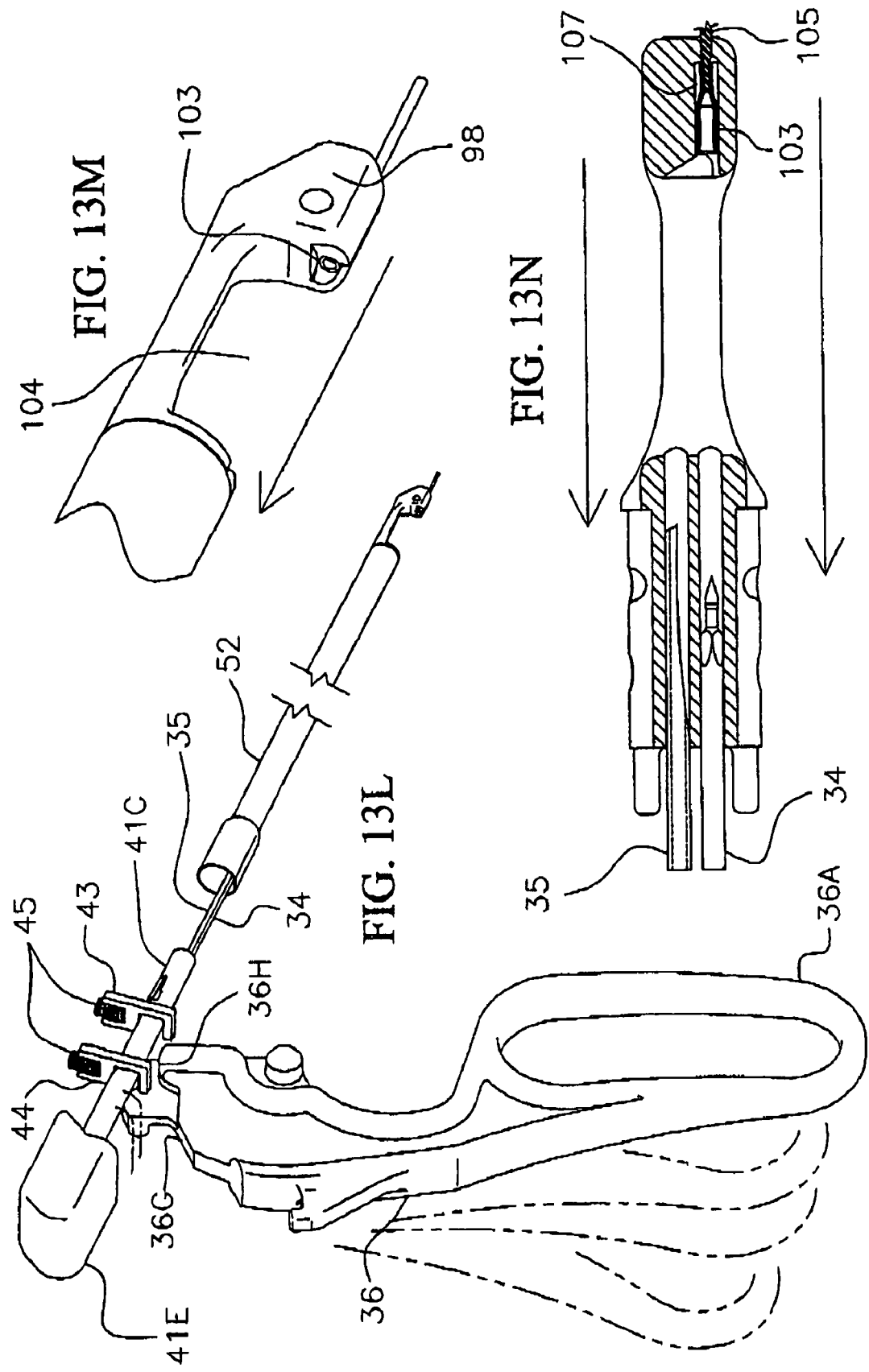

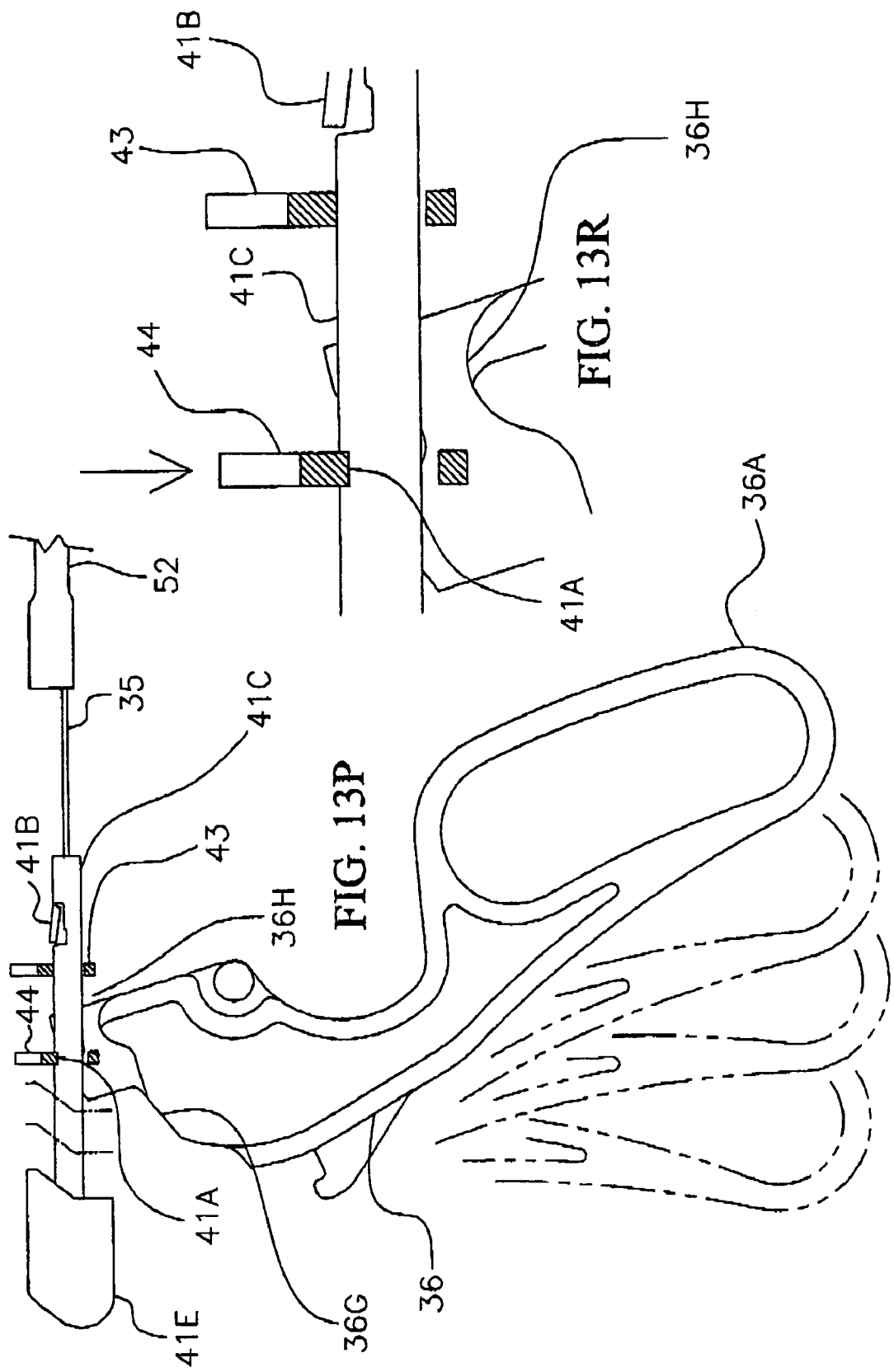

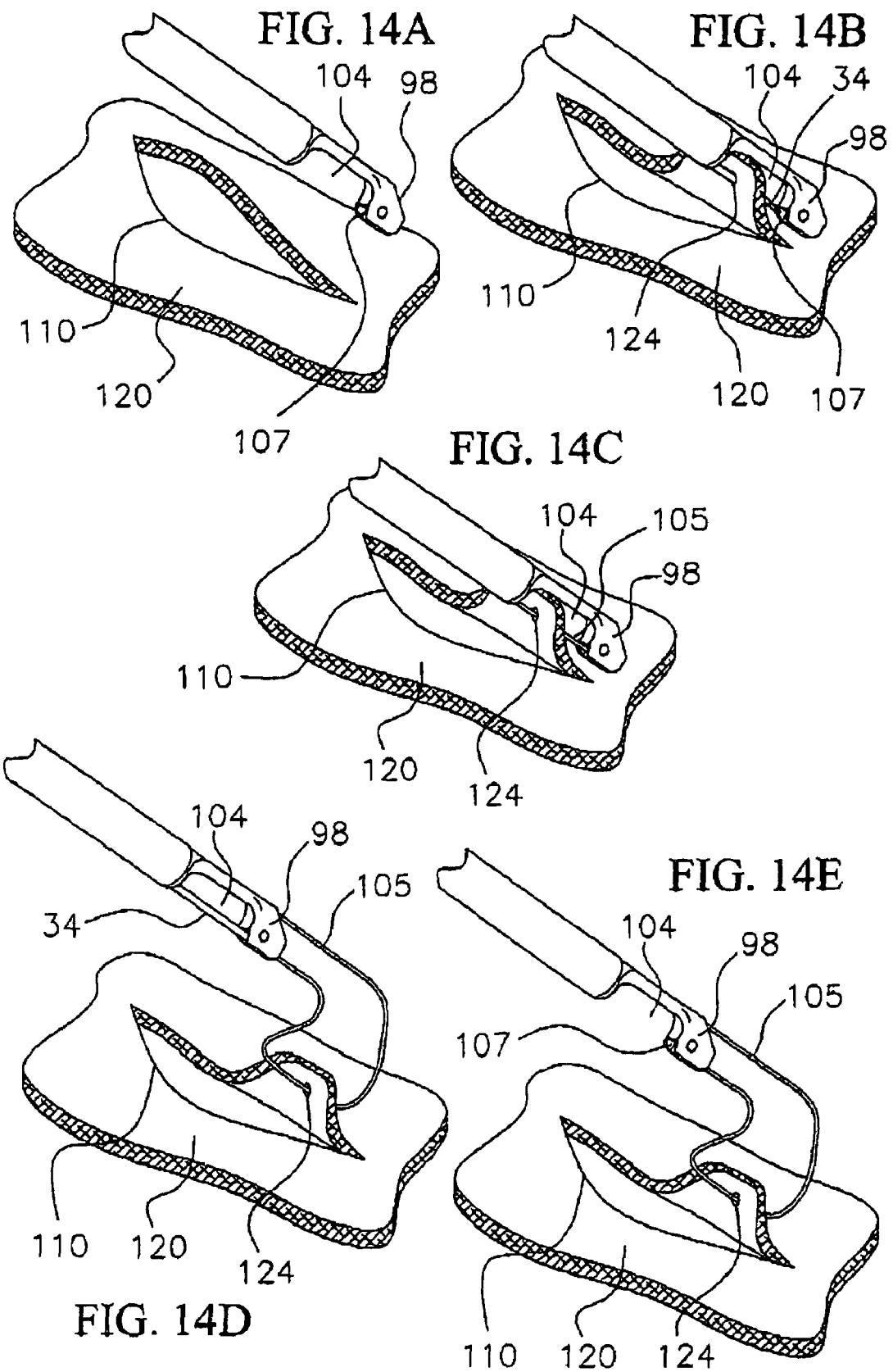

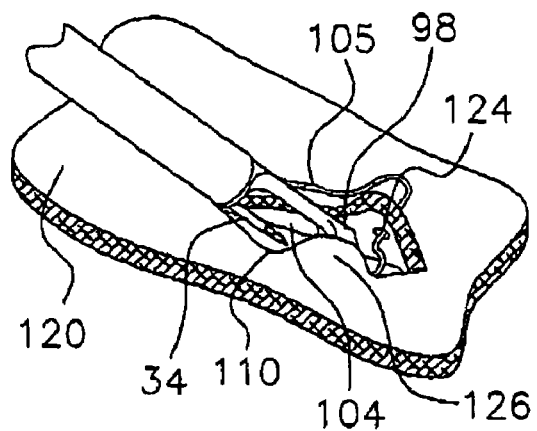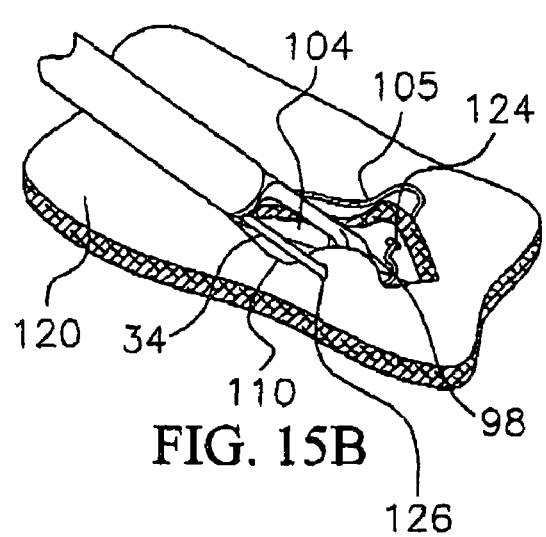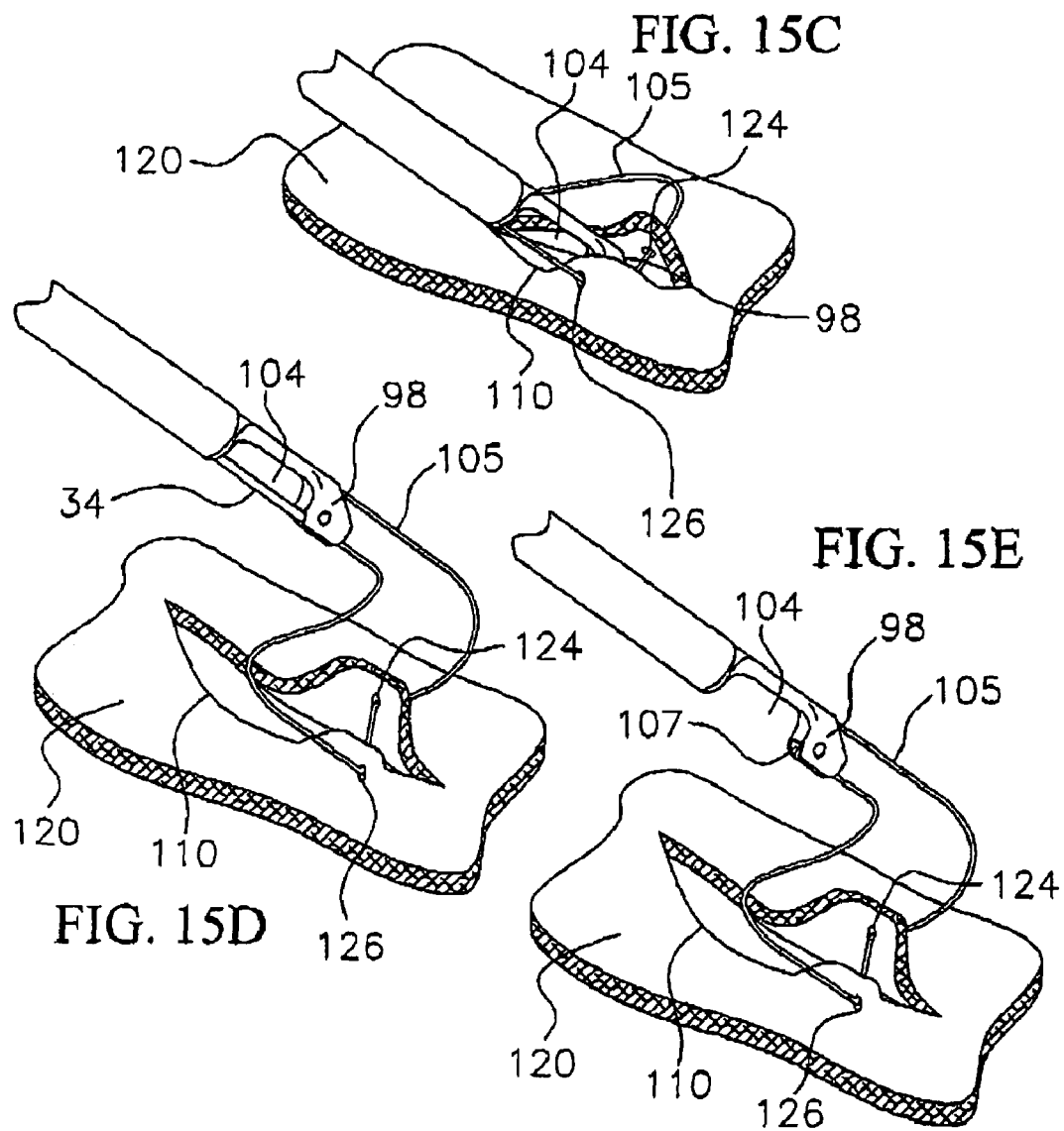
FIG. 15A
FIG. 15B
FIG. 15C
FIG. 15D
FIG. 15E

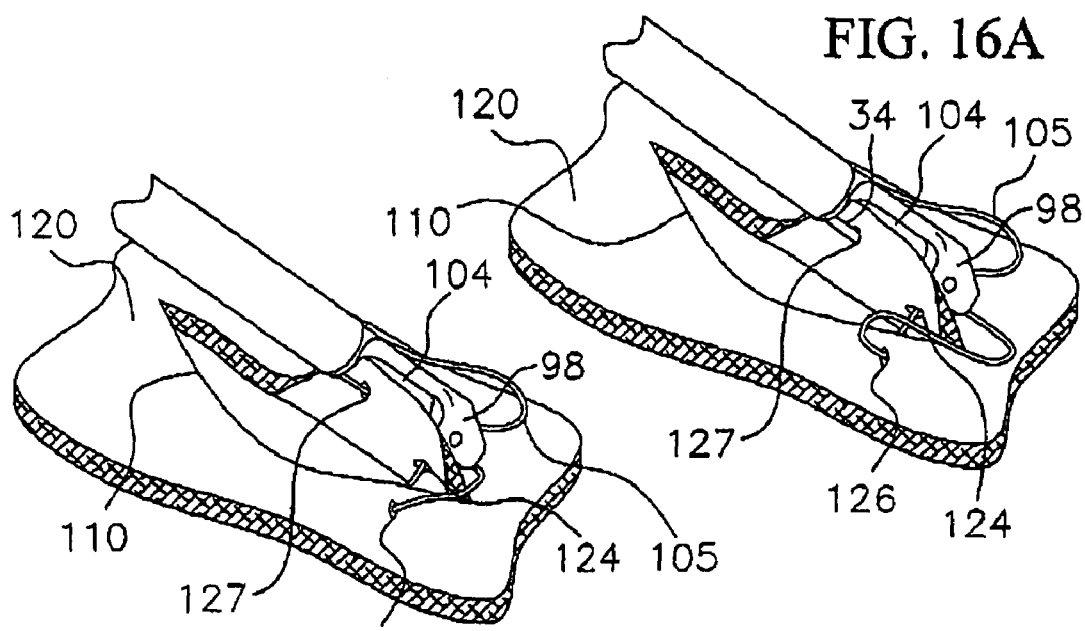
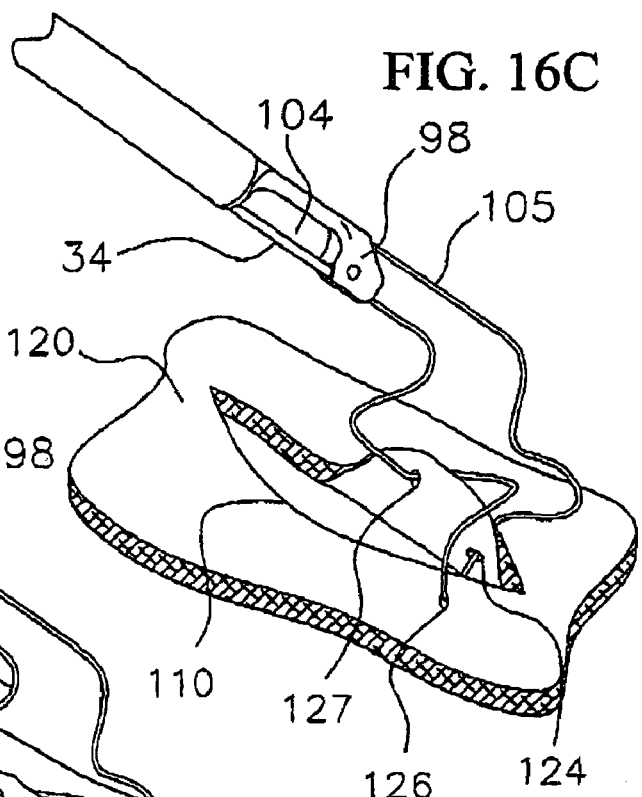
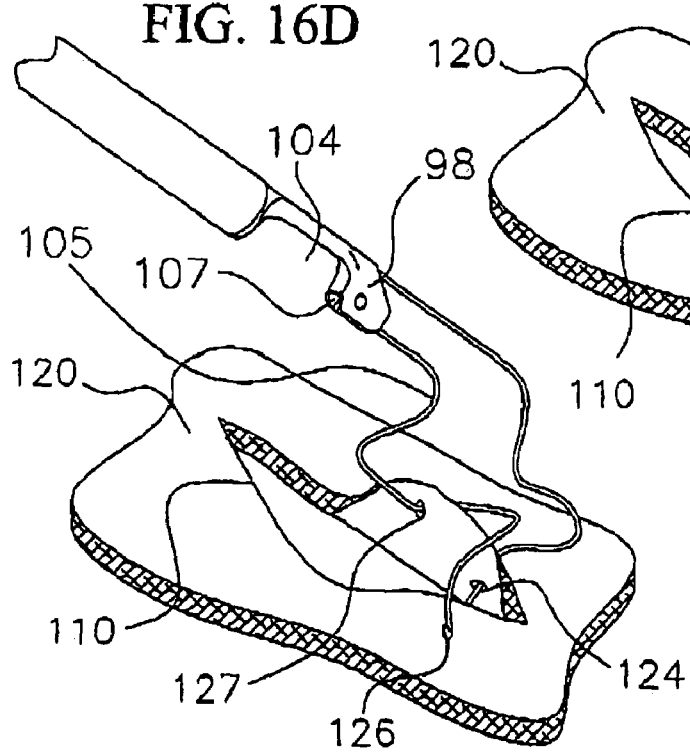
FIG. 16A
FIG. 16B
FIG. 16C
FIG. 16D

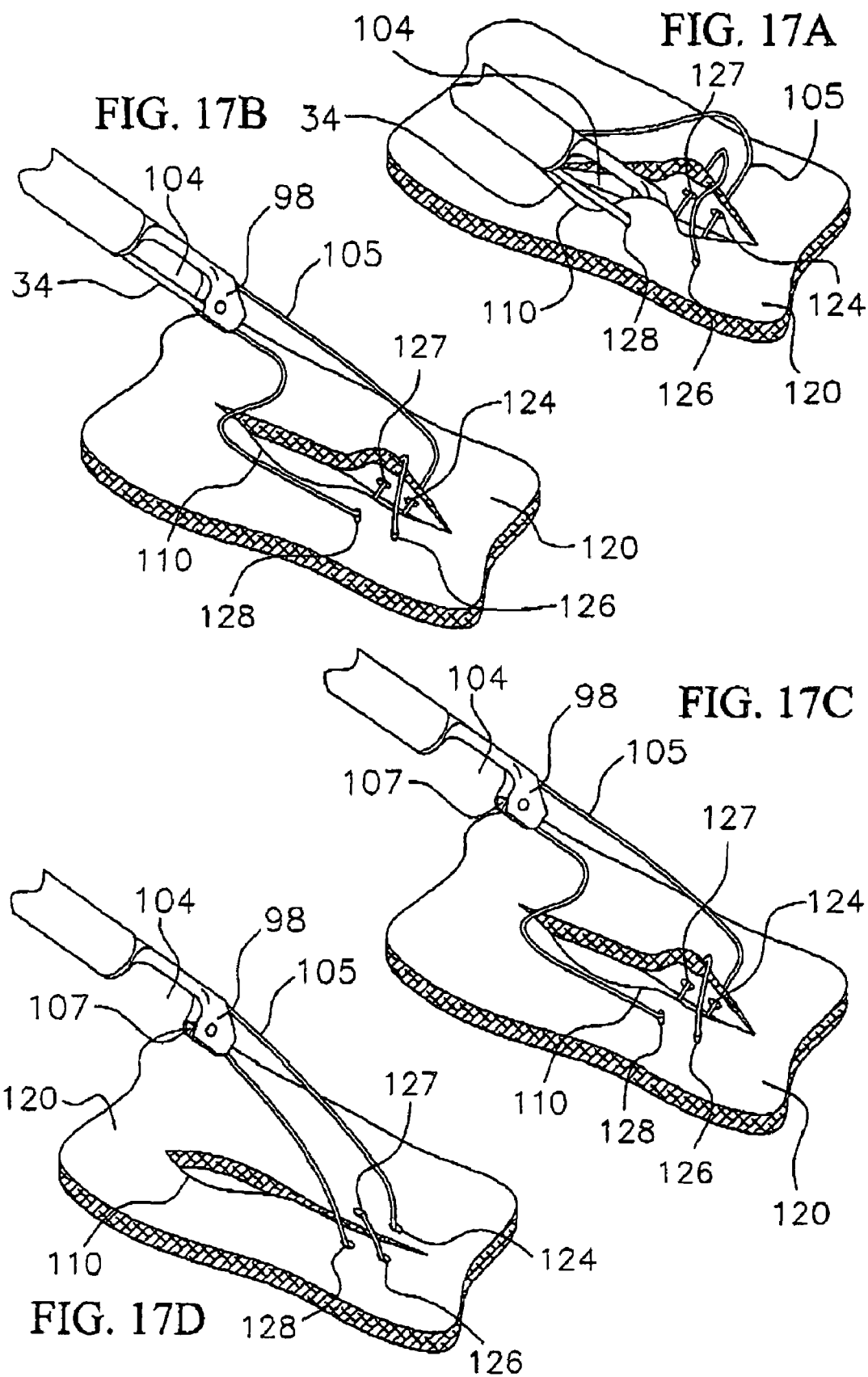

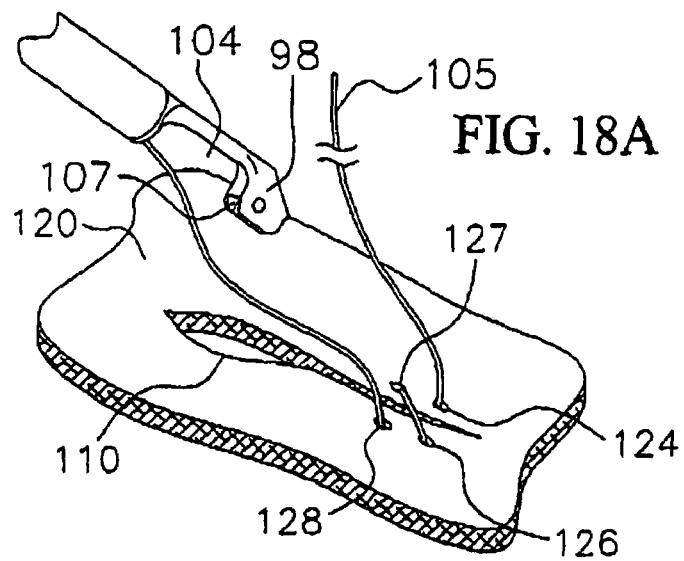
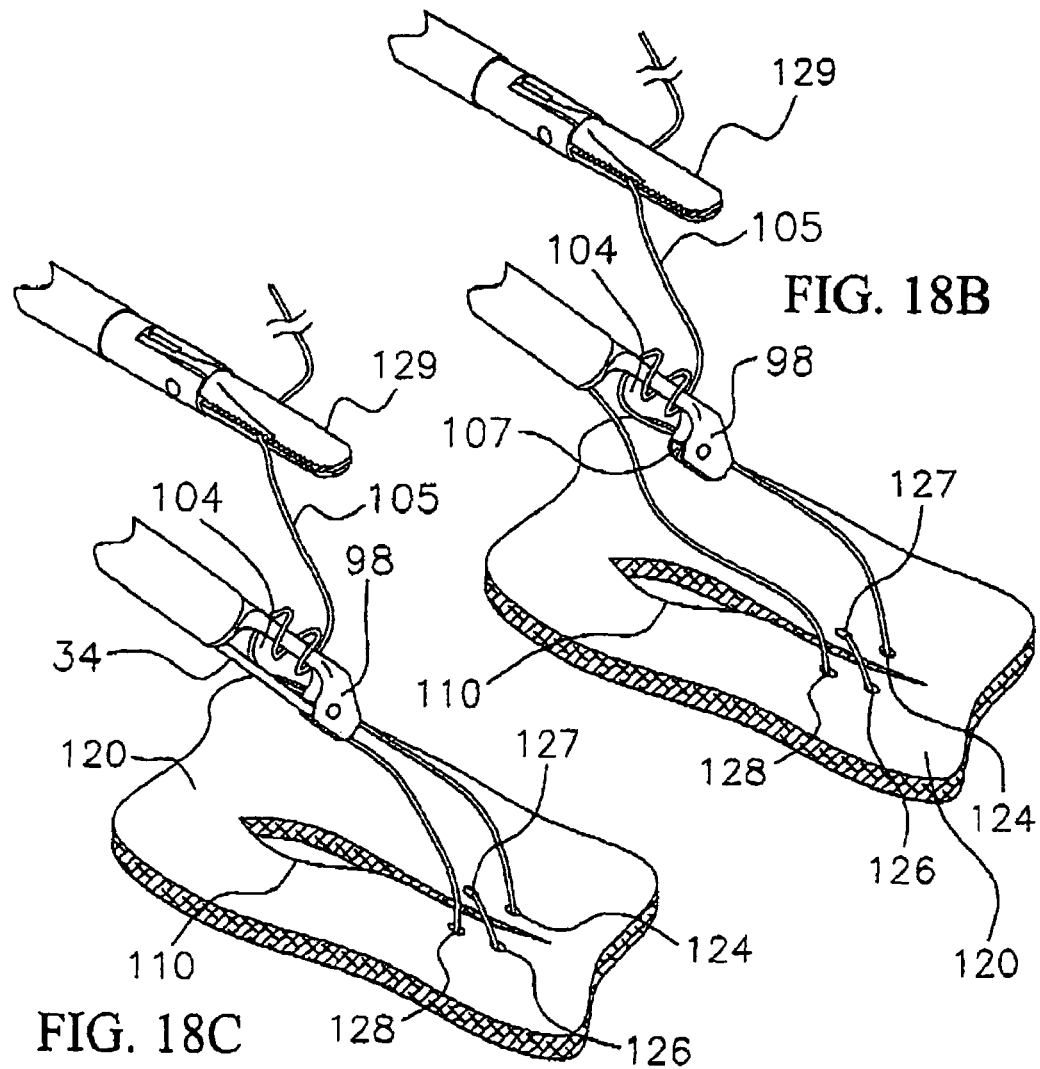
FIG. 18A
FIG. 18B
FIG. 18C

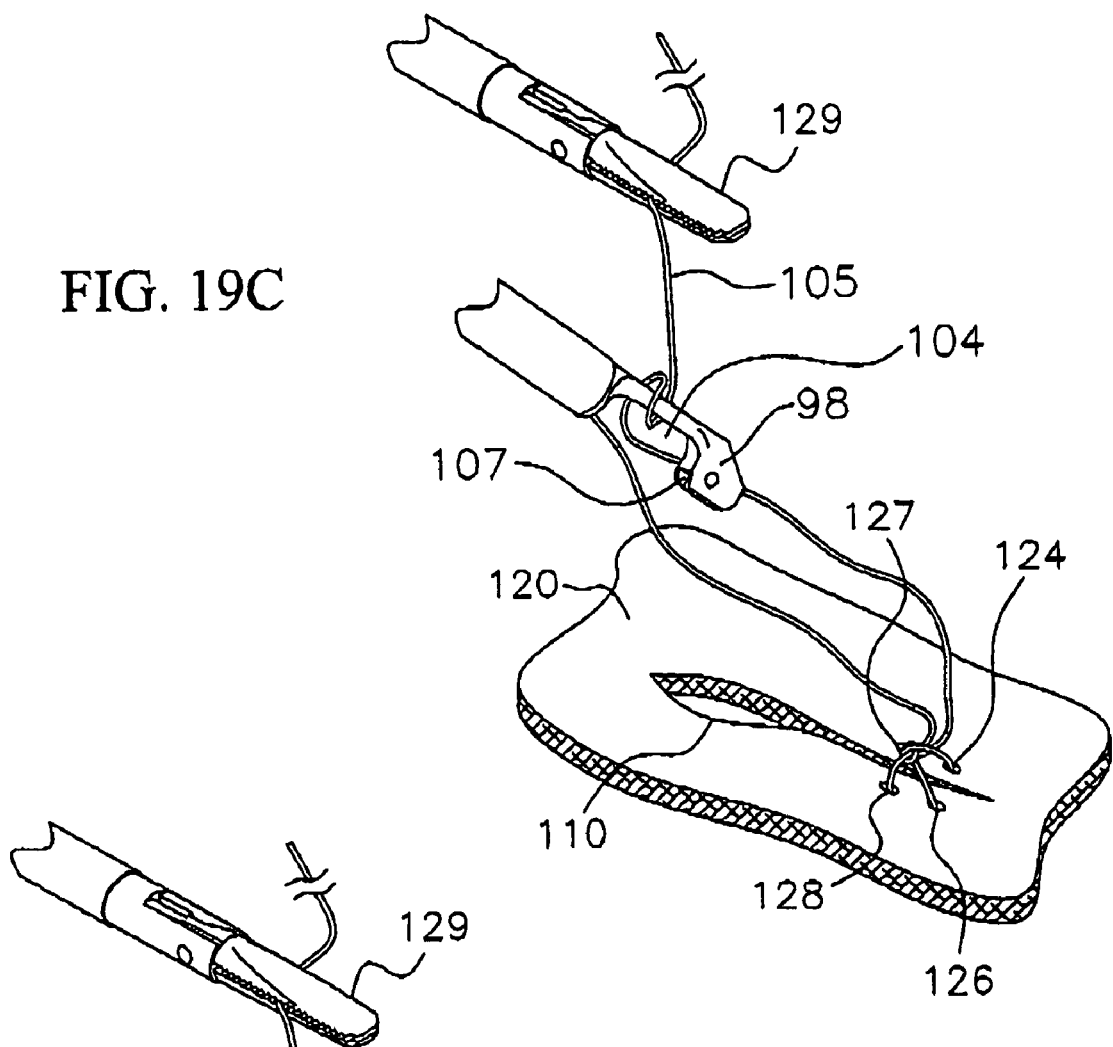
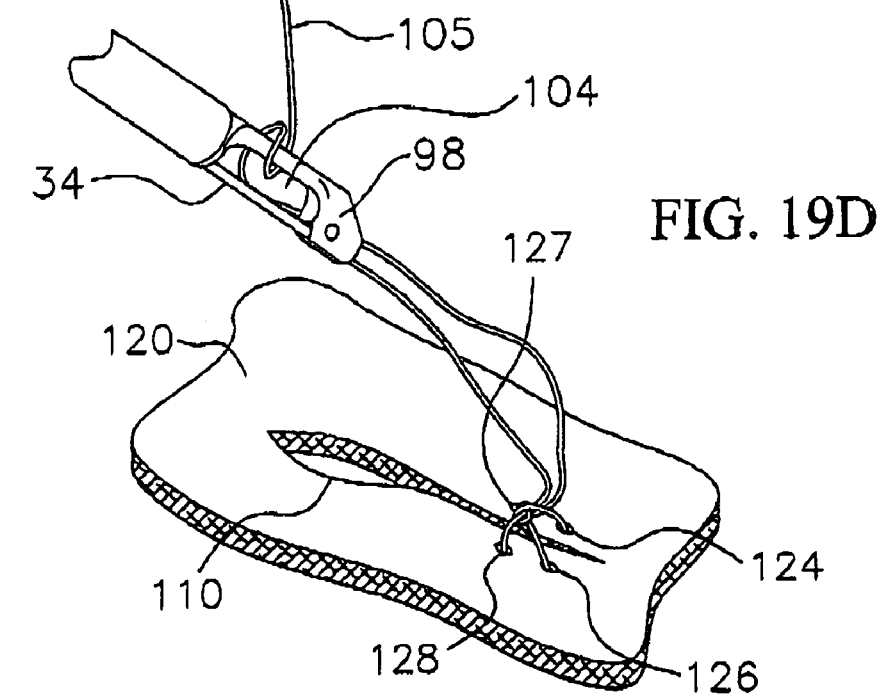

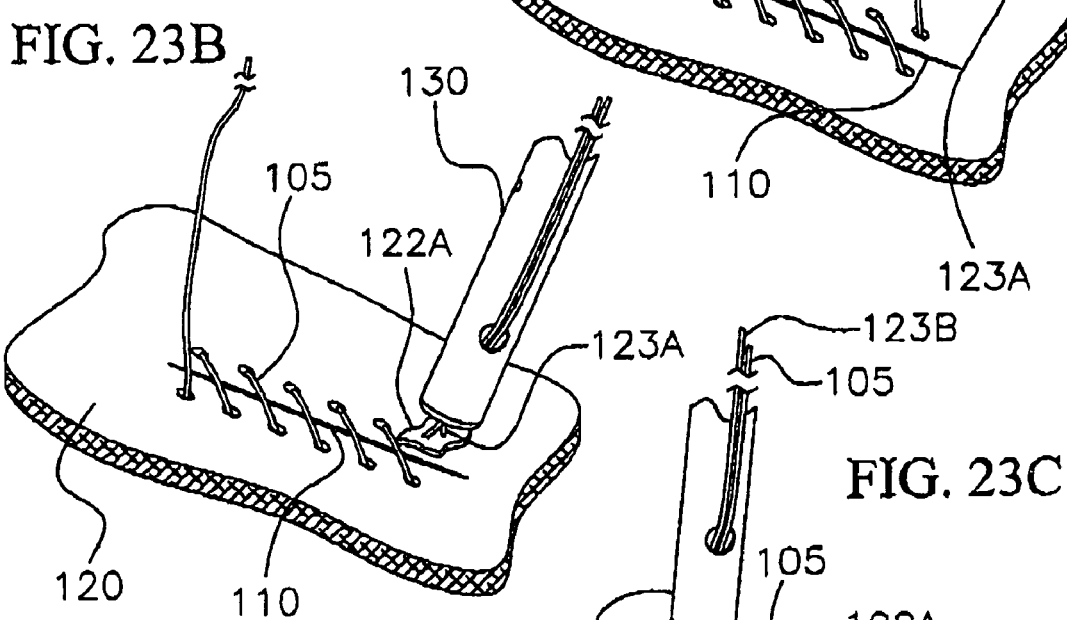
FIG. 23A
FIG. 23B
FIG. 23C
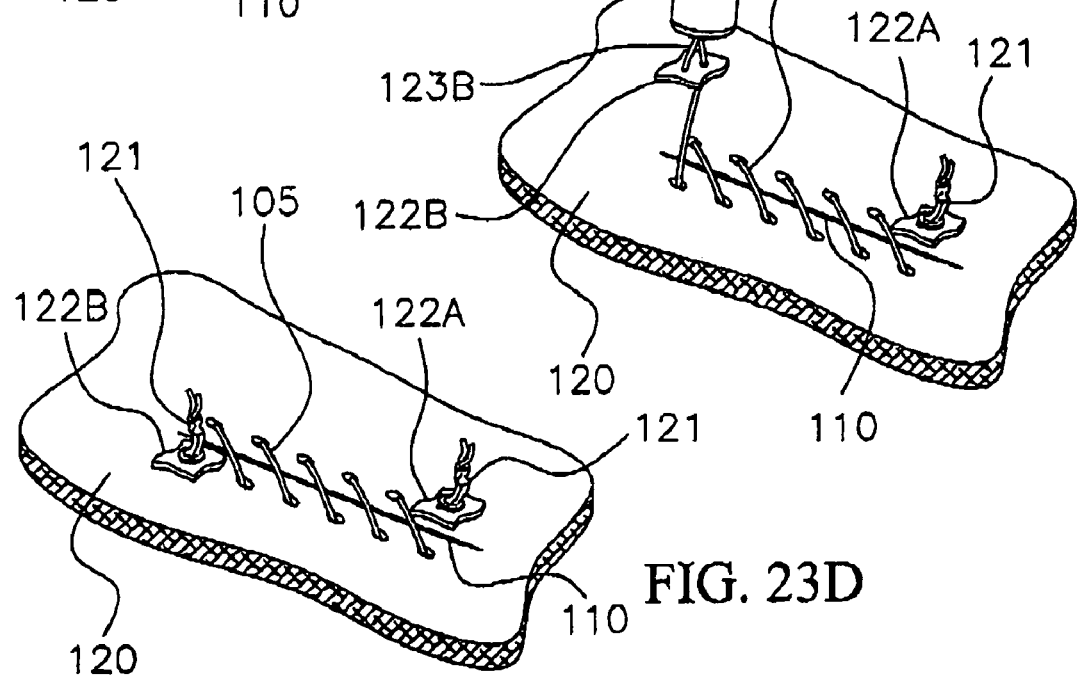
FIG. 23D

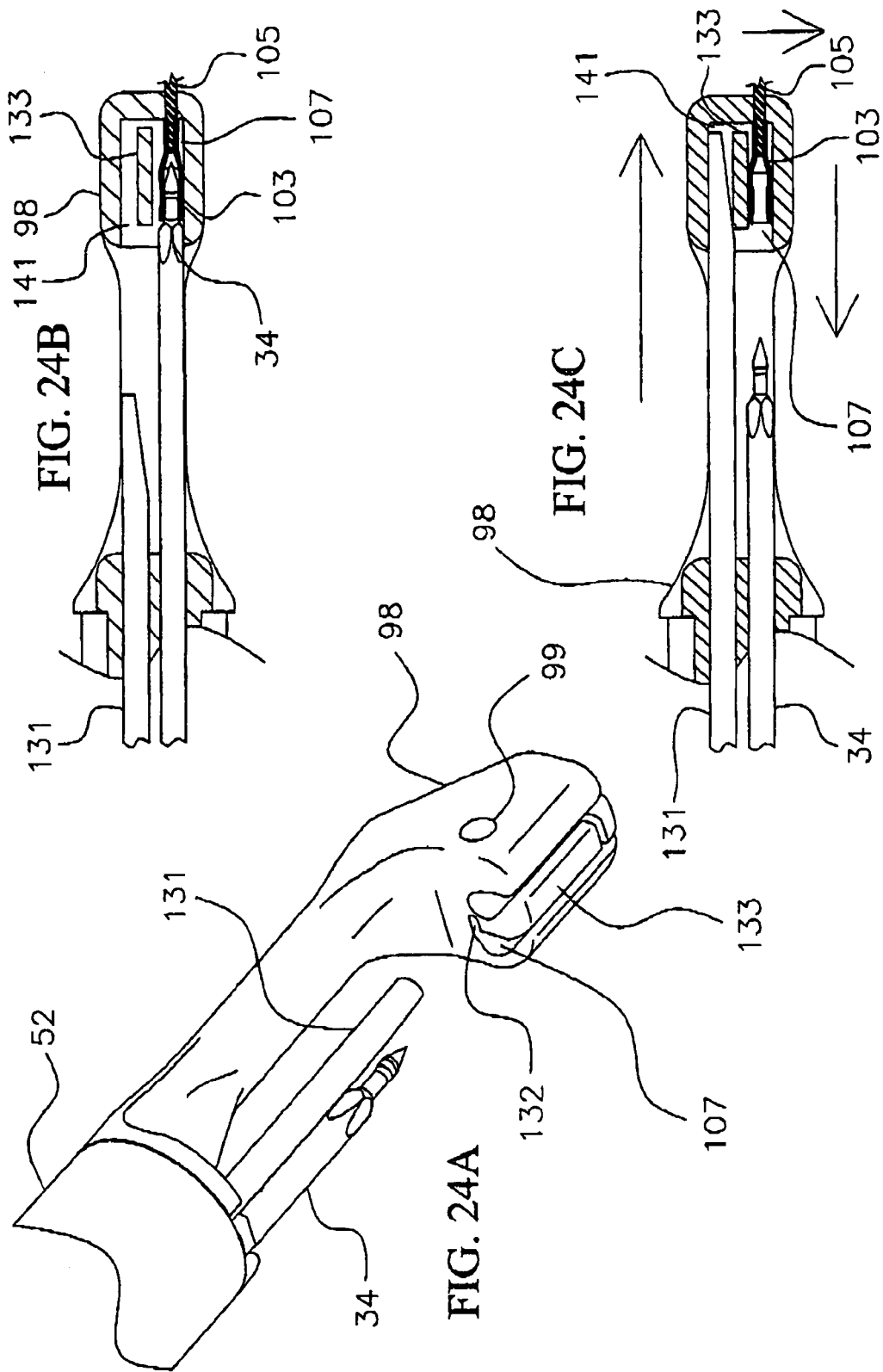

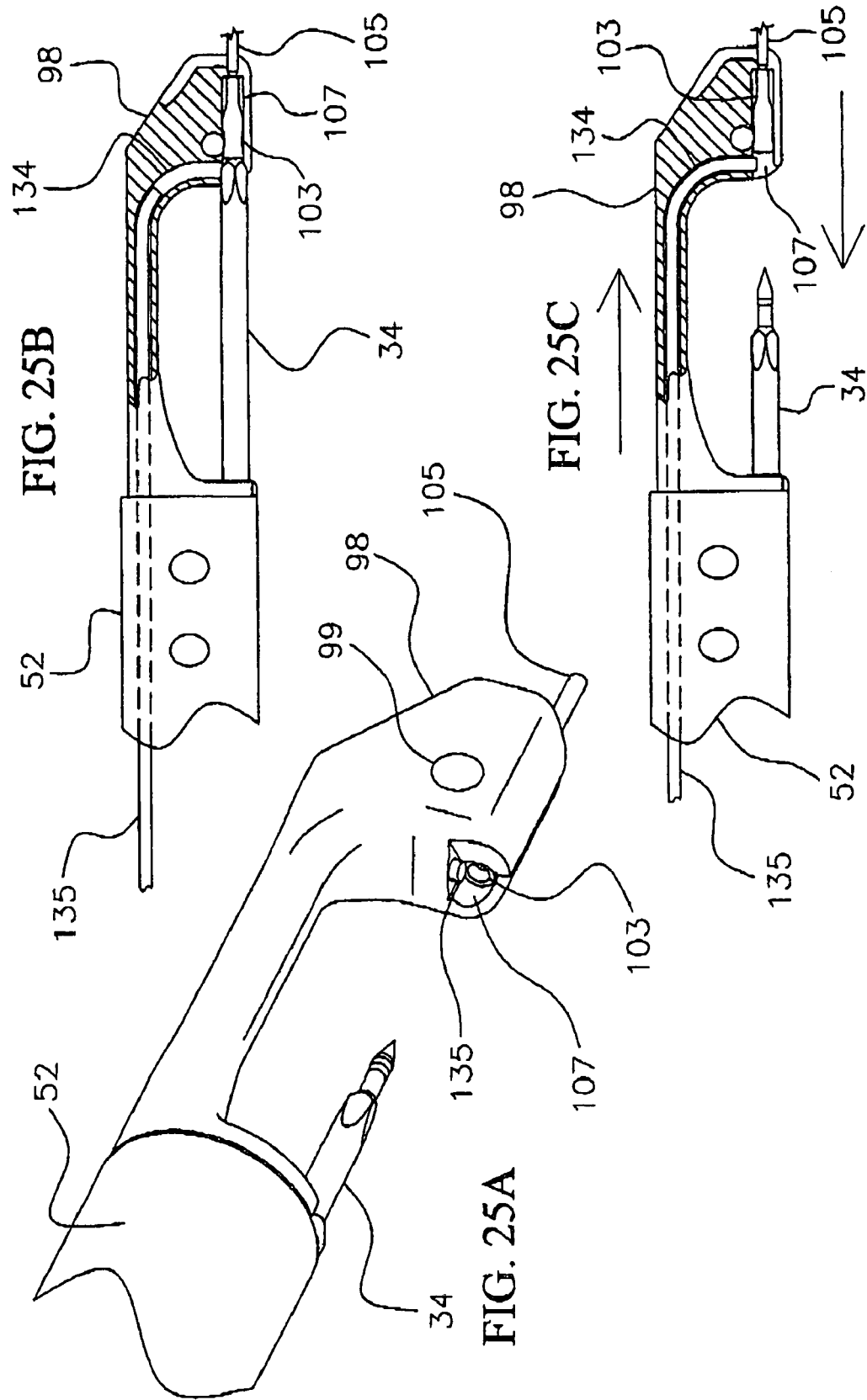

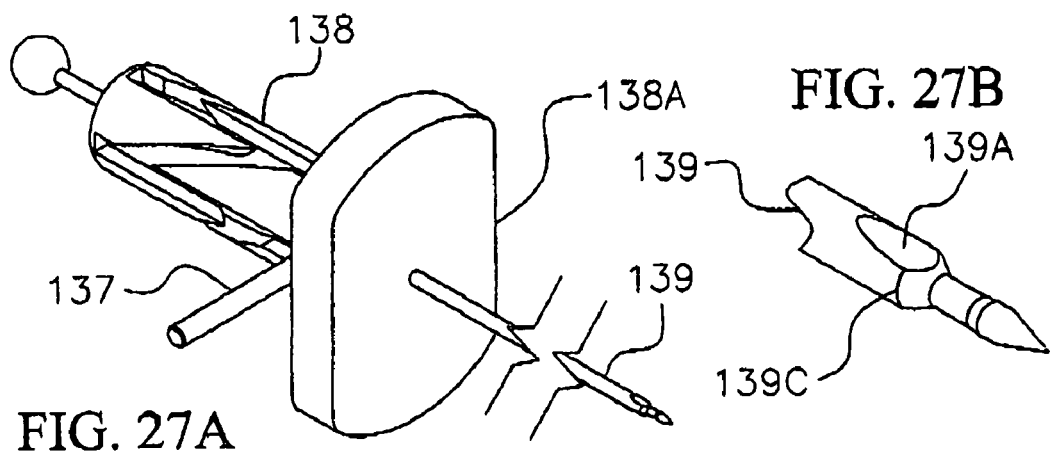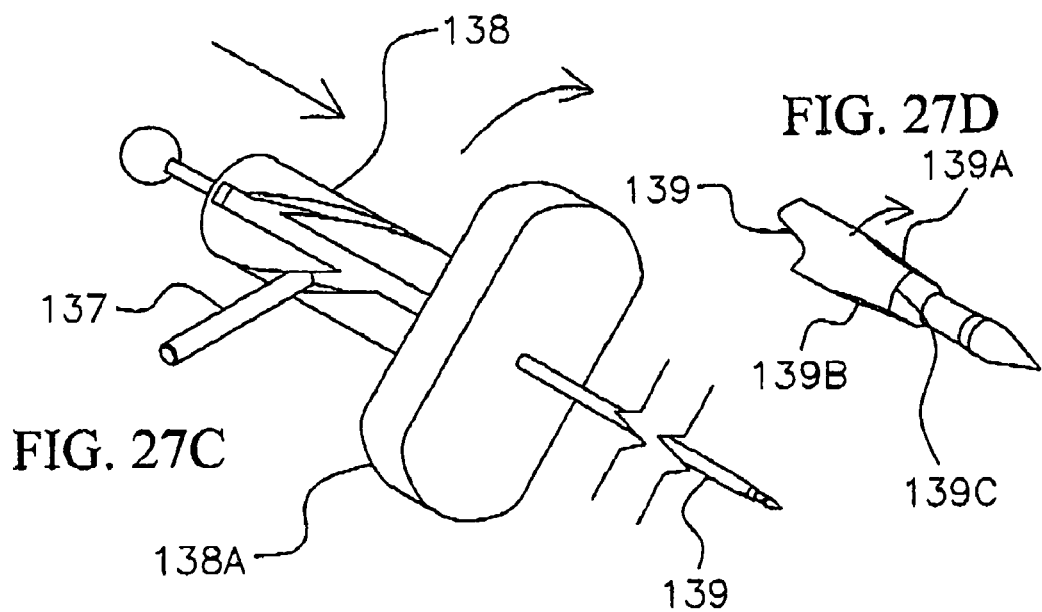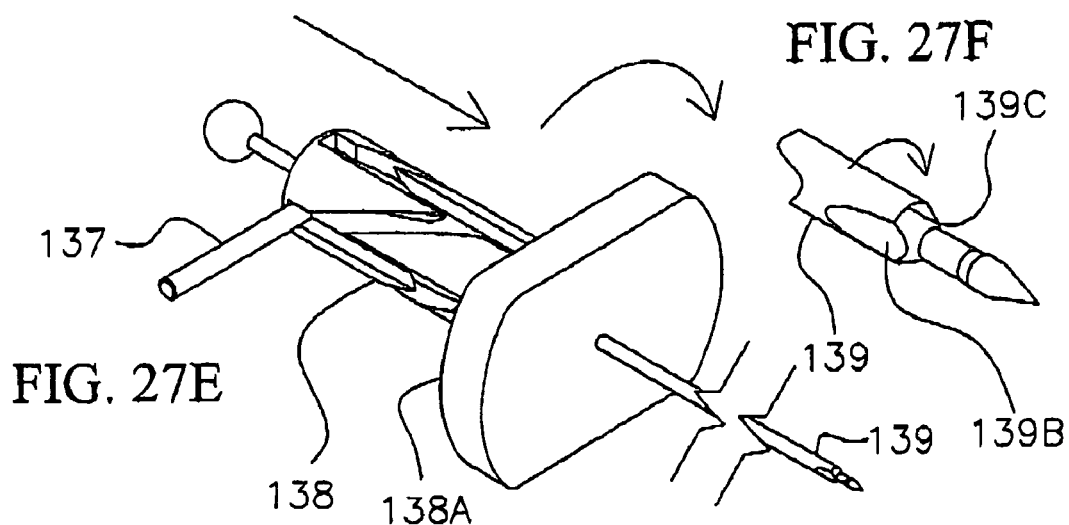

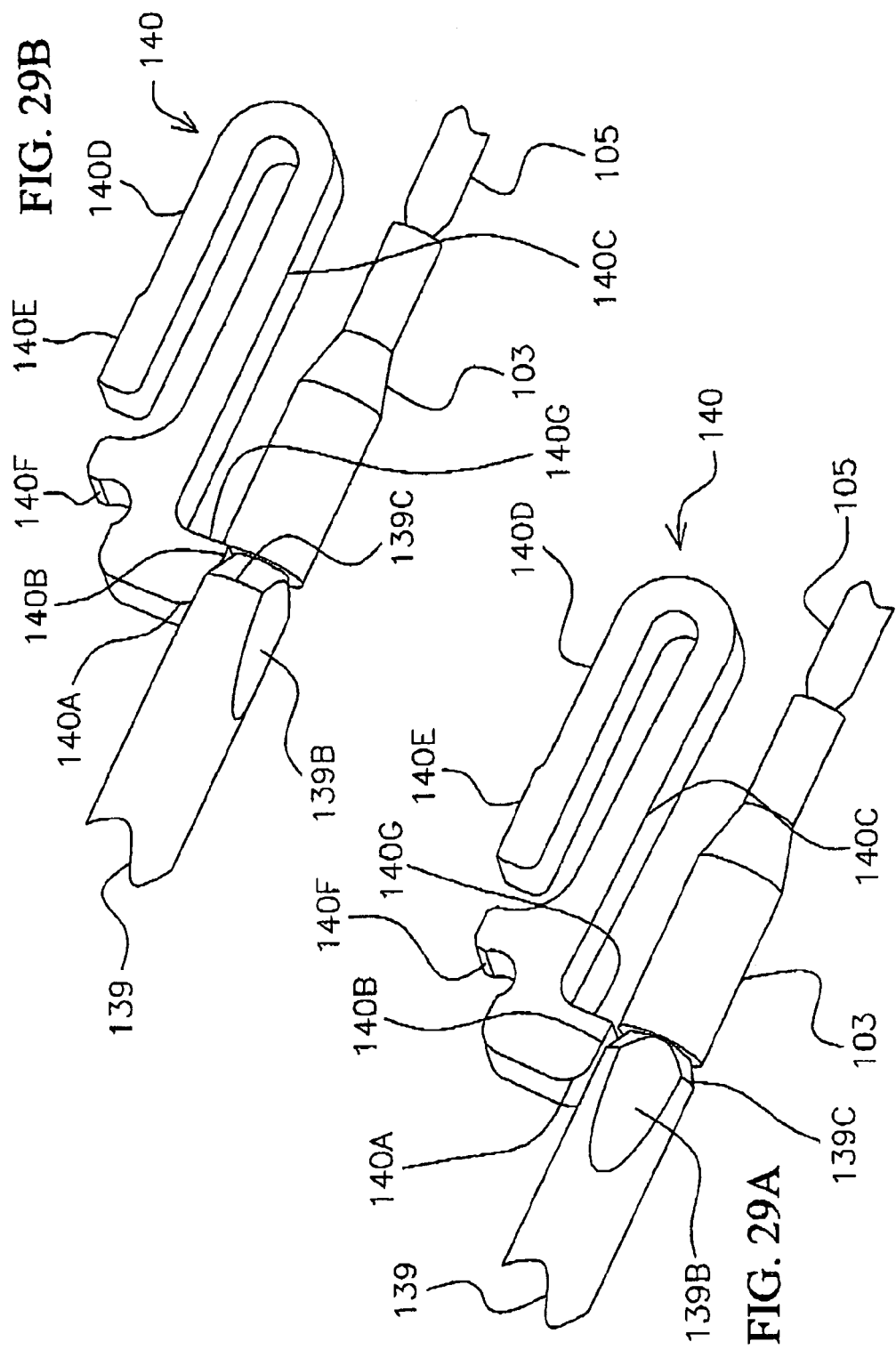

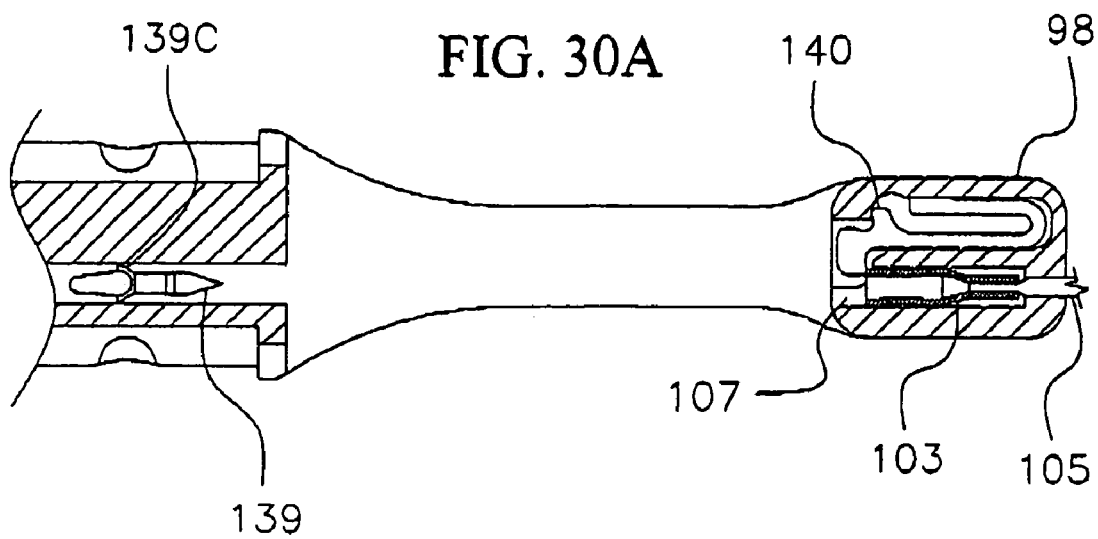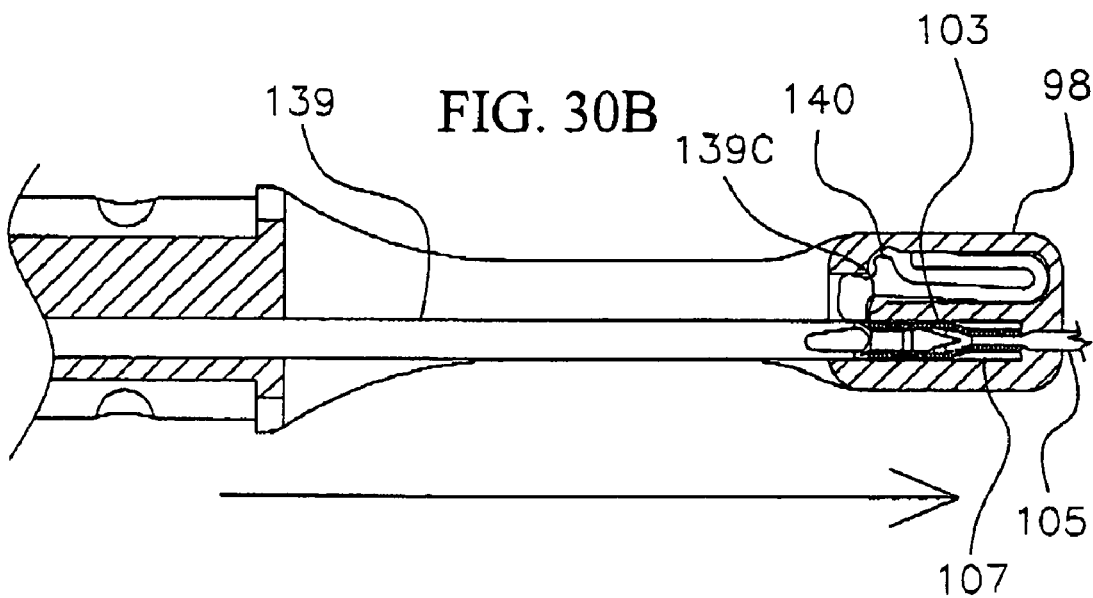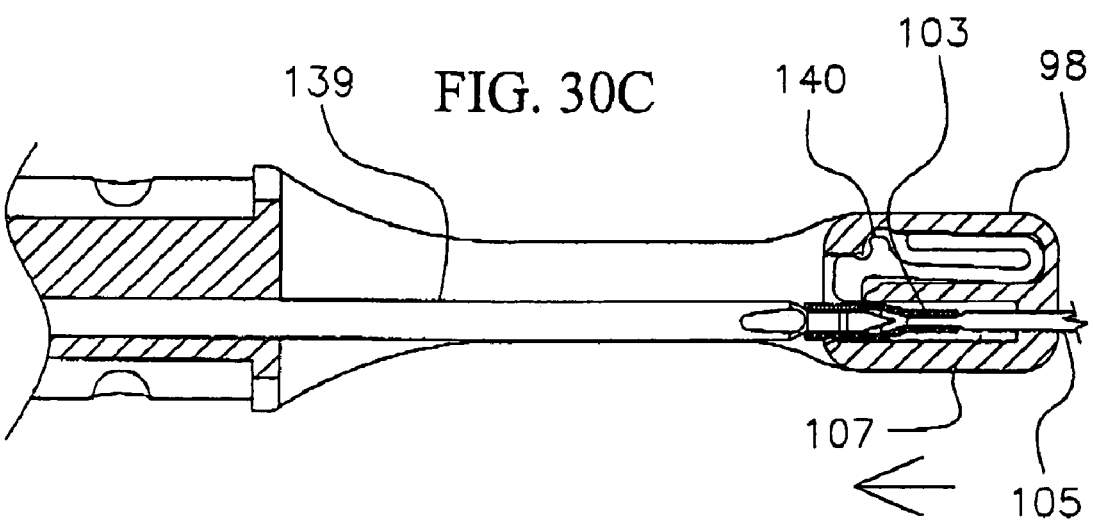

SEW-RIGHT RUNNING STITCH INSTRUMENT

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

This invention relates generally to surgical suturing instruments and more particularly to a surgical suturing instrument in which a needle can be selectively engaged with a fitting at the end of the suture for pulling the suture through a tissue section and released from the suture for permitting subsequent stitches to be made.

2. Description of Related Art

Invasive therapeutic interventions typically provide for the removal of problematic tissue structures from the body followed by a need to reconstruct the involved tissues. Many alternatives are available for reconstructive interventions. Bandages can often close external wounds. The use of sutures placed within wound edges to draw tissues together to permit enhanced healing has become commonplace in modern medicine. Metallic or plastic staples and clips also can be used to appose tissue for healing.

To minimize the invasiveness of therapeutic procedures, efforts to create smaller access wounds that minimize iatrogenic tissue disruption have lead to better patient outcomes. For example, a minimally invasive surgical procedure, like laparoscopic partial colonic resection with intestinal reconnection (anastomosis), can facilitate less peri-operative pain, more rapid return of normal functions, earlier return to home and work. The placement of sutures during laparoscopic surgery can be slow, tedious and often not successful. Existing specialized instruments for minimally invasive surgery (Sauer) have recognized limitations. An instrument to enable the rapid, precise placement of multiple suture bites with the same suture and then facilitate rapid, secure knot creation would be a significant advance.

BRIEF SUMMARY OF THE INVENTION

Briefly stated and in accordance with certain presently preferred embodiments of the invention, a surgical suturing instrument includes an elongated shaft, a tissue engaging gap formed in an end of the shaft, a needle reciprocally movable across the gap from a proximal end of the gap to a distal end of the gap, the needle having a ferrule engaging tip and a ferrule receiving aperture at a distal end of the gap for selectively holding and releasing a ferrule so that in a first mode the needle engages the ferrule and draws the suture across the gap and in a second mode, the ferrule is retained in the aperture and the needle separates from the ferrule and is retracted across the gap leaving the ferrule in the aperture.

In accordance with another aspect of the invention, a surgical suturing instrument for placing multiple suture loops in tissue comprises on elongated shaft, a reciprocal suture pick up member mounted on the shaft, a suture holder engaged by the reciprocating suture pick up member for selectively coupling a suture to the pick up member for drawing the suture through a first tissue section and releasing the suture from the pick up member for repeated coupling and drawing the suture through a second tissue section spaced from the first tissue section.

In accordance with another aspect of the invention, a surgical suturing instrument includes reciprocating tissue penetrating member, a suture holder, and apparatus for alternately coupling the reciprocating tissue penetrating member to the suture holder for drawing a length of suture through a tissue section and releasing the reciprocating tissue penetrating member from the suture holder.

In accordance with another aspect of the invention, a method of closing a wound includes the steps of disposing a suture on one side of a tissue section proximal to the wound, passing a needle through the section of tissue proximal to the wound, capturing the suture with the needle, drawing the suture through the section of tissue, releasing the suture from the needle, and repeating the passing capturing drawing and releasing steps.

In accordance with another aspect of the invention, a method of securing a suture at a wound site comprises passing an end of the suture through bolster and securing the suture with a bolster disposed between the end of the suture and the wound.

BRIEF DESCRIPTION OF THE SEVERAL VIEWS OF THE DRAWING(S)

The foregoing objects, features and advantages of the invention will become more apparent from a reading of the following description in connection with the accompanying drawings, in which:

FIGS. 4A–4C are perspective views of the thumb slide holder of FIG. 3 showing this component from the top left, top right and bottom right perspectives, respectively;

FIG. 5A is a partially exploded perspective view of the thumb slide mechanism of FIG. 3 highlighting the thumb button and the retaining lock features;

FIG. 5B is a perspective view of an assembled thumb slide mechanism of FIG. 3 showing the thumb button in its fully out position;

FIG. 6A is a left perspective view of the thumb slide mechanism of FIG. 3 with its balled needle fully back and its accompanying lever fully out;

FIG. 6B is a left perspective view of the thumb slide mechanism of FIG. 3 with its balled needle fully forward and its accompanying lever fully retracted;

FIG. 7A is a right perspective view of the thumb slide mechanism of FIG. 3 with its thumb button and ferrule stripper fully back and its accompanying lever fully out;

FIG. 7B is a right perspective view of the thumb slide mechanism of FIG. 3 with it thumb button and ferrule stripper fully forward and its accompanying lever fully retracted;

FIG. 8A is an exploded perspective view of the distal tip of the instrument of FIG. 1 showing the distal tube, jaw, needle, ferrule stripper and ferrule retainer;

FIG. 8B is a perspective view of the underside of the distal tip of FIG. 1 showing the ferrule stripper alignment ramp and the ferrule holding compartment;

FIG. 9A is a right perspective view of the drive mechanism of the instrument of FIG. 3 with the thumb slide holder removed and both the thumb button and the lever are fully out;

FIG. 9B is a right perspective view of the distal tip of the components of FIG. 9A showing the ferrule in its compartment;

FIG. 9C is a partial cross-sectional view of the distal tip of the components of FIG. 9A with the ferrule in its compartment and the needle and ferrule stripper fully back;

FIG. 9E is a right perspective view of the drive mechanism of the instrument of FIG. 3 with its thumb slide holder removed, the lever partially retracted and the thumb button fully out;

FIG. 9F is a right perspective view of the distal tip of the components of FIG. 9E with the needle partially advanced and the ferrule in its compartment;

FIG. 9G is the partial cross-sectional view of the distal tip of the components of FIG. 9E showing the ferrule in its compartment, the needle partially advanced and the ferrule stripper fully back;

FIG. 9J is a right perspective view of the drive mechanism of the instrument of FIG. 3 with the thumb slide holder removed, the lever fully retracted and the thumb button fully out;

FIG. 9K is a right perspective view of the distal tip of the components of FIG. 9J showing the needle fully advanced and engaging the ferrule in its compartment;

FIG. 9L is a partial cross-sectional view of the distal tip of the components of FIG. 9J with the needle engaging the ferrule in its compartment and the ferrule stripper fully back;

FIG. 10A is a right perspective view of the drive mechanism of the instrument of FIG. 3 with the thumb slide holder removed, with the thumb button fully out, the lever partially forward and the needle attached to the ferrule and suture partially back;

FIG. 10B is a right perspective view of the distal tip of the components of FIG. 10A showing the needle attached to the ferrule with suture partially retracted;

FIG. 10C is a partial cross-sectional view of the distal tip of the components of FIG. 10A showing the needle attached to the ferrule and suture partially retracted and the ferrule stripper fully back;

FIG. 10E is a right perspective view of the drive mechanism of the instrument of FIG. 3 with the thumb slide holder removed, the lever fully out and the thumb button fully out;

FIG. 10F is a right perspective view of the distal tip of the components of FIG. 10E showing the needle attached to the ferrule and suture fully retracted and the ferrule stripper fully back;

FIG. 10G is a perspective side view of the distal tip of the components of FIG. 10E showing the needle attached to the ferrule and suture fully retracted and the ferrule stripper fully back;

FIG. 10H is a side view of the proximal components of FIG. 10E showing the lever fully out and the thumb button fully out;

FIG. 11A is a right perspective view of the drive mechanism of the instrument of FIG. 3 with the thumb slide holder removed, the lever partially retracted, the needle with its ferrule and suture partially advanced and the thumb button fully out;

FIG. 11B is a right perspective view of the distal tip of the components of FIG. 11A showing the needle attached to the ferrule and the suture partially advanced;

FIG. 11C is a partial cross-sectional view of the distal tip of the components of FIG. 11A showing the needle attached to the ferrule and the suture partially advanced and the ferrule stripper fully back;

FIG. 11E is a right perspective view of the drive mechanism of the instrument of FIG. 3 with the thumb slide holder removed and the lever fully retracted and the thumb button fully out;

FIG. 11F is a right perspective view of the distal tip of the components of FIG. 11E with the needle fully advanced along with its attached ferrule and suture;

FIG. 11G is a partial cross-sectional view of the distal tip of the components of FIG. 11E showing the needle along with its attached ferrule and suture fully advanced into the ferrule compartment;

FIG. 11H is a side view of the proximal components of FIG. 11E showing the lever fully retracted and the thumb button fully out;

FIG. 11J is a close-up side view of the lock features of the components of FIG. 11H showing the flat engagement surface of the actuating member raising the proximal spring lock to disengage it from the timing tube;

FIG. 12A is a right partial view of the drive mechanism of the instrument of FIG. 3 with the thumb slide holder removed, the lever fully retracted, the needle with its attached ferrule and suture fully advanced and the thumb button partially advanced;

FIG. 12B is a right perspective view of the distal tip of the components of FIG. 12A showing the needle with its ferrule and suture fully advanced into the ferrule compartment and the ferrule stripper partially advanced;

FIG. 12C is a partial cross-sectional view of the distal tip of the components of FIG. 12A showing the needle attached to the ferrule and suture fully advanced and the ferrule stripper partially advanced;

FIG. 12D is a side view of the proximal components of FIG. 12A showing the lever fully retracted and the thumb button partially forward;

FIG. 12E is a close-up side view of the lock features of the components of FIG. 12D showing the flat engagement surface of the actuating member raising the proximal spring lock and the timing tube partially forward;

FIG. 12F is a right perspective view of the drive mechanism of the instrument of FIG. 3 with the thumb slide holder removed, the lever fully retracted, the needle with its attached ferrule and suture fully advanced, and the thumb button and ferrule stripper fully forward;

FIG. 12G is a right perspective view of the distal end of the components of FIG. 12F showing the needle with its ferrule and suture fully advanced and the ferrule stripper fully advanced and engaging the ferrule;

FIG. 12H is a partial cross-sectional view of the distal tip of the components of FIG. 12F showing the needle attached to the ferrule and the suture and the ferrule stripper fully advanced engaging the ferrule;

FIG. 12J is the side view of the proximal components of FIG. 12F showing both the lever and the thumb button fully forward;

FIG. 12K is a close-up side view of the lock features of FIG. 12J showing the flat engagement surface of the actuating member raising the proximal spring lock, the timing tube fully forward and engaging the released distal spring lock;

FIG. 13A is a right perspective view of the drive mechanism of the instrument of FIG. 3 with the thumb slide holder removed, the lever partially released, the needle partially retracted, the ferrule stripper engaging the ferrule in its ferrule compartment and the thumb button fully forward;

FIG. 13B is a right perspective view of the distal tip of the components of FIG. 13A showing the needle partially retracted and the ferrule stripper fully forward;

FIG. 13C is a partial cross-sectional view of the distal tip of the components of FIG. 13A showing the needle partially retracted and the ferrule stripper fully forward engaging the ferrule in its compartment;

FIG. 13D is a side view of the proximal components of FIG. 13A showing the lever partially out and the thumb button fully forward;

FIG. 13E is a close-up side view of the lock features of FIG. 13D showing the convex engagement surface of the actuating member raising the distal spring lock and the thumb button released but still fully forward;

FIG. 13F is a right perspective view of the drive mechanism of the instrument of FIG. 3 with the thumb slide holder removed, the lever, needle, thumb button and ferrule stripper partially back;

FIG. 13G is a right perspective view of the distal tip of the components of FIG. 13F with the needle and ferrule stripper partially retracted and the ferrule back into its compartment;

FIG. 13H is a partial cross-sectional view of the distal tip of the components of FIG. 13F showing the needle and the ferrule stripper partially back and the ferrule and suture in the ferrule compartment;

FIG. 13J is a side view of the proximal components of FIG. 13F showing the lever and the thumb button partially back;

FIG. 13K is a close-up side view of the lock features of FIG. 13F showing the engagement surfaces of the actuating member not raising either of the spring locks;

FIG. 13L is a right perspective view of the drive mechanism of the instrument of FIG. 3 with the thumb slide holder removed, the lever, needle, thumb button and ferrule stripper fully back and the ferrule and suture reloaded into the ferrule compartment;

FIG. 13M is a perspective view of the distal tip of the components of FIG. 13L showing the needle and ferrule stripper fully retracted and the ferrule and suture in the ferrule compartment;

FIG. 13N is a partial cross-sectional view of the distal tip of the components of FIG. 13L showing the needle and ferrule stripper fully back and the ferrule and suture in the ferrule compartment;

FIG. 13P is a side view of the proximal components of FIG. 13L showing the lever and the thumb button fully back;

FIG. 13R is a close-up side view of the lock features of FIG. 13L showing the proximal spring clip engaging the timing tube;

FIGS. 14A–14E show an example of the suturing procedure using the tissue suturing instrument of FIG. 1 for placement of suture at the first site of the wound closure;

FIGS. 15A–15E show an example of the suturing procedure using the tissue suturing instrument of FIG. 1 for placement of suture at the second site of the wound closure;

FIGS. 16A–16D show an example of the suturing procedure using the tissue suturing instrument of FIG. 1 for placement of suture at the third site of the wound closure;

FIGS. 17A–17D show an example of the suturing procedure using the tissue suturing instrument of FIG. 1 for placement of suture at the fourth site of the wound closure;

FIGS. 18A–8E show an example of the use of the instrument of FIG. 1 to enable suture loop construction to initiate the tying of a suture knot;

FIGS. 19A–19F show an example of the instrument of FIG. 1 to construct further suture loops used to secure a suture knot;

FIGS. 23A–23D illustrate a running suturing procedure created using the tissue suturing instrument of FIG. 1 being secured by bolsters and a crimped sleeve member;

FIG. 24A is a perspective view of the distal tip of the second preferred embodiment of the tissue suturing instrument of FIG. 1 in which a stripper wedge causes a flexible member to grasp the ferrule;

FIG. 24B is a partial cross-sectional view of the distal tip of the second preferred embodiment of the tissue suturing instrument of FIG. 1 showing the needle engaging the ferrule and partial deployment of the stripper wedge;

FIG. 24C is a partial cross-sectional view of the distal tip of the second preferred embodiment of the tissue suturing instrument of FIG. 1 showing the stripper wedge engaging the flexing member which grasps the ferrule and allows the needle to retract leaving the ferrule in its ferrule compartment;

FIG. 25A is a perspective view of the distal tip of the third preferred embodiment of the tissue suturing instrument of FIG. 1 in which a stripper rod passes through the distal tip and engages the proximal face of the ferrule to enable stripping;

FIG. 25B is a broken-out section of the distal tip of the third preferred embodiment of the tissue suturing instrument of FIG. 1 in which a stripper rod rests in its internal chamber as the needle engages the ferrule in its ferrule pocket;

FIG. 25C is a broken-out section of the distal tip of the third preferred embodiment of the tissue suturing instrument of FIG. 1 in which the stripper rod protrudes from its internal chamber to engage the proximal face of the ferrule as the needle disengages the ferrule and retracts;

FIG. 27A is a close-up isometric view of the cam and follower mechanism of the fourth preferred embodiment of the tissue suturing instrument of FIG. 1 illustrating the needle fully retracted;

FIG. 27B is a close-up perspective view of the tip of faceted needle of the fourth preferred embodiment of the tissue suturing instrument of FIG. 1 shown in its ferrule engaging configuration;

FIG. 27C is a close-up isometric view of the cam and follower mechanism of the fourth preferred embodiment of the tissue suturing instrument of FIG. 1 illustrating the needle partially advanced and the follower mechanism actuating the cam and rotating the needle;

FIG. 27D is a close-up perspective view of the tip of faceted needle shown partially rotated as it is advancing;

FIG. 27E is a close-up isometric view of the cam and follower mechanism of the fourth preferred embodiment of the tissue suturing instrument of FIG. 1 illustrating the needle fully advanced;

FIG. 27F is a close-up perspective view of the tip of faceted needle of the fourth preferred embodiment of the tissue suturing instrument of FIG. 1 shown fully advanced and rotated to its ferrule stripping configuration;

FIG. 29A is a close-up perspective view of the stripping mechanism of the fourth preferred embodiment of the tissue suturing instrument of FIG. 1 showing the ferrule latch disengaged and allowing the faceted needle to retrieve the ferrule;

FIG. 29B is a close-up perspective view of the stripping mechanism of the fourth preferred embodiment of the tissue suturing instrument of FIG. 1 showing the ferrule latch engaged and enabling the stripping of the faceted needle from the ferrule;

FIG. 30A is a partial cross-sectional view of the distal tip of the fourth preferred embodiment of the tissue suturing instrument of FIG. 1 showing the faceted needle fully retracted and the ferrule in its ferrule compartment;

FIG. 30B is a partial cross-sectional view of the distal tip of the fourth preferred embodiment of the tissue suturing instrument of FIG. 1 showing the faceted needle fully extended, disengaging the ferrule latch, and connecting with the ferrule in its ferrule compartment;

FIG. 30C is a partial cross-sectional view of the distal tip of the fourth preferred embodiment of the tissue suturing instrument of FIG. 1 showing the faceted needle beginning to retract with its attached ferrule and suture;

DETAILED DESCRIPTION OF THE INVENTION

Figure 1:
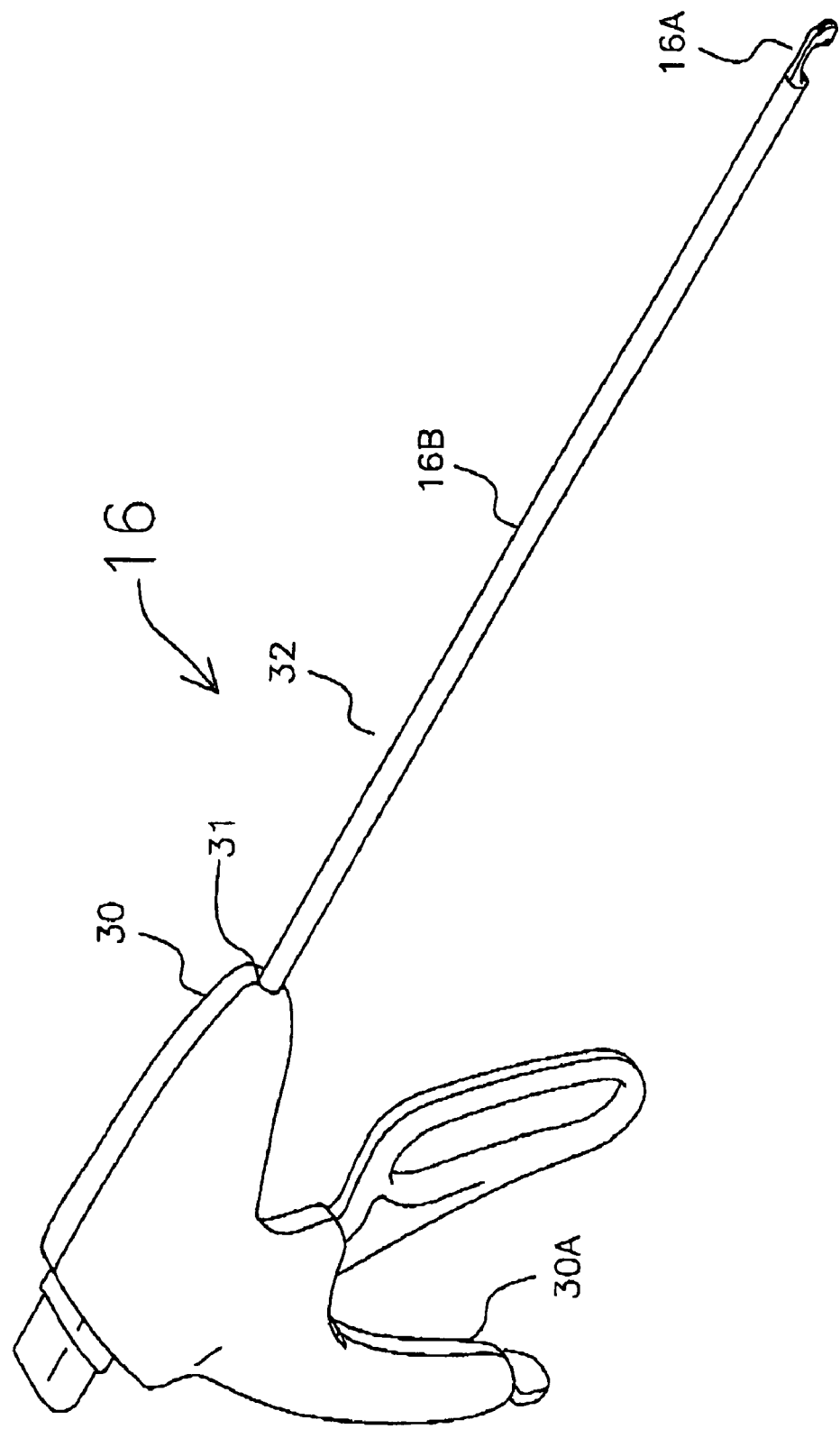
FIG. 1 is a perspective view of the tissue suturing instrument in accordance with the present invention.
Figure 2:
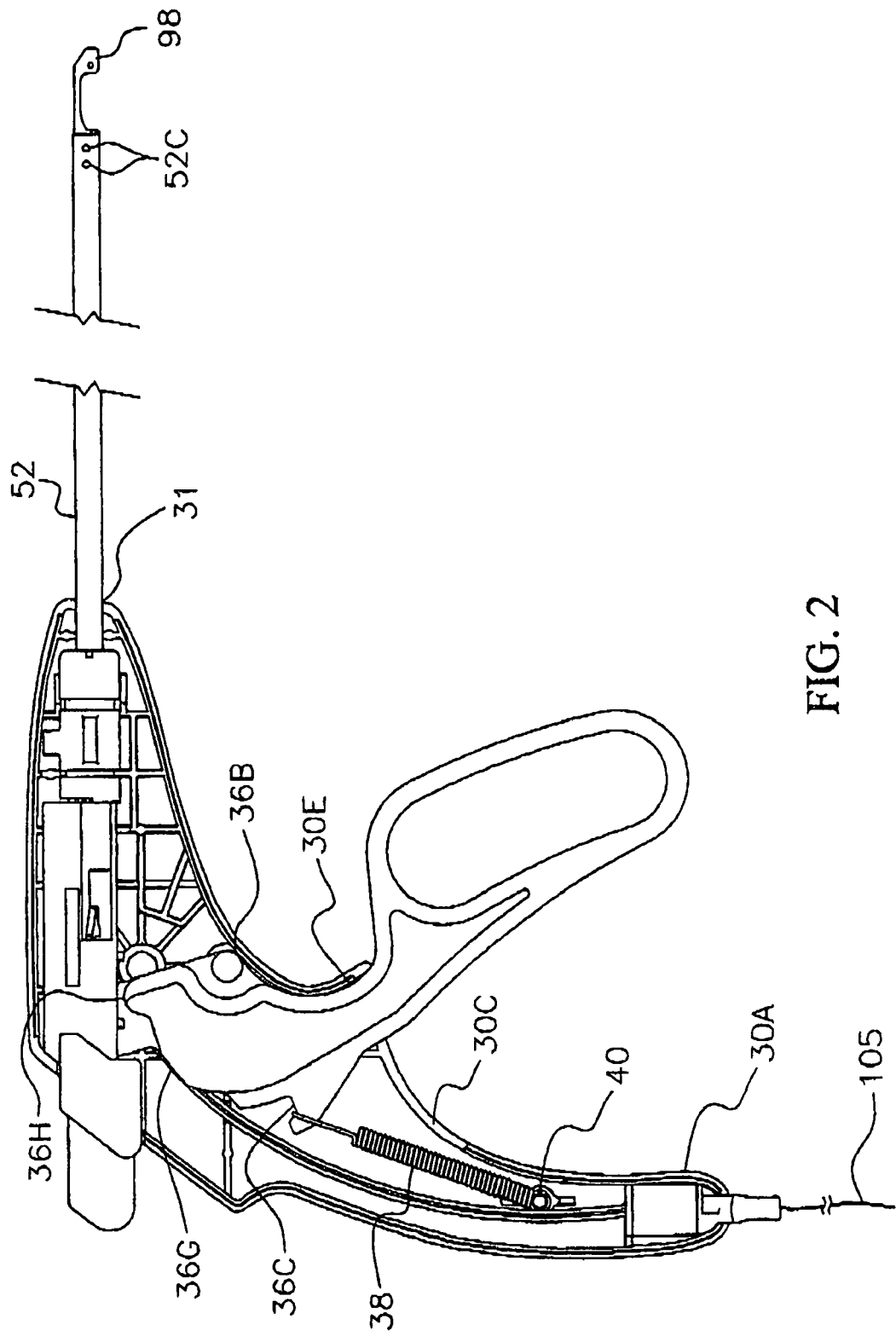
FIG. 2 is a partial side view of the tissue suturing instrument of FIG. 1 in which the right cover of the housing of the instrument is removed.
Figure 3:
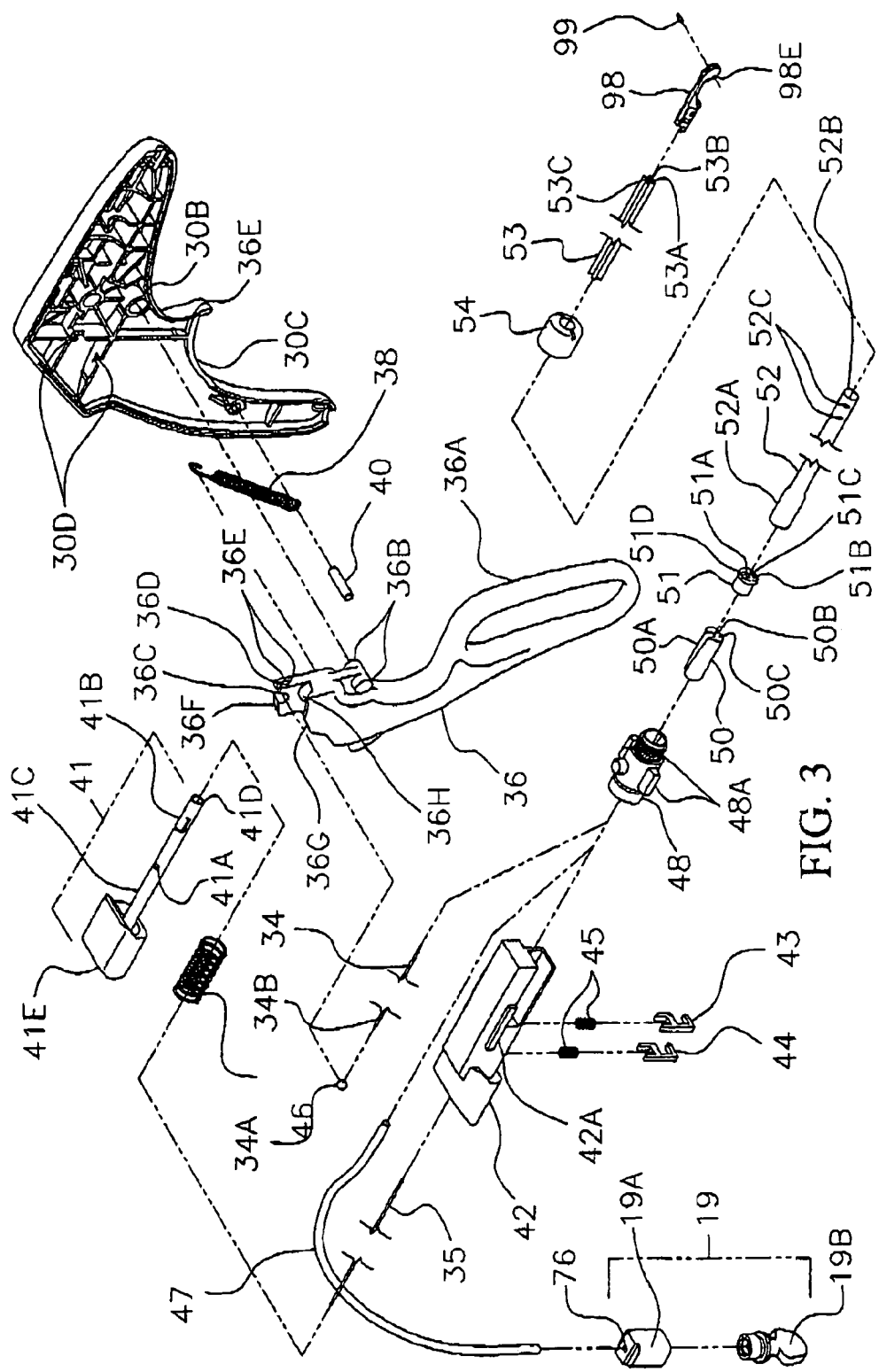
FIG. 3 is an exploded perspective view of the tissue suturing instrument of FIG. 1 in which the right cover of the housing is removed.

The first preferred embodiment of this invention, suturing instrument 16, is represented in FIGS. 1–13R. Referring to FIGS. 1–3, show the suturing instrument 16, which represents the SEW-RIGHT® SR•5® manufactured by LSI SOLUTIONS, Inc. (formerly LaserSurge, Inc.) of Victor, N.Y., that has been modified to provide a means for selectably stripping its ferrule 103 from the needle 34 at its tissue engaging end 16a. The tissue engaging end 16a and needle 34 thereto may be similar to that shown in U.S. Pat. Nos. 5,431,666, 5,766,183, European Patent No. EP 0669101, filed Feb. 23, 1995 and granted Oct. 14, 1998, or U.S. patent application Publication No. US 2002/0107530 A1, filed Feb. 2, 2001, which are herein incorporated by reference.

The housing 30 has a body shaped like a pistol having a handle portion 30a, and may be made of a two-piece construction of molded plastic. A needle 34 extends from housing 30 through the shaft 16b into the tissue engaging end 16a. Needle 34 has a non-tissue engaging end 34b in the housing 30 having a spherical member 34a, such as a ball or bearing, respectively, attached thereto. The needle 34 and spherical member 34a may be made of metal, such as surgical stainless steel. The spherical member 34a may have a bore into which the non-tissue engaging end 34b of the needle 34 extends and joins thereto, such as by welding or brazing.

The suturing instrument 16 includes an actuating member 36 representing a lever 36a having two pins 36b extending into holes 30b in the sides of housing 30 upon which the actuating member 36 is pivotally mounted in the housing 30. Actuating member 36 has a portion which extends through a lever opening 30c (FIG. 2) in housing 30 to enable pivotal movement about pins 36b. An extension spring 38 is provided which hooks at one end in a notch 36c of actuating member 36 and is wound at the other end around a pin 40 located in holes 30f in the sides of housing 30, such that the actuating member 36 is spring biased to retain actuating member 36 normally in a forward position, fully out, as shown for example in FIG. 2. The body of housing 30 has a front pivot stop 30e (FIG. 3) providing a stop that limits the pivotal movement of the actuating member 36. A notch 36c is provided in the actuating member 36 which is shaped to receive the non-engaging end of needle 34, i.e., spherical member 34a, to be driven forward by an operator pulling actuating member 36 to pivot actuating member 36 towards handle portion 30a. The groove 36d (FIG. 3) is provided by two fingers 36e into which the needle 34 near the spherical member 34a may lie.

As shown in FIGS. 4B and 4C, a thumb slide holder 42 is fixed in housing 30 by two flanges 42a above actuating member 36. As best shown in FIG. 4A, the thumb slide holder 42 has a chamber 42b with a groove 42d formed by fingers 42e which allow the needle 34 to be received in chamber 42b to restrict movement of the needle 34 when held therein. The lower surface 42f of thumb slide holder 42 is curved and faces correspondingly curved upper surface 36f of actuating member 36, such that the actuating member 36 is slidable along lower surface 42f responsive to the operator pulling the actuating member 36.

The adapter 48 has a bore extending there through in which a needle spreader 50 is located. Needle spreader 50 has two channels 50b and 50c into which needle 34 and ferrule stripper 35 are respectively located to increase the distance between the needle 34 and the ferrule stripper 35 as they extend toward thumb slide holder 42, such that the needle 34 and ferrule stripper 35 are properly aligned.

A suture routing tube 47 is provided for suture thread in housing 30. Suture routing tube 47 has one end received in a valve assembly 19, at the bottom of handle portion 30a of housing 30 and then extends through the suture routing tube notch 30d (FIG. 3) along the interior of the left side of housing 30, and a groove 50a along needle spreader 50 (FIG. 3). The other end of the suture routing tube 47 is then mounted in suture routing tube hole 51a through gasket 51. Gasket member 51 further has two holes 51b and 51c through which needle 34 and ferrule stripper 35, respectively extend. The gasket 51 may be made of medical grade rubber, such as Santoprene.

A longitudinal guide member 53 is provided multiple tracks along its length, including two tracks 53a and 53b for needle 34 and ferrule stripper 35, respectively, and a suture track 53c for suture 105 extending from opening 51a of gasket 51. The guide member 53 may be made of extruded flexible material, such as Tecoflex®. A D-tube 52 is provided which is D-shaped at one end 52a is registered into a corresponding shaped opening in adapter 48, and a threaded nut 54 having an opening which extends over D-tube 52, screws onto the end of the adapter 48 to secure D-tube 52 to housing 30. With the gasket 51 loaded first into D-tube 52, guide member 53 extends from the gasket 51 through the D-tube 52. In this manner, tracks 53a, 53b, and 53c each form a channel with the interior surface of D-tube 52. D-tube 52 may be made of stainless steel, or other rigid material, and has for example, D-tube 52 has an outside diameter of 0.203 inches. (Note for other applications, such as flexible endoscopy, this tube could be flexible.) Inside D-tube 52, gasket 51 has a ring 51d, which frictionally engages the interior surface of D-tube 52. Hole 51a of the gasket 51 is of a diameter such that the suture tube 47 tightly fits therein and provides a seal around suture tube 47. The suture tube 47 may be held in place in hole 51a by friction, but adhesive may also be used. Holes 51b and 51c are of a larger diameter than the needle 34, except for a small section of holes 51b and 51c where the diameter reduces to form flaps of gasket material which seal around needle 34 and ferrule stripper 35, respectively. This enables movement of the needle 34 and ferrule stripper 35 tube back and forth while maintaining a seal about the needle 34 and ferrule stripper 35. One feature of the gasket 51 is that it enables sealing the shaft 16b as well.

The guide member 53 is received into the D-tube 52, such that guide member 53 abuts gasket 51 and engages distal tip 98. Distal tip 98 is attached to the D-tube 52 by mechanical fastening by forming small dents 52c in the metal of the D-tube 52 with a press into recessed four pockets 98b (FIG. 3), i.e., two on each side of the distal tip 98.

An optional valve assembly 19 can be provided at the bottom of handle portion 30a, as shown in FIG. 3, having a valve seat 19a and a valve controller 19b. Valve seat 19a is composed of medical grade rubber, such as Santoprene®, and has a through hole extending into an interior chamber. A valve controller 19b composed of molded plastic, or other rigid material, has a circular section through an opening and a surface forming a cam that can be turned to select a valve fully open to intermediate partially open to a fully closed position. The suture routing tube 47 is received in hole 76 of valve seat 19a, as shown in FIG. 3, such that suture 105 material from the tube can pass through openings of the valve seat 19a and then through the valve controller 19b.

Referring to FIGS. 2 and 3, the tissue engaging end 16a of the suturing instrument 16 is shown having the distal tip 98 which is mounted in a D-tube 52, such that the front section 98a of the distal tip 98 extends from D-tube 52.

Referring to FIGS. 4A–4C, the thumb slide holder 42 is shown. The thumb slide holder 42 may be made of a one-piece construction of molded plastic. The thumb slide holder 42 is fixed in the housing 30 above the actuating member 36 by two opposing flanges 42a, as best shown in FIG. 4B.

As best represented in FIG. 4A, the thumb slide holder 42 has a chamber 42b through which the positive stop 41b of the timing tube 41c is located. One groove 42d formed by two fingers 42e allows the needle 34 (FIG. 3) to pass through the thumb slide holder 42 through the groove 36d formed by the two fingers 36e of the actuating member 36 and enables the spherical member 34a to rest in the notch 36c of the actuating member 36. The lower curved surface 42f extends over the curved upper surface 36f of the actuating member 36 to further retain the needle 34 and spherical member 34a in the notch 36c throughout the entire range of motion of the actuating member 36.

The housing 42g of the thumb slide holder 42 is fashioned to accommodate and guide the thumb button 41e (FIG. 3). The thumb button stop 42k serves as a motion-limiting surface to prevent the thumb button 41e from traveling farther than intended. The thumb slide holder 42 has a bore 42c for the timing tube 41c (FIG. 3) is located. Contained within the housing 42g is a raised region 42h to enable alignment of the return spring 46 (FIG. 3) and resting surface 42j which seats and retains the return spring 46.

FIG. 4C shows a perspective view of the thumb slide holder 42 and timing tube stop 42l which provides a positive engagement surface for the positive stop 41b to limit the advance of the timing tube 41c. The thumb slide holder 42 may further have a channel 42p forward of the groove 42d to provide clearance for suture routing-tube 47 (FIG. 3). The body of the thumb slide holder 42 has lock spring bores 42n and spring lock channels 42m to provide for the assembly, alignment, and retaining of the lock springs 45 and distal spring lock 43 and proximal spring lock 44, respectively and best represented in FIGS. 5A and 5B.

FIG. 5A shows the push button assembly 41 interfacing with other components. The timing tube 41c is shown with the thumb button 41e attached thereto. Housed inside the thumb button 41e is the return spring 46 which serves as a return mechanism for the assembly. The ferrule stripper 35 is received into the distal opening 41d and coupled to the timing tube 41c via an insert molding or adhesive process. The lock springs 45 are inserted into the thumb slide holder 42 and followed with the proximal spring lock 44 and the distal spring lock 43. With the proximal spring lock 44 and the distal spring lock 43 inserted in the thumb slide holder 42 and compressed, the push button assembly 41 with attached ferrule stripper 35 is inserted into the thumb slide holder 42 such that the positive stop 41b passes into the chamber 42b and the proximal spring lock engages in the spring lock engagement slot 41a. The ferrule stripper 35 continues through the adapter 48.

FIG. 5B shows a perspective view of the underside of assembled push button assembly 41, thumb slide holder 42, adapter 48, nut 54, and D-tube 52 and highlights the relative location of the proximal spring lock 44 and distal spring lock 43.

Referring to FIGS. 6A and 6B, the operation of the actuating member 36 and the needle 34 is described. As the actuating member 36 is engaged, rotating about the pins 36b, the needle 34 and the attached spherical member 34a are advanced as the spherical member 34a is in contact with the notch 36c of the actuating member 36.

FIGS. 7A and 7B illustrate the operation of the push button assembly 41 and the ferrule stripper 35. The actuating member 36 is engaged, rotating about the pins 36b until the flat engagement surface 36g comes into contact with and forces the proximal spring lock 44 out of the spring lock engagement slot 41a (FIG. 5A) allowing the forward motion of the push button assembly 41 and the coupled ferrule stripper 35. This forward motion is limited primarily by the engagement of distal spring lock 43 with spring lock engagement slot 41a (FIG. 5A). Advancement of timing tube 41c is also limited by engaging the adapter 48.

FIG. 8A shows the assembly of the distal tip 98 and the ferrule retainer 99 with the D-tube 52, the needle 34, and the ferrule stripper 35. The distal tip 98 has a gap 104 in a c-shaped jaw 104 having two openings 98c at one side of the gap through which each needle 34 and ferrule stripper 35 may extend The needle 34 and the ferrule stripper 35 are received into the needle/stripper openings of the distal tip 98 and the distal tip 98 is then coupled to the D-tube 52 which may be achieved by mechanical fastening forming small dents in the metal of the D-tube 52 with a press into four recessed pockets 98b, i.e., two on each side of the distal tip 98. The ferrule retainer 99 is inserted into the ferrule retainer hole 98e until the ring 99a seats into the opening created where the ferrule retainer hole 98e intersects the ferrule pocket 107 as best shown in FIG. 8B. The suture 105 attached to the ferrule 103 enters the ferrule compartment 107 through the open slot located on the side of the ferrule chamber opposite from the ferrule retainer 99.

FIGS. 9A–13R represent highlights of twelve sequential steps overviewing the loading, reloading and locking operations through one complete cycle of use of instrument 16. For example, the first three steps presented in FIGS. 9A–9M, illustrate the needle 34 first advancing into the ferrule 103.

Figure 9D:
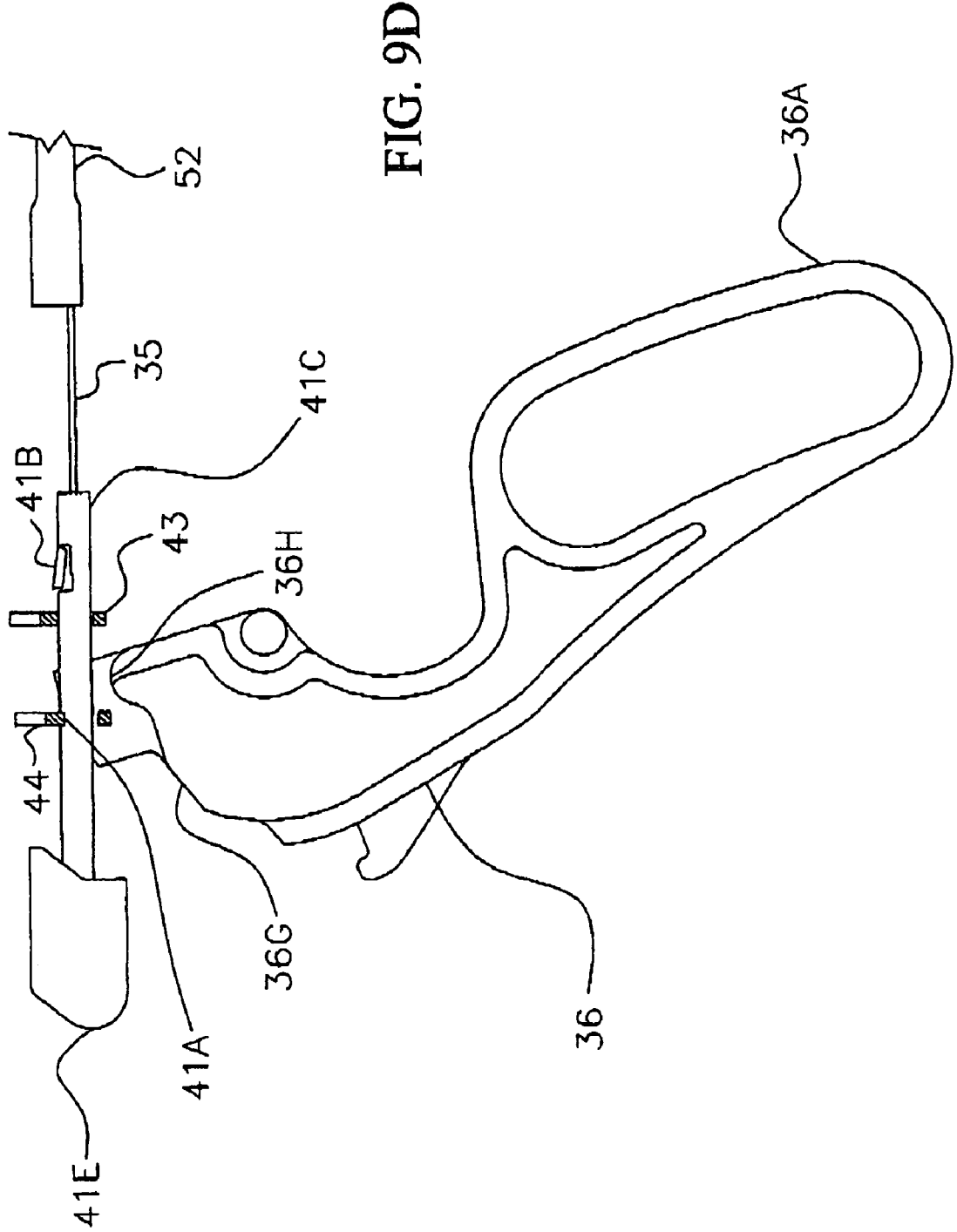
FIG. 9D is a side view of the proximal components of FIG. 9A showing the lever and thumb button fully out.

FIGS. 9A–9D show the instrument loaded and ready for use, the first step. FIG. 9A shows a right perspective view of the drive mechanism of the instrument of FIG. 3 with the thumb slide holder 42 removed and both the thumb button 41e and the lever 36a are fully out; the proximal spring lock 44 engages the timing tube 41c. FIG. 9B is a right perspective view of the distal tip 98 of the components of FIG. 9A showing the ferrule 103 in its ferrule compartment 107 and the jaw 104. FIG. 9C is a partial cross-sectional view of the distal tip 98 of the components of FIG. 9A with the ferrule 103 in its ferrule compartment 107, and the needle 34 and ferrule stripper 35 fully back. FIG. 9D is a side view of the proximal components of FIG. 9A showing the lever 36a and thumb button 41 fully out. Proximal spring lock 44 is shown engaging spring lock engagement slot 41a of timing tube 41c.

Figure 9H:
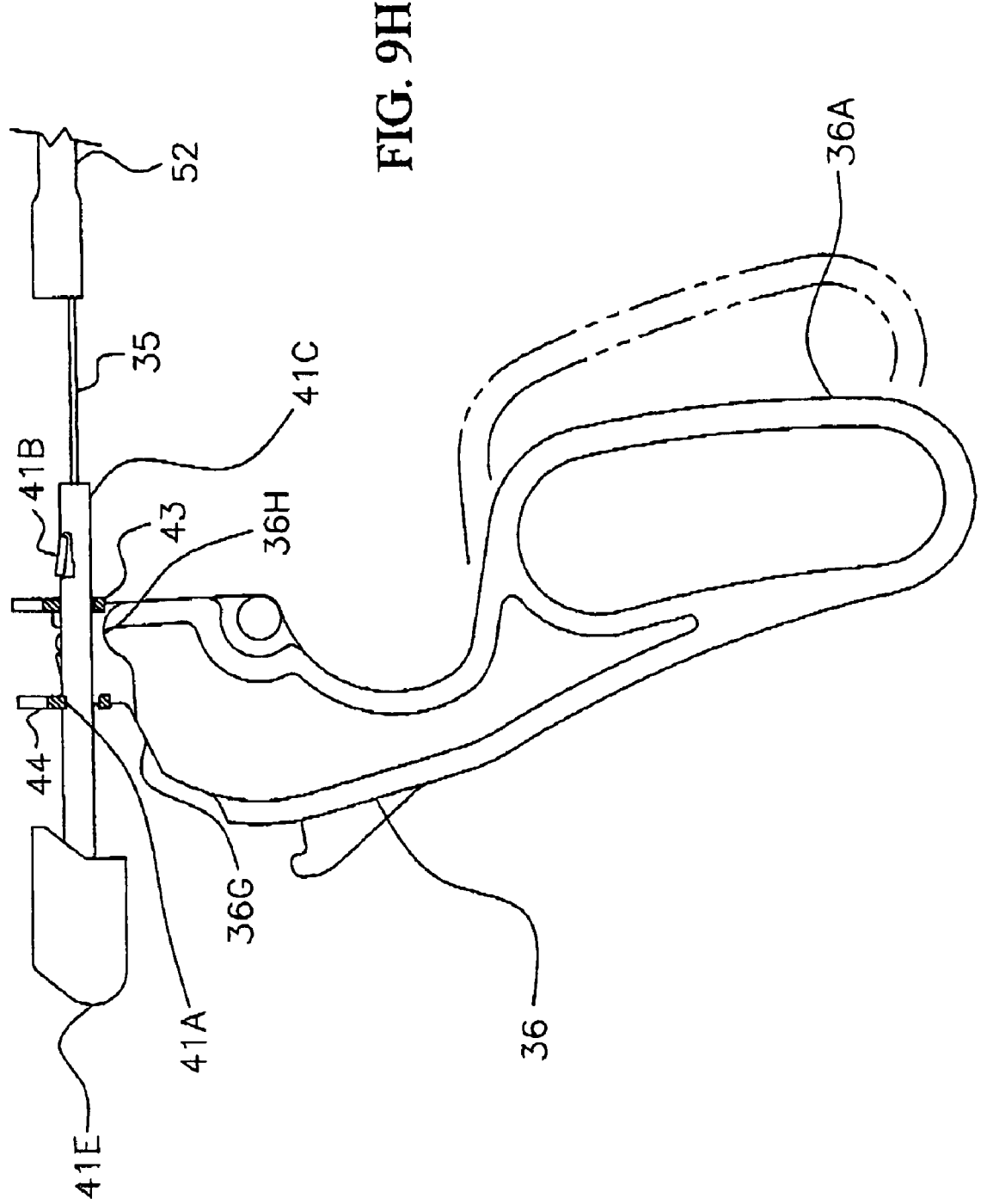
FIG. 9H is a side view of the proximal components of FIG. 9E showing the lever partially retracted and the thumb button fully out.

FIGS. 9E–9H show partial advancement of the needle 34 as part of the second step. FIG. 9E is a right perspective view of the drive mechanism of the instrument of FIG. 3 with its thumb slide holder 42 removed, the lever 36a partially retracted and the thumb button 41e fully out. FIG. 9F is a right perspective view of the distal tip 98 of the components of FIG. 9E with the needle 34 partially advanced and the ferrule 103 in its ferrule compartment 107. FIG. 9G is the partial cross-sectional view of the distal tip 98 of the components of FIG. 9E showing the ferrule 103 in its ferrule compartment 107, the needle 34 partially advanced and the stripper 35 fully back. FIG. 9H is a side view of the proximal components of FIG. 9E showing the lever 36a partially retracted and the thumb button 41e fully out.

Figure 9M:
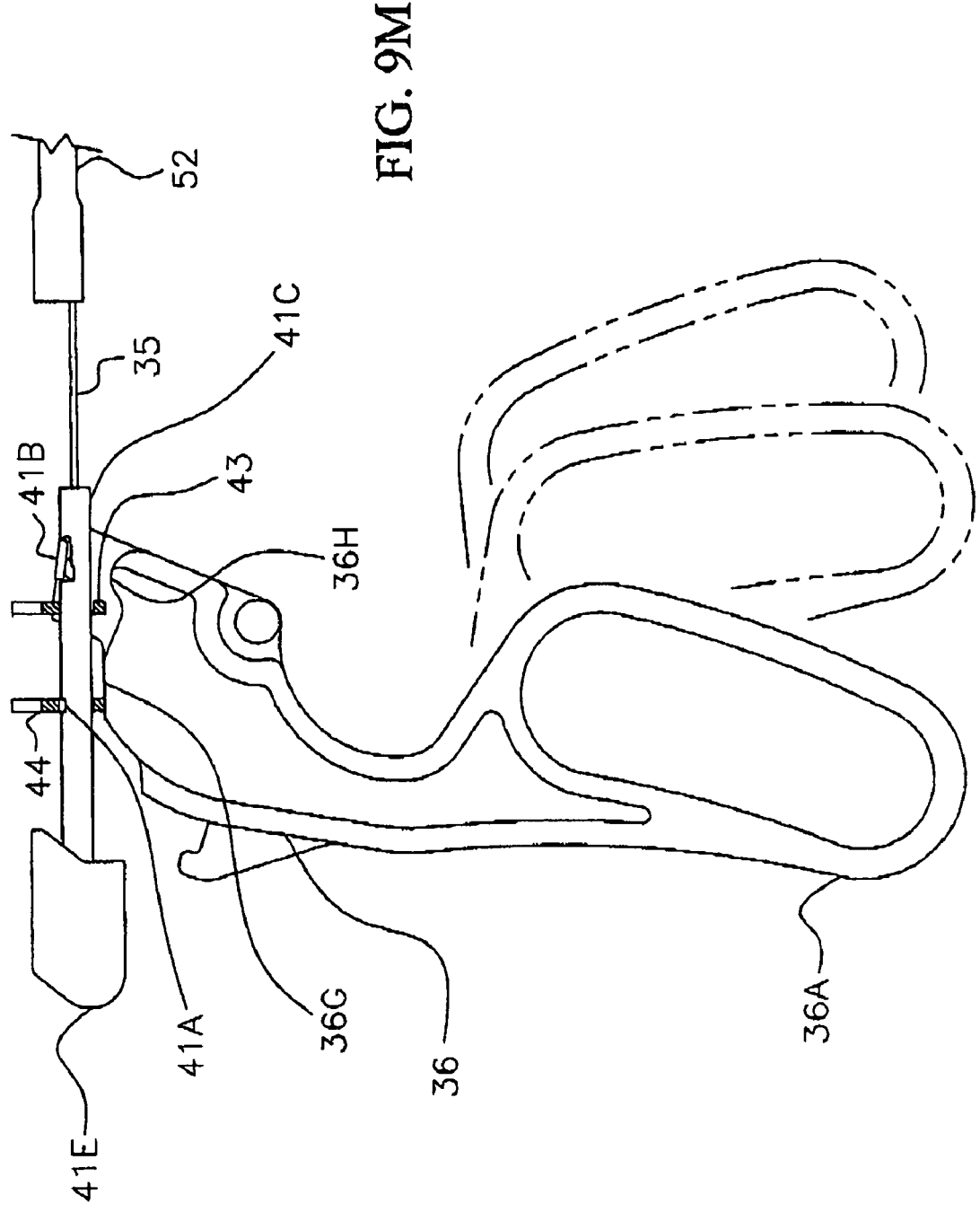
FIG. 9M is a side view of the proximal components of FIG. 9J showing the lever fully retracted and the thumb button fully out.

FIGS. 9J–9M show the needle 34 fully advanced and engaged inside of the ferrule 103 as part of the third step. FIG. 9J is a right perspective view of the drive mechanism of the instrument of FIG. 3 with the thumb slide holder 42 removed, the lever 36a fully retracted and the thumb button 41e fully out. FIG. 9K is a right perspective view of the distal tip 98 of the components of FIG. 9J showing the needle 34 fully advanced to engage the ferrule 103 in its ferrule compartment 107; best shown in FIG. 9L. FIG. 9L is a partial cross-sectional view of the distal tip 98 of the components of FIG. 9J with the needle 34 engaging the ferrule 103 in its ferrule compartment 107 and the ferrule stripper 35 fully back. FIG. 9M is a side view of the proximal components of FIG. 9J showing the lever 36a fully retracted and the thumb button 41e fully out. Note that the flat engagement surface 36g is shown raising the proximal spring lock 44 out of the spring lock engagement slot 41a.

Figure 10D:
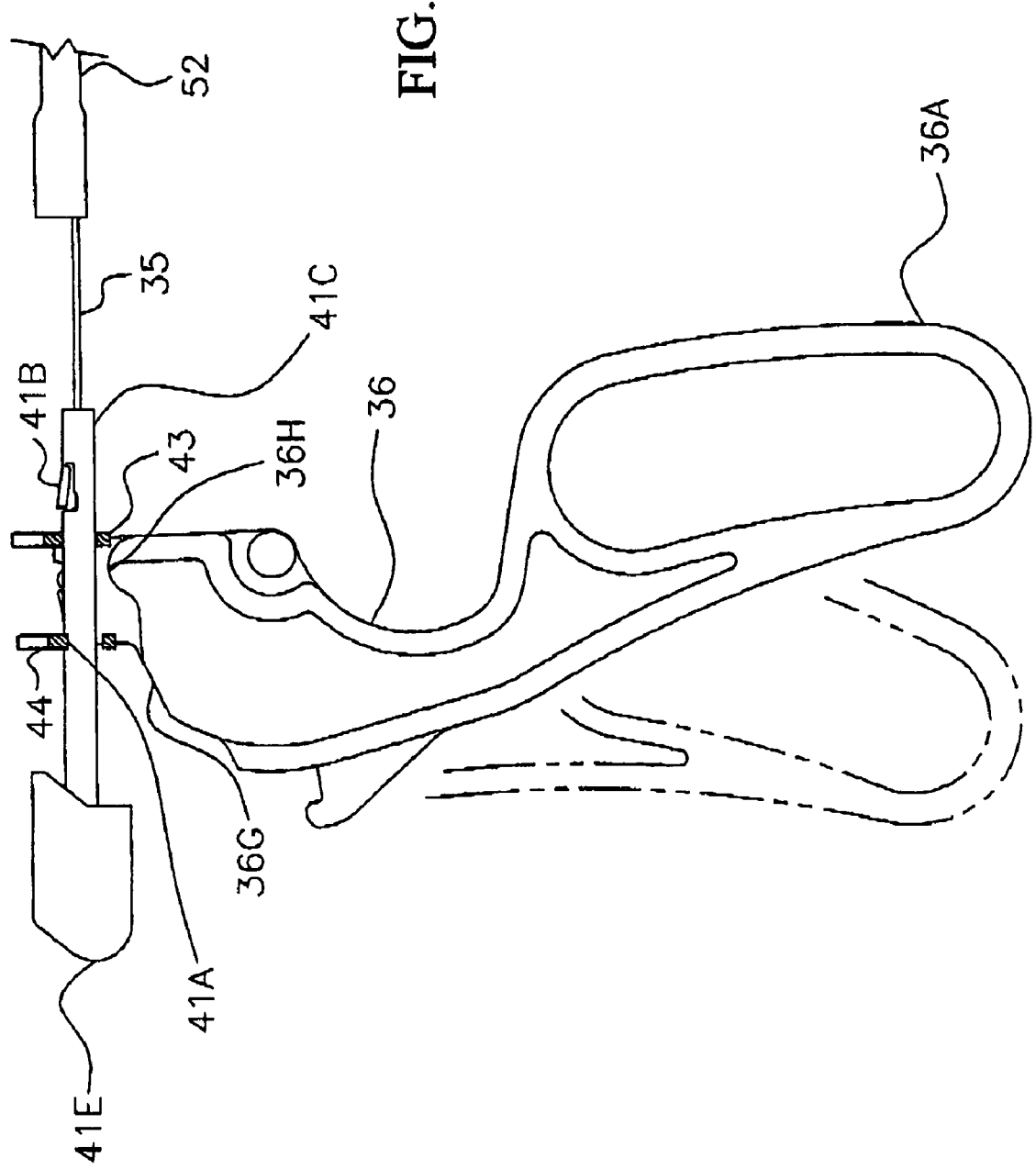
FIG. 10D is a side view of the proximal components of FIG. 10A showing the lever partially back and the thumb button fully out.

The next two steps presented in FIGS. 10A–10H, illustrate the needle 34, now attached to the ferrule 103 and its suture 105, being retracted fully back. FIGS. 10A–10D show the needle 34 pulling its ferrule 103 back through jaw 104. FIG. 10A is a right perspective view of the drive mechanism of the instrument of FIG. 3 with the thumb slide holder 42 removed, with the thumb button 41e fully out, the lever 36a partially forward and the needle 34 attached to the ferrule 103 and suture 105 partially back. FIG. 10B is a right perspective view of the distal tip 98 of the components of FIG. 10A showing the needle 34 attached to the ferrule 103 with suture 105 partially retracted. FIG. 10C is a partial cross-sectional view of the distal tip 98 of the components of FIG. 10A showing the needle 34 attached to the ferrule 103 and suture 105 partially retracted and the ferrule stripper 35 fully back. FIG. 10D is a side view of the proximal components of FIG. 10A showing the lever 36a partially back and the thumb button 41e fully out;

FIGS. 10E–10H show this instrument 16 with the ferrule 103 and its suture 105 attached to the fully retracted needle 34. FIG. 10E is a right perspective view of the drive mechanism of the instrument of FIG. 3 with the thumb slide holder 42 removed, the lever 36a fully out and the thumb button 41e fully out. FIG. 10F is a right perspective view of the distal tip 98 of the components of FIG. 10E showing the suture 105 fully retracted and the ferrule stripper 35 fully back. FIG. 10G is a perspective side view of the distal tip 98 of the components of FIG. 10E showing the needle 34 attached to the ferrule 103 and suture 105 fully retracted and the ferrule stripper 35 fully back. FIG. 10H is a side view of the proximal components of FIG. 10E showing the lever 36a fully out and the thumb button 41e fully out.

Figure 11D:
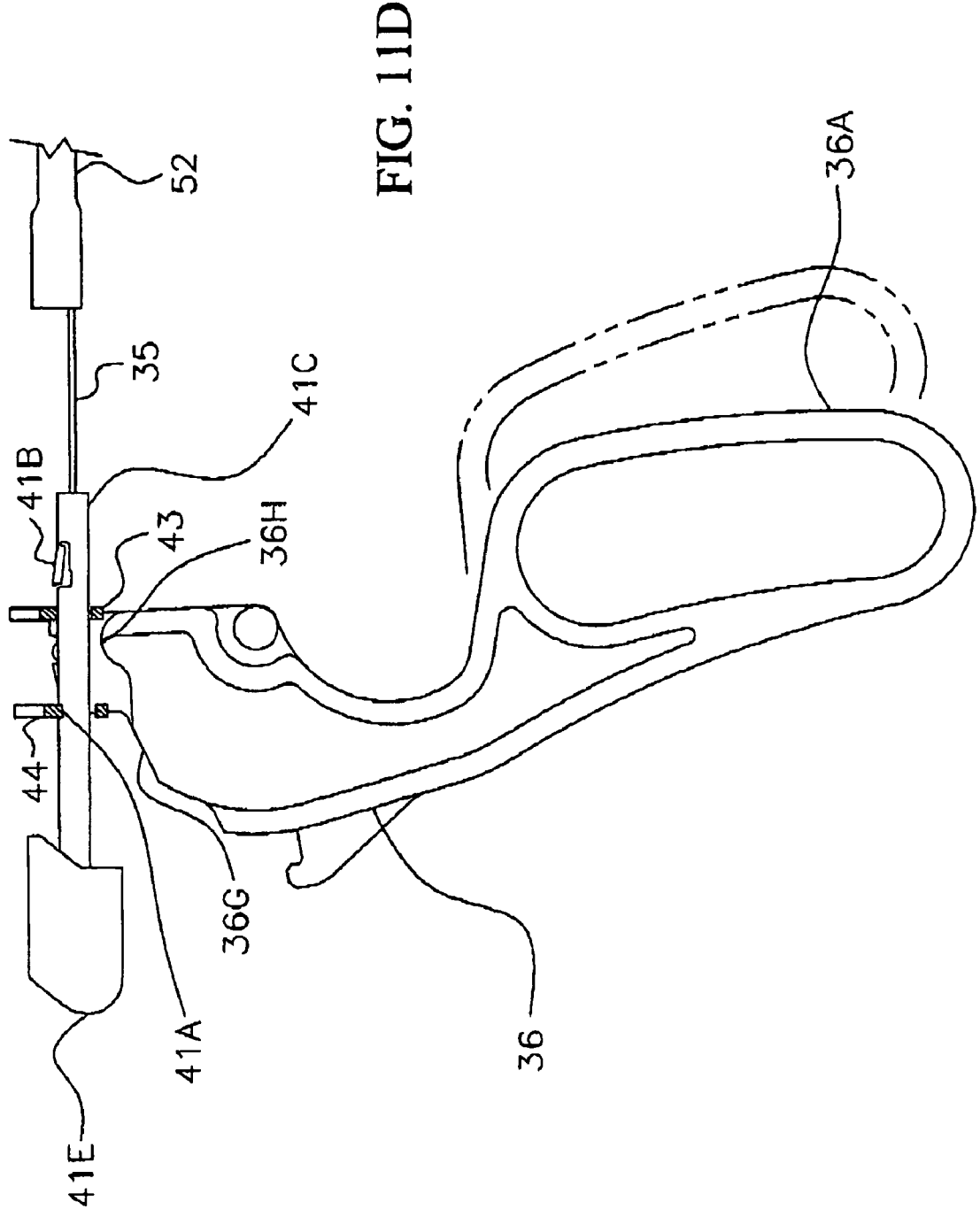
FIG. 11D is a side view of the proximal components of FIG. 11A showing the lever partially retracted and the thumb button fully out.
Figure 18D:
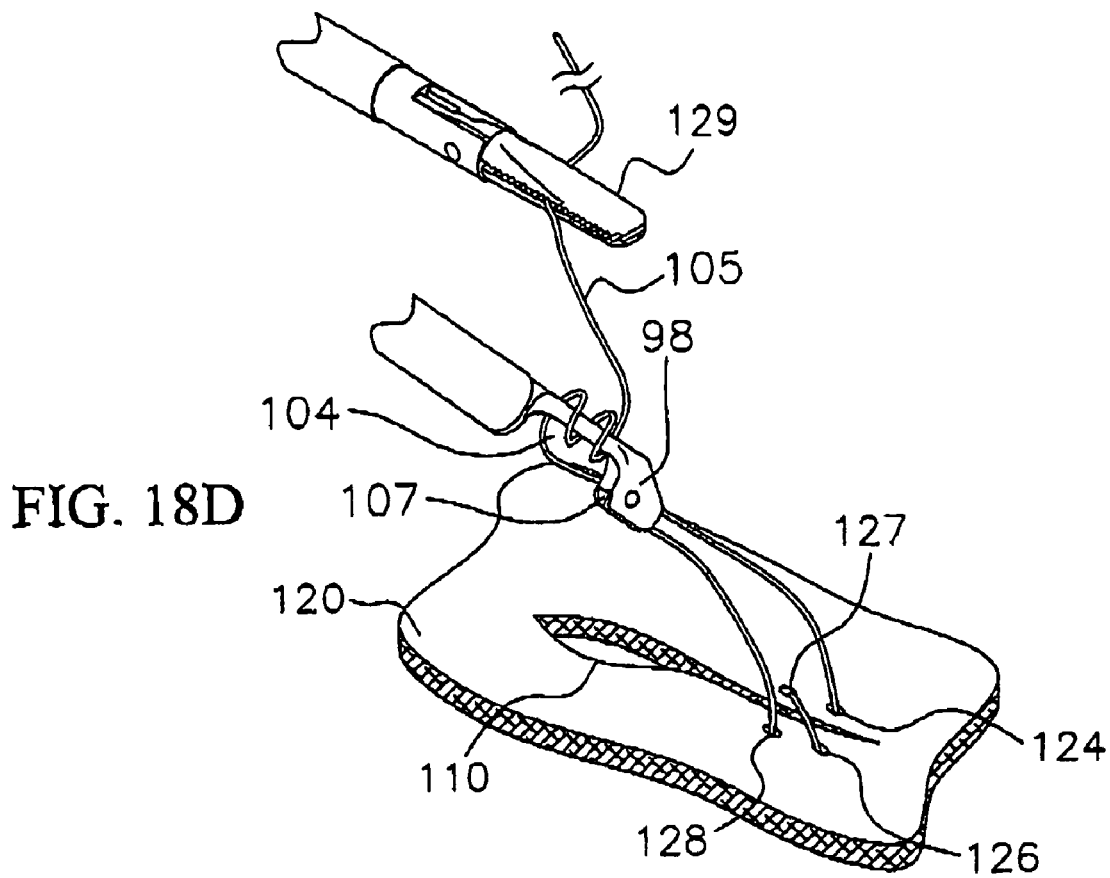
Figure 18E:
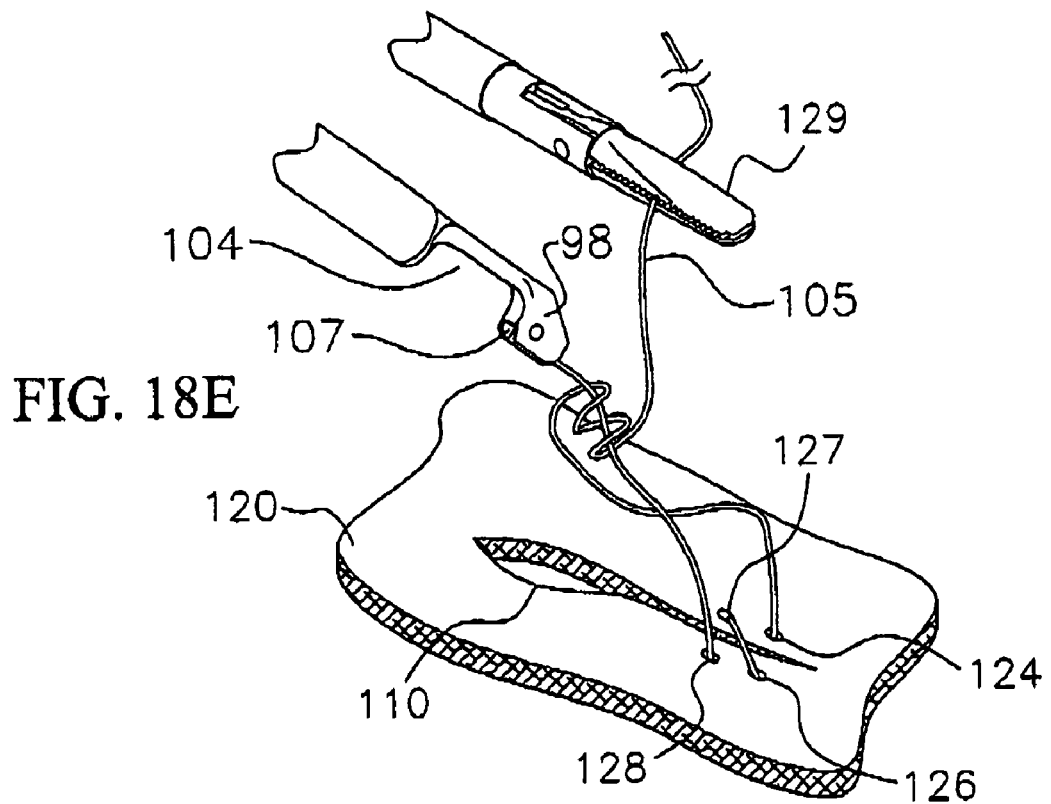
Figure 19A:
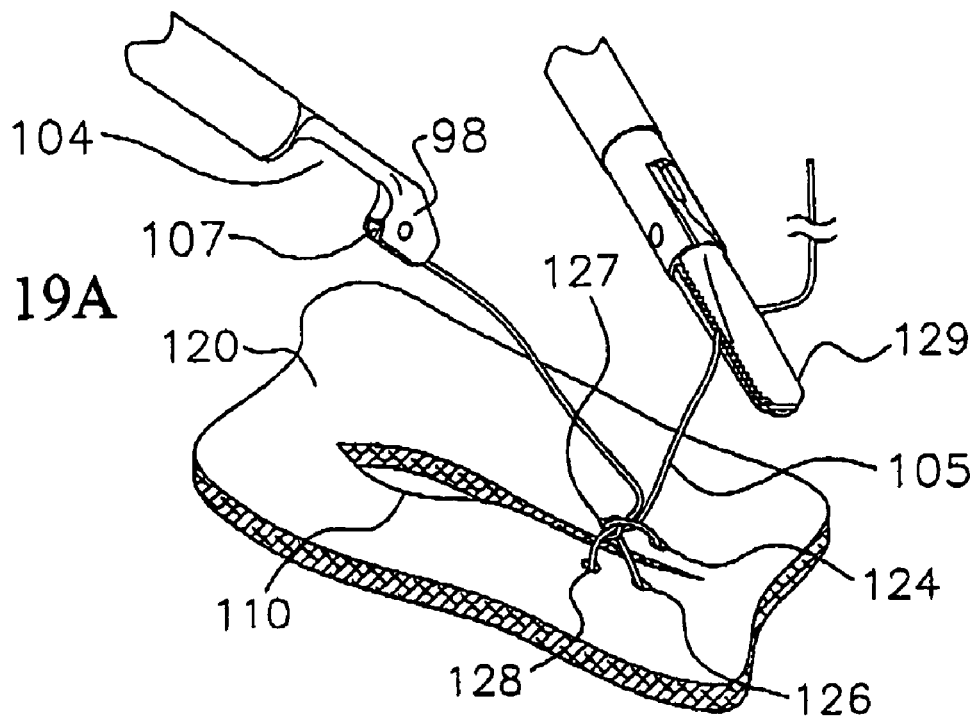
Figure 19B:
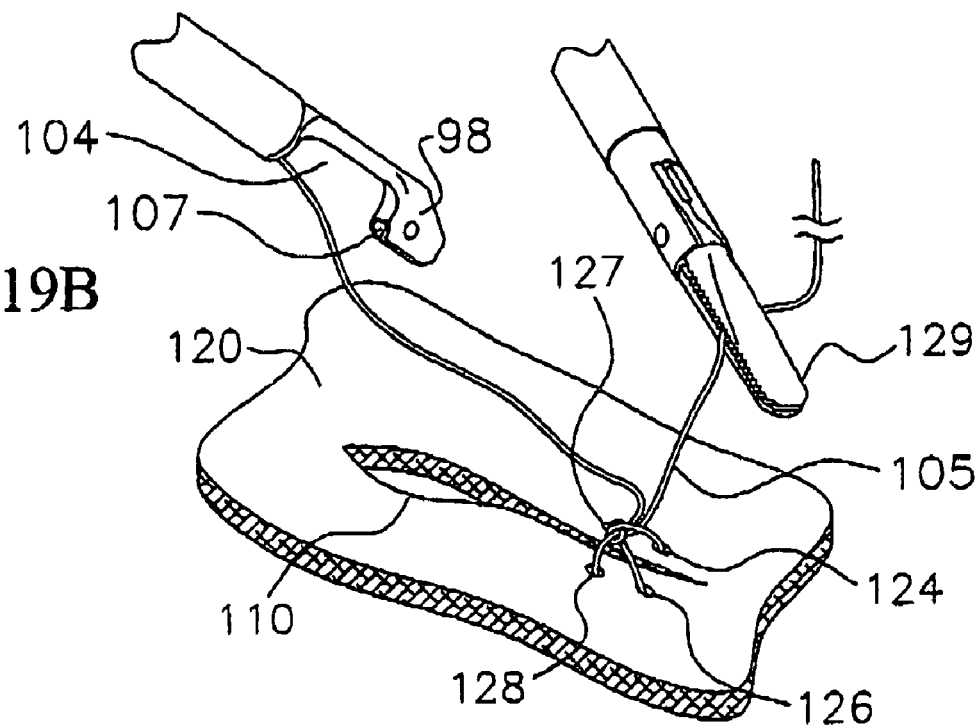
Figure 19E:
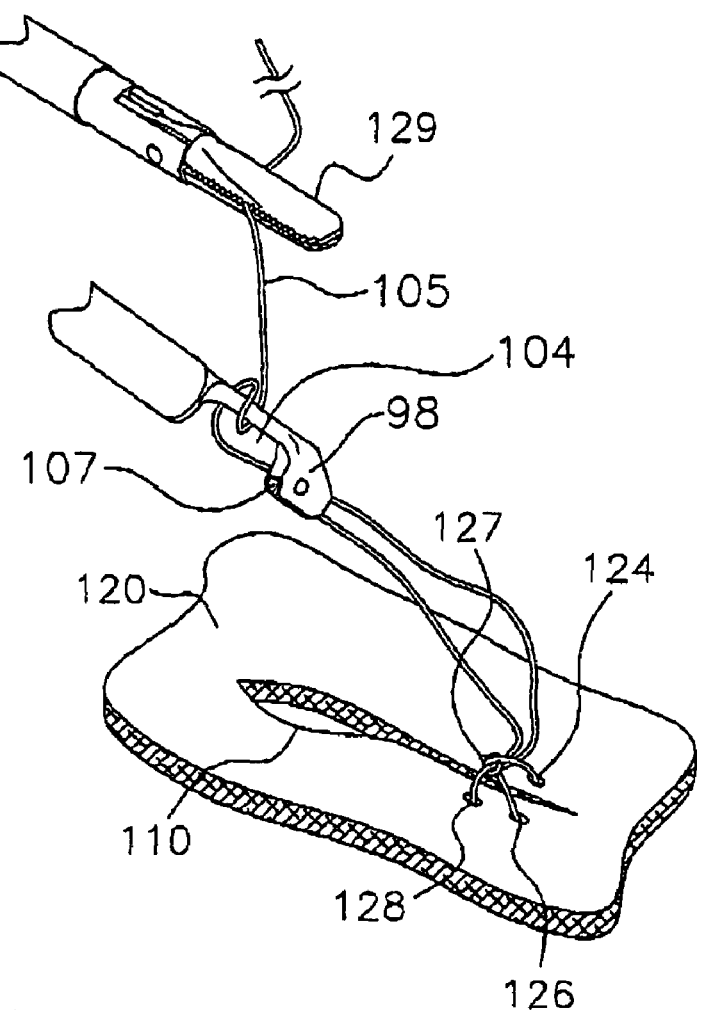
Figure 19F:
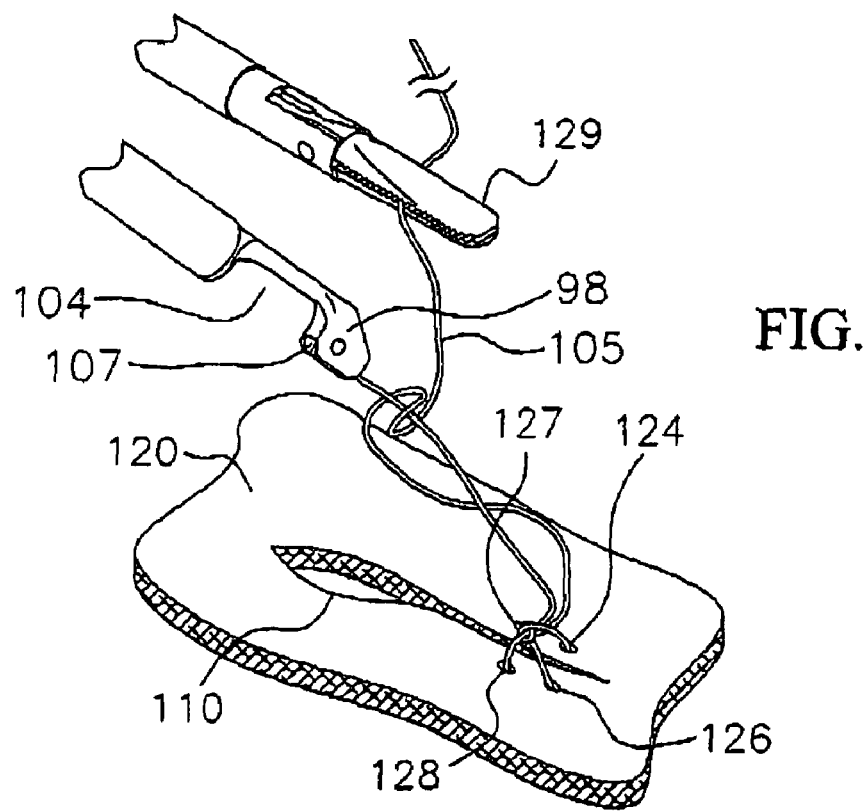
Figure 20:
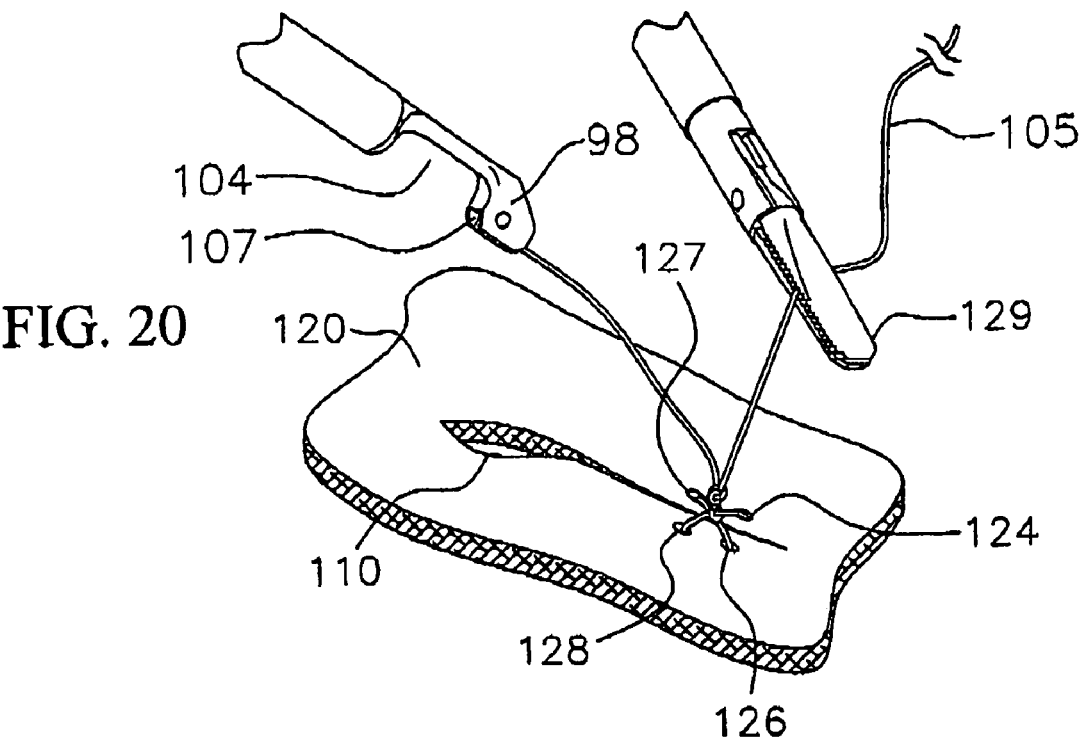
FIG. 20 shows the suturing instrument of FIG. 1 used with a surgical grasper, which pulls on the free end of the suture to deliver the suture knot to the wound closure site.

FIGS. 11A–11J show the next two steps representing reinsertion of the ferrule 103 into it ferrule compartment 107. FIGS. 11A–11E show the partial advancement of the needle 34 with its attached ferrule 103 and suture 105. FIG. 11A is a right perspective view of the drive mechanism of the instrument of FIG. 3 with the thumb slide holder 42 removed, the lever 36a partially retracted, the needle 34 with its ferrule 103 and suture 105 partially advanced and the thumb button 41e fully out. FIG. 11B is a right perspective view of the distal tip 98 of the components of FIG. 11A showing the needle 34 attached to the ferrule 103 and the suture 105 partially advanced. FIG. 11C is a partial cross-sectional view of the distal tip 98 of the components of FIG. 11A showing the needle 34 attached to the ferrule 103 and the suture 105 partially advanced and the ferrule stripper 35 fully back. FIG. 11D is a side view of the proximal components of FIG. 11A showing the lever 36a partially retracted and the thumb button 41e fully out.

FIGS. 11E–11J show the needle 34 fully advanced attached to the ferrule 103 and its suture 105. Note that at this step of the operation, FIG. 11J is provided to show an enlarged view of the distal spring lock 43 and proximal spring lock 44. FIG. 11E is a right perspective view of the drive mechanism of the instrument of FIG. 3 with the thumb slide holder 42 removed and the lever 36a fully retracted and the thumb button 41e fully out. FIG. 11F is a right perspective view of the distal tip 98 of the components of FIG. 11E with the needle 34 fully advanced into the ferrule 103. FIG. 11 G is a partial cross-sectional view of the distal tip 98 of the components of FIG. 11E showing the needle 34 along with its attached ferrule 103 and suture 105 fully advanced into its ferrule compartment 107. FIG. 11H is a side view of the proximal components of FIG.11E showing the lever 36a fully retracted and the thumb button 41e fully out. FIG. 11J is a close-up side view of the lock features of the components of FIG. 11H showing the flat engagement surface 36g of the actuating member 36 raising the proximal spring lock 44 to disengage it from the spring lock engagement slot 41a of the timing tube 41c.

FIGS. 12A–12K illustrate the next two steps to complete advancement of the ferrule stripper 35. FIGS. 12A–12E show the advancing of the push button assembly 41 to partially advance towards stripping the ferrule 103 from the fully advanced needle 34. FIG. 12A is a right partial view of the drive mechanism of the instrument of FIG. 3 with the thumb slide holder 42 removed, the lever 36a fully retracted, the needle 34 with its attached ferrule 103 and suture fully advanced and the thumb button 41e partially advancing the ferrule stripper 35. FIG. 12B is a right perspective view of the distal tip 98 of the components of FIG. 12A showing the needle 34 with its ferrule 103 and suture 105 fully advanced into its ferrule compartment 107 and the ferrule stripper 35 partially advanced. FIG. 12C is a partial cross-sectional view of the distal tip 98 of the components of FIG. 12A showing the needle 34 attached to the ferrule 103 and suture 105 fully advanced and the ferrule stripper 35 partially advanced.

FIG. 12D is a side view of the proximal components of FIG. 12A showing the lever 36a fully retracted and the thumb button 41e and its attached timing tube 41c partially forward. FIG. 12E is a close-up side view of the lock features of the components of FIG. 12D showing the flat engagement surface 36g raising the proximal spring lock 44 out of the spring lock engagement slot 41a and the timing tube 41c partially forward.

FIGS. 12F–12K show the full advancement of both the needle 34 and ferrule stripper 35. FIG. 12F is a right perspective view of the drive mechanism of the instrument of FIG. 3 with the thumb slide holder 42 removed, the lever 36a fully retracted, the needle 34 with its attached ferrule 103 and suture 105 fully advanced, and the thumb button 41e advancing its ferrule stripper 35 fully forward. FIG. 12G is a right perspective view of the distal end of the components of FIG. 12F showing the needle 34 with its ferrule 103 and suture 105 fully advanced and the ferrule stripper 35 fully advanced and engaging the proximal edge of the ferrule 103, as best shown in FIG. 12H. FIG. 12H is a partial cross-sectional view of the distal tip 98 of the components of FIG. 12F showing the needle 34 attached to the ferrule 103 and the suture 105 and the ferrule stripper 35 fully advanced and flexed onto the needle 34 to engage the proximal edge of the ferrule 103. FIG. 12J is the side view of the proximal components of FIG. 12F showing both the lever 36a and the thumb button 41e fully forward. FIG. 12K is a close-up side view of the lock features of FIG. 12J showing the actuating member 36 raising the proximal spring lock 44, allowing the distal spring lock 43 to engage the spring lock engagement slot 41a in the timing tube 41c. Note a relief 36j in the top of the actuating member 36 allows the distal spring lock 43 to travel downward and engage the spring lock engagement slot 41a.

The last three steps, FIGS.13A–13R, illustrate the complete retraction of both the needle 34 and ferrule stripper 35. FIGS. 13A–13E show the lever 36a partially forward to retract the needle 34 to strip the ferrule. 103 by engaging ferrule 103 with the fully advanced ferrule stripper 35. FIG. 13A is a right perspective view of the drive mechanism of the instrument of FIG. 3 with the thumb slide holder 42 removed, the lever 36a partially released, the needle 34 partially retracted, the ferrule stripper 35 engaging the ferrule 103 in its ferrule compartment 107 and the thumb button 41e fully forward.

FIG. 13B is a right perspective view of the distal tip 98 of the components of FIG. 13A showing the needle 34 partially retracted from its ferrule 103 (not visible in this view) and the ferrule stripper 35 fully forward. FIG. 13C is a partial cross-sectional view of the distal tip 98 of the components of FIG. 13A showing the needle 34 partially retracted and the ferrule stripper 35 fully forward engaging the ferrule 103 in its ferrule compartment 107. FIG. 13D is a side view of the proximal components of FIG. 13A showing the lever 36a partially out and the thumb button 41e fully forward. FIG. 13E is a close-up side view of the lock features of FIG. 13D showing the convex engagement surface 36h of the actuating member 36 (FIG. 13D) raising the distal spring lock 43 to disengage the spring lock engagement slot 41a of the timing tube 41c.

FIGS. 13F–13K show both the needle 34 and ferrule stripper 35 partially returning with the ferrule 103 replaced back into its ferrule compartment 107. FIG. 13F is a right perspective view of the drive mechanism of the instrument of FIG. 3 with the thumb slide holder 42 removed, the lever 36a, needle 34, thumb button 41e and ferrule stripper 35 partially back. FIG. 13G is a right perspective view of the distal tip 98 of the components of FIG. 13F with the needle 34 and ferrule stripper 35 partially retracted and the ferrule 103 back into its ferrule compartment 107. FIG. 13H is a partial cross-sectional view of the distal tip 98 of the components of FIG. 13F showing the needle 34 and the ferrule stripper 35 partially back and the ferrule 103 and suture 105 in the ferrule compartment 107. FIG. 13J is a side view of the proximal components of FIG. 13F showing the lever 36a and the thumb button 41e partially back. FIG. 13K is a close-up side view of the lock features of FIG. 13F showing the engaging surfaces 36f–36h of the actuating member 36 not raising the proximal spring lock 44 or the distal spring lock 43 with the spring lock engagement slot 41a released.

FIGS. 13L–13R show the instrument reloaded, ready for use and are identical to FIGS. 9A–9D, respectively, while FIG. 13R highlights re-engagement of the proximal spring lock 44 with the spring lock engagement slot 41a. FIG. 13L is a right perspective view of the drive mechanism of the instrument of FIG. 3 with the thumb slide holder 42 removed, the lever 36a, needle 34, thumb button 41e and ferrule stripper 35 fully back and the ferrule 103 and suture 107 reloaded into the ferrule compartment 107. FIG. 13M is a perspective view of the distal tip 98 of the components of FIG. 13L showing the needle 34 and ferrule stripper 35 fully retracted and the ferrule 103 and suture 107 in the ferrule compartment 107. FIG. 13N is a partial cross-sectional view of the distal tip 98 of the components of FIG. 13L showing the needle 34 and ferrule stripper 35 fully back and the ferrule 103 and suture 107 in the ferrule compartment. FIG. 13P is a side view of the proximal components of FIG. 13L showing the lever 36a and the thumb button 41e fully back. FIG. 13R is a close-up side view of the lock features of FIG. 13L showing the proximal spring lock 44 engaging the spring lock engagement slot 41a of the timing tube 41c.

Now referencing FIGS. 14A–17D, showing the multiple placement of sutures to form a wound closure. FIGS. 14A–14E illustrate the use of this instrument for the placement of the first suture of a wound closure and the readiment of the instrument for subsequent bites. FIG. 14A shows the distal tip 98 of the instrument 16 above a wound closure 110. Note the distal side of the wound closure 110 has cross-hatching for purposes of this illustration. FIG. 14B shows the device 16 with the needle 34 passing through the first bite 124 of the distal side of the wound 110. FIG. 14C shows the needle 34 retracted back with its ferrule 103 and suture 105 pulled through the wound 110. FIG. 14D shows the needle 34 now advanced through to place the ferrule 103 back into its ferrule compartment 107. FIG. 14E shows the needle 34 back after having its ferrule 103 stripped. The instrument is now ready for another bite.

Now referencing FIGS. 15A–15E, the device 16 is again placed into the wound 110 this time with the proximal side of the wound 110 in the instrument's jaw 104. The needle 34 will enter the tissue 120 as shown in FIG. 15A, traverse the tissue 120 and enter the ferrule compartment 107 as shown in FIG. 15B. FIG. 15C illustrates the needle 34, ferrule 103 and suture 107 pulled back leaving suture 105 through the first bite 126 on the proximal side of the wound closure 110. FIG. 15D shows the needle 34 advanced yet again. FIG. 15E shows the ferrule 103 back in its ferrule compartment 107.

FIG. 16A–16D shows the second suture placement on the distal side of the wound 110. FIG. 16A shows the needle 34 traversing the second site 127 on the distal wound 110 aspect. FIG. 16B shows the suture 105 through the second bite 127 on the distal side of the wound 110. FIG. 16C shows the needle 34, ferrule 103 and suture 105 advanced to the ferrule pocket. FIG.16D shows the instrument again ready for the bite.

FIG. 17A–17D show the second bite 128 on the proximal side of the wound closure 110. FIG. 17A shows the needle 34 going through the second site 128 of the proximal side of the wound closure 110. FIG. 17B shows the needle 34, ferrule 103 and suture 105 advanced back into its ferrule compartment 107. FIG.17C shows the instrument with the ferrule 103 reloaded and the needle 34 and ferrule stripper 35 retracted back. FIG.17D illustrates the appearance of the wound closure 110. If the sutures 105 were to be tied at this time, this type of closure is commonly called a figure of eight suture closure. If the process were to continue with further placements of suture 105 running along the distal and proximal aspects of the wound closure, this type of closure is typically be called a running suture wound closure.

Figure 21:
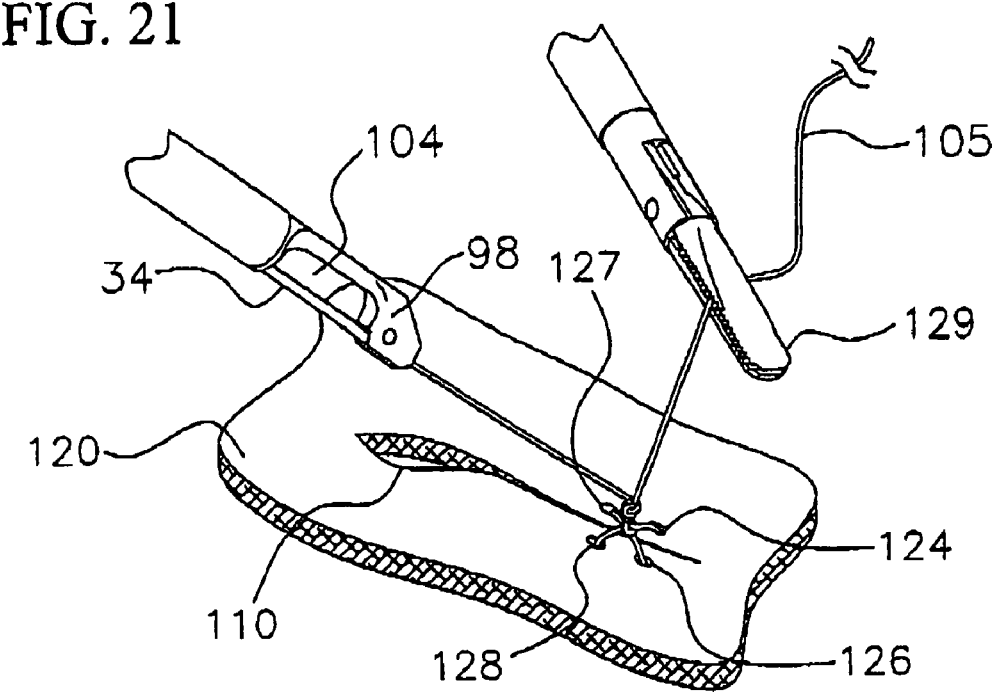
FIG. 21 shows both the suturing instrument of FIG. 1 and a surgical grasper pulling on either ends of the suture to lock the knot in place to secure the wound closure.

Now referencing FIGS. 18A–21, FIG. 18A shows the instrument 16 of this invention with the distal tail of the suture 105 exposed and the distal tip 98 of the instrument 16 ready for knot tying. FIGS. 18A–19B show the first throw of the knot tying process. FIGS. 19C–19F show the second throw of the knot tying process. FIGS. 21 and 22 show the cinching down of the knot. In FIG. 18B, a surgical grasper 129, is used to grab the free end of the suture 105 and to wrap the suture 105 around the jaw 104 of the instrument 16. Note that to construct the unique knot of this invention, which we have named the "Super Surgeon's knot," the first wrapping of suture 105 around the jaw 104 consists of two complete loops wrapped around the jaw 104. FIG. 18C shows the advancement of the needle 34, ferrule 103 and suture 105 back into its ferrule compartment 107, best shown in FIG. 18A, after the double wrap has been placed around the jaw 104 of the instrument 16. FIG. 18D shows the now stripped ferrule 103 in its ferrule compartment 107. FIG. 18E shows the knot forming double loops being slid down towards the wound closure site 110. FIG. 19A shows the grasper 129 further cinching the knot down to the wound closure site 110. FIG. 19B shows the suture 105 now fully retracted back on its needle 34 to further expose the jaw 104 of the knot tying instrument 16. FIG. 19C shows a second wrapping of a single loop placed around the distal tip 98 of the instrument 16 to secure the knot. FIG. 19D shows the needle 34 again advanced to replace the ferrule 103 in its ferrule compartment 107 along with the suture 105. FIG. 19E shows the ferrule 103 in its ferrule compartment 107 with the needle 34 and ferrule stripper 35 now back. FIG. 19F shows the second throw, a single loop throw, of the Super Surgeon's knot being slid over the ferrule 103 and suture 105 down towards the wound closure 110. FIG. 20D illustrates that by pulling on the surgical grasper 129 on the free end of the suture 105, the suture loops are further slid towards and down onto the wound closure 110 to begin to pull (also called approximate or appose) the edges of the wound 110 together, but not fully locking the knot in place. FIG. 21 shows by pulling on the surgical grasper 129 holding the free end of the suture 105, and now by simultaneously pulling on instrument 16 holding the ferrule 103 end of the suture 105, both ends of the suture 105 are drawn tight, thereby locking the Super Surgeon's knot in place. The distinct advantage of the Super Surgeon's knot is that it permits the user to place the knot above the wound closure and appropriately appose the wound edge by pulling only on the free end of the suture, and then, once the correct tissue apposition is achieved, the user can pull on the ferrule end of the suture to lock the knot down. Locking down the Super Surgeon's knot alone provides adequate holding force, at least temporarily, to hold together many types of wound closures. For example, a Super Surgeon's knot made with 2-0 STRONGSORB® suture by LSI SOLUTIONS, Inc., achieves an average tissue holding strengths of approximately 0.5 kg knot holding force to temporarily secure and tissue edges together. Subsequent throws on top of the Super Surgeon's knot will add additional knot holding force up to the native strength of the suture (e.g., with 2-0 STRONG-SORB®, up to 5 to 6 kg tensile pull). No other knot is known (to the inventors) that can be constructed under such surgically relevant conditions and provides excellent tissue holding force immediately when the first throws are drawn together by pulling on both ends of the suture.

Figure 22A:
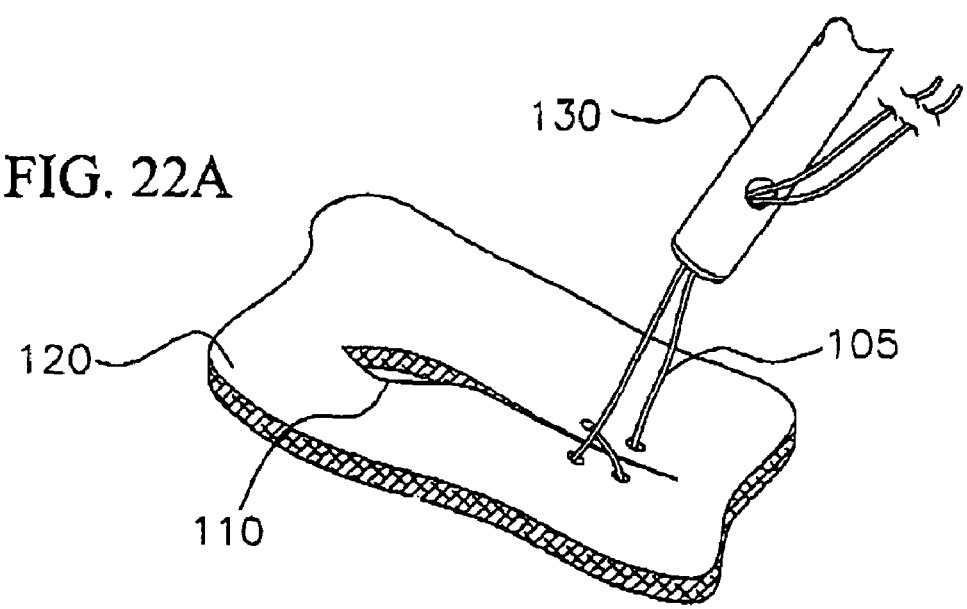
FIGS. 22A–22C show an alternate method of securing the ends of the suture used in the suturing procedure illustrated in FIGS. 14A–17D by crimping a sleeve member over the ends of the suture.
Figure 22B:
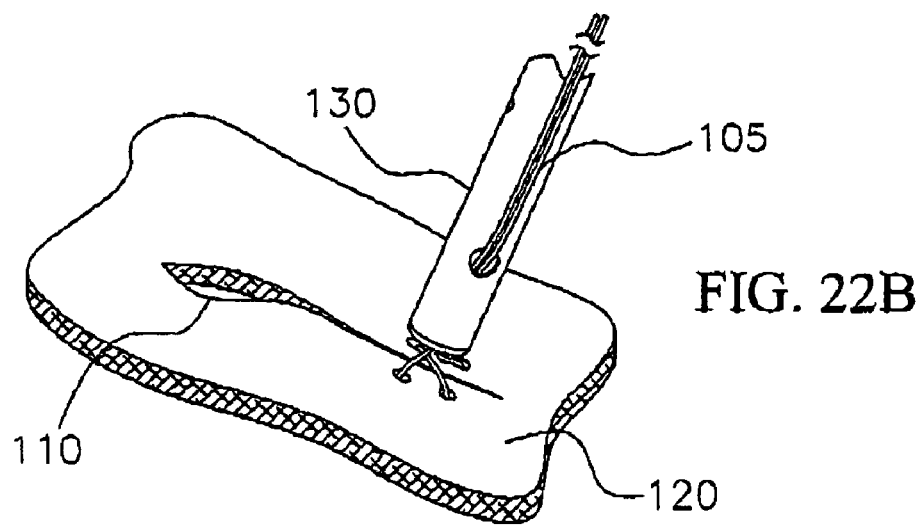
Figure 22C:
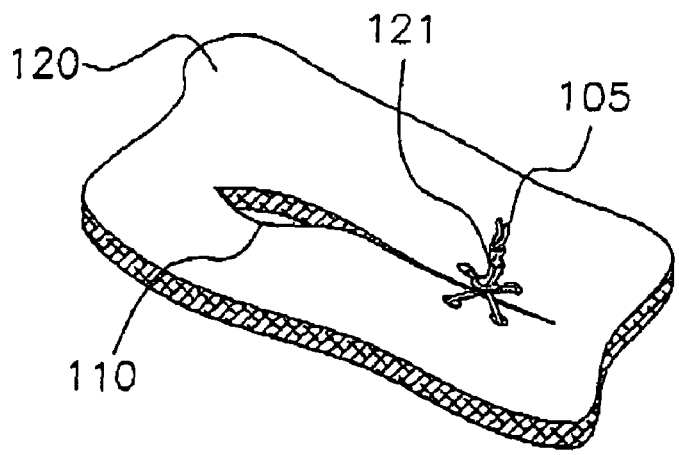

FIGS. 22A–22C illustrate an alternate method of securing the free ends of the suture 105 left by the instrument 16, used to close the wound 110 in the tissue 120. FIG. 22A represents an instrument 130, which crimps a sleeve member 121 to secure suture 105 together and is commercially available as a Ti-KNOT® TK·5®. Device manufactured by LSI SOLUTIONS, Inc., under at least the following patents U.S. Pat. Nos. 5,520,702; 5,643,289 and 5,669,917. The free ends of the suture 105 are passed through the instrument 130 and the instrument 130 is passed closer to the wound closure 110. FIG. 22B illustrates the instrument 130 being applied directly to the wound closure 110 and both free ends of the suture 105 drawn tight, removing any slack and drawing the opposing sides of the wound closure 110 closer together. FIG. 22C shows the sleeve member 121 crimped around the suture 105 at the wound closure 110. Note that the suture 105 has been trimmed.

After using instrument 16 to place suture 105 for running a wound closure 110, one or both ends of the suture 105 may remain unsecured. These free ends of the suture 105 can be attached to pledgets or bolsters 122a and 122b to prevent their ability to be pulled into or away from the wound site 110. A pledget is typically a pliable, non-reactive piece of material, such as polyester mesh, Gortex®, or the like, that is often used in conjunction with sutures or staples to augment wound closures. In this invention, a bolster 122a is attached (e.g., by tying or sewing) to one end of an additional segment of suture 123a. By placing the free end of this bolstered suture 123a, along with one free end of the suture 105, the bolster 122a and its attached suture 123a can be passed down using suture 105 as a guide. Bolster 122a, suture 123a and one end of suture 105 can be secured at one end of the wound site 110 with a sleeve member 121. The bolster 122a can hold this end of the running suture 105 from being pulled into the wound 110. By repeating a similar bolstered suture 123b placement at the opposite end of the wound 110, the second bolster 122b and its suture 123b can hold the second suture 105 end from being pulled into the wound 110. Bolsters 122a and 122b secured at each end of the wound 110, prevent the suture 105 from being pulled out of the wound 110 from either direction.

FIGS. 24A–24C illustrate a second preferred embodiment of this invention. The main difference between this embodiment and the first preferred embodiment, is that instead of stripping the ferrule 103 with the ferrule stripper 35 traversing the gap and engaging the ferrule 103, the member that directly contacts the ferrule 103 for ferrule stripping is incorporated in the distal tip 98. The thumb button 41e drive mechanism for this embodiment can be the same as in the first preferred embodiment. FIG. 24A shows a perspective of the distal jaw, which looks similar to the first embodiment, except instead of a slope to direct the stripper wedge 131 towards the ferrule, the stripper wedge 131 enters a chamber 141 and subsequently wedges member 133 against ferrule 103 to permit removal of the needle 34. FIG. 24B shows needle 34 engaging ferrule 103 in ferrule compartment 107 with the stripper wedge 131 traveling toward chamber 141. FIG. 24C shows the ferrule 103 held in its ferrule compartment 107 by stripper wedge 131 forcing over member 133. Needle 34 can now be extracted from ferrule 103. Stripper wedge 131 can be subsequently withdrawn leaving the ferrule 103 in it reloaded position.

FIGS. 25A–25C illustrate a third preferred embodiment of this invention. In this embodiment, unlike the prior two, the ferrule stripping element does not traverse the gap in the distal tip 98. Rather, in this embodiment, the stripper wedge 131, which can be a semi-flexible material, such as memory metal, Nitinol, or the like, passes through a channel in the bridge that traverses behind the gap in the jaw. This ferrule stripping embodiment can also be advanced towards the ferrule using a mechanism similar to the already described thumb slide mechanism 41 (FIG. 3). FIG. 25A shows needle 34 after being retracted back and stripped off ferrule 103 held in its ferrule compartment 107 by the flexible integrated stripper 135. FIG. 25B is a partial sectional view of needle 34 engaging ferrule 103 in its ferrule compartment 107. The flexible integrated stripper 135 is shown retracted into the bridge channel 134 to permit the needle 34 to pull the ferrule 103 out of its ferrule compartment 107. FIG. 25C illustrates a partially retracted needle after its ferrule 103 is stripped by the flexible integrated stripper 135.

FIGS. 26–30J describe a fourth preferred embodiment of this invention. Unlike the previous three embodiments, this fourth version does not require an additional manual mechanism, like the thumb slide mechanism, to enable ferrule stripping. Instead of pushing a button to activate a stripper, this instrument is more automated to enable stripping the ferrule 103 imply squeezing the lever 36a a second time.

Figure 26:
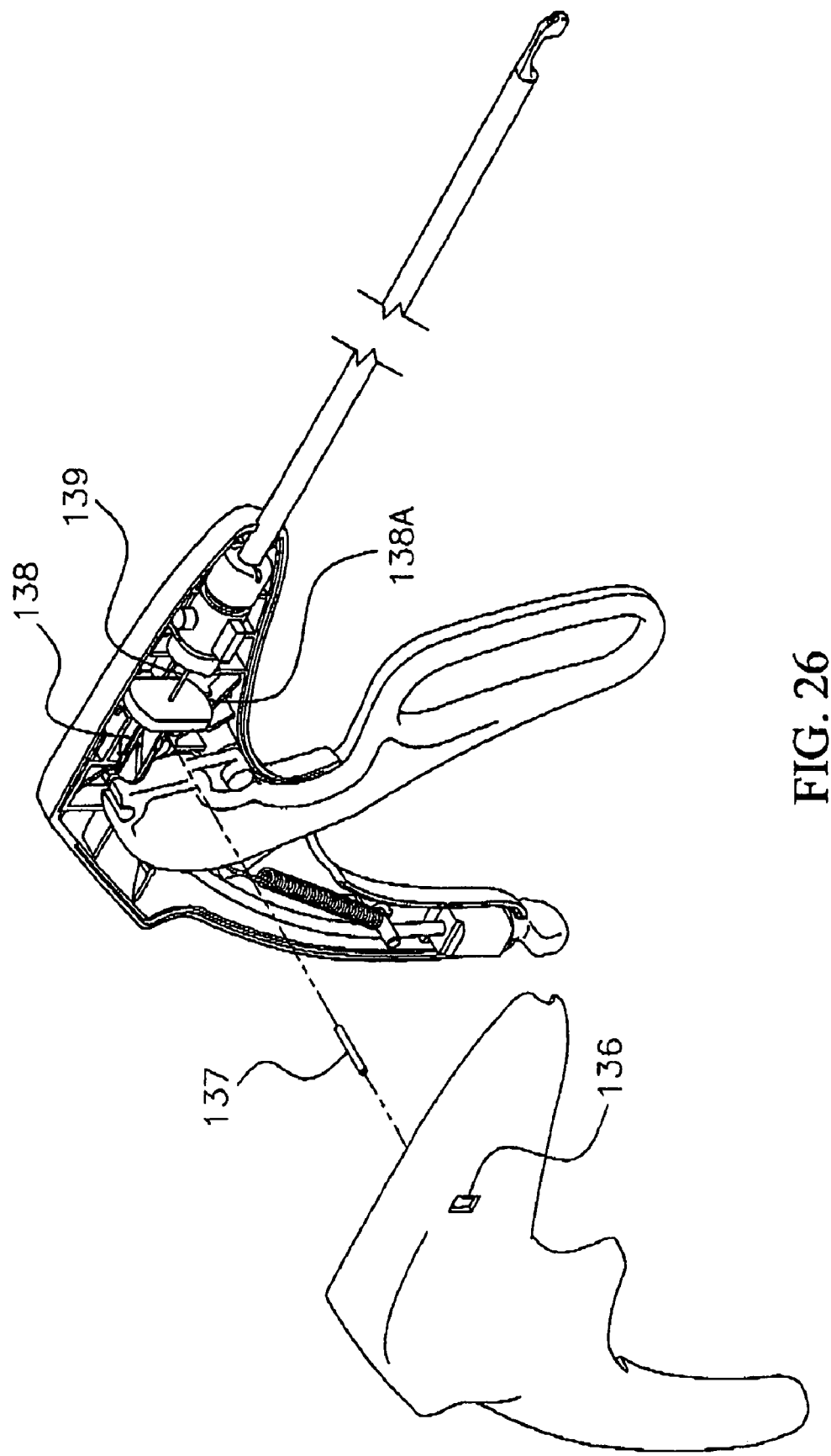
FIG. 26 is a partially exploded isometric view of the fourth preferred embodiment of the tissue suturing instrument of FIG. 1 in which a cam and follower mechanism and faceted needle are utilized to allow for automatic ferrule pick-up and release.

FIG. 26 shows this instrument in a perspective view illustrating window 136 in the right handle half; a comparable window (not shown) is located in the opposite location on the left handle half. These windows permit an instrument user to view from either handle an asymmetric rotating disc 138a that indicates whether the cam needle 139 is in the stripper or non-stripper orientation. Also, note rod 137 mounts into the right handle half to engage the slots in the rotating cam 138. When lever 36a rotates back, cam 138 drives forward, lifts towards the mid stroke, then lowers and rotates about rod 137, as seen in FIGS. 27A–27C.

FIG. 27A shows the rod 137 engaging the distal slot in cam 138. The rotating indicator disc 138a is vertically oriented indicating a non-faceted edge of the cam needle 139 faces the ferrule latch 140 (FIG. 27A; also see FIGS. 28–31J). Release of the lever 36a permits the cam needle 139 and its rotational cam 138 to travel back and elevates slightly at mid stroke, where rod 137 enters an obliquely oriented slot, to begin rotating the rotational cam 138 and its attached cam needle 139 (FIG. 27E). By completion of the lever 36a, the full rotation of the rotational cam 138 (FIG. 27A), the needle facet 139b (FIG. 27F) is now oriented towards the ferrule latch 140, which permits ferrule stripping.

Figure 28:
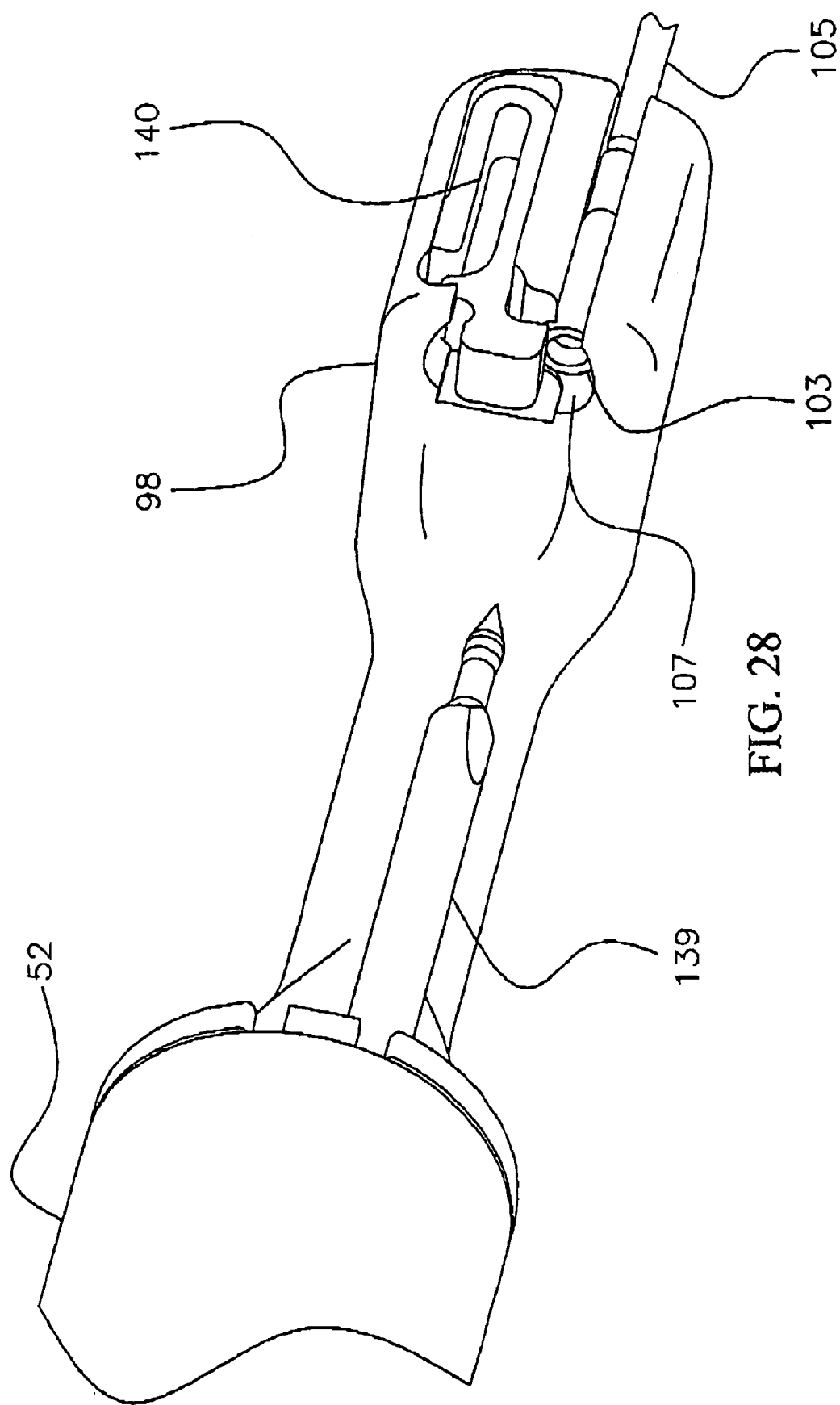
FIG. 28 is a close-up perspective view of the distal tip of the fourth preferred embodiment of the tissue suturing instrument of FIG. 1 showing a partially advanced faceted needle, the ferrule in its ferrule compartment and a ferrule latch adjacent to the ferrule pocket.

FIG. 28 shows the partially retracted cam needle 139 having its ferrule 103 held by ferrule latch 140. Note this illustration shows a pocket 142 recessed in the distal tip 98 for holding the ferrule latch 140.

FIG. 29A shows cam needle 139 oriented with a non-faceted shoulder 139c engaging and lifting the ferrule engaging surface 140g of the ferrule latch 140. The ferrule 103 is not held by the ferrule latch 140, because the ferrule 103 latch 140 is compressed by the non-faceted shoulder 139c pushing against timing surface 140b. The ferrule 103 is able to be pulled from its ferrule compartment 107 by cam needle 139. FIG. 29B shows the distal end of the fourth preferred embodiment with cam needle 139 retracting back through the gap and the ferrule latch 140 engaging into the proximal edge of ferrule 103. FIG. 29B highlights cam needle 139 oriented to have a facet 139b towards the ferrule latch 140, to not engage timing surface 140b so that the ferrule engagement surface 140g contacts the proximal edge of ferrule 103. Surfaces 140f and 140e provide contacts to help maintain latch placement in its pocket 142.

Figure 30D:
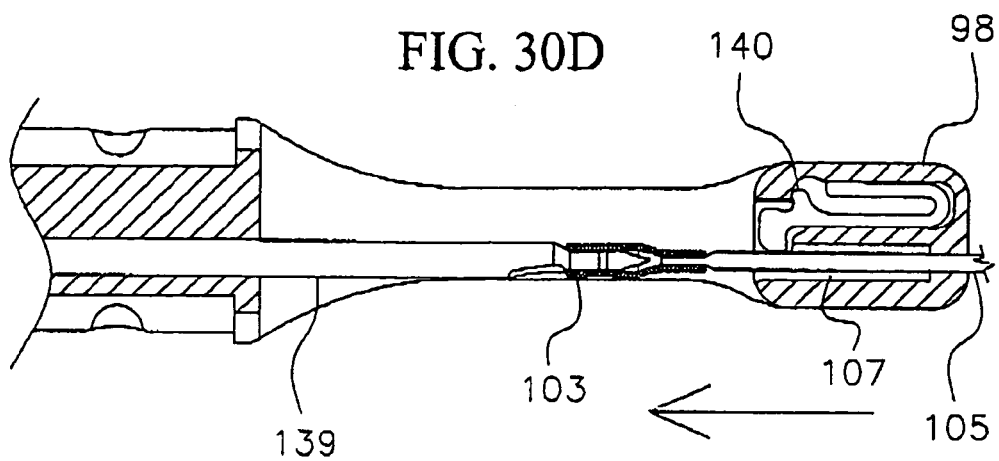
FIG. 30D is a partial cross-sectional view of the distal tip of the fourth preferred embodiment of the tissue suturing instrument of FIG. 1 showing the faceted needle retracting with its attached ferrule and suture and the ferrule latch returning to its normal state.
Figure 30E:
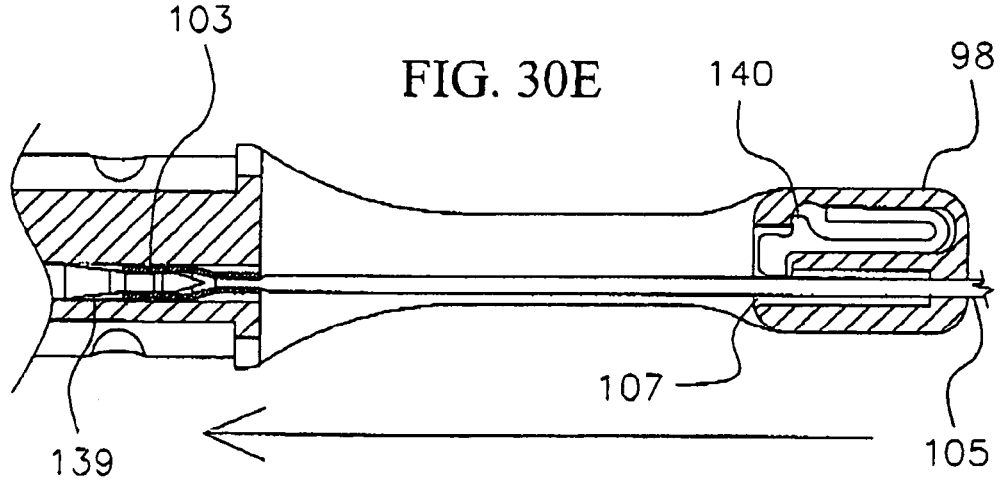
FIG. 30E is a partial cross-sectional view of the distal tip of the fourth preferred embodiment of the tissue suturing instrument of FIG. 1 showing the faceted needle fully retracted with its attached ferrule and suture.
Figure 30F:
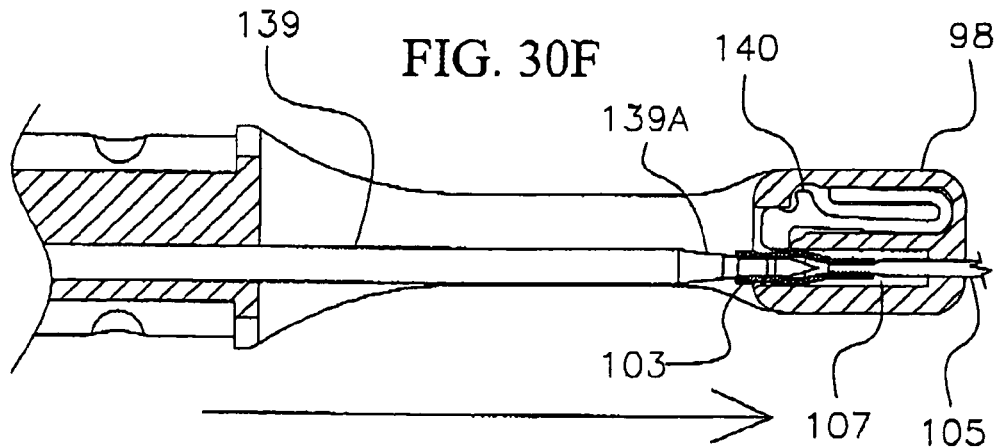
FIG. 30F is a partial cross-sectional view of the distal tip of the fourth preferred embodiment of the tissue suturing instrument of FIG. 1 showing the faceted needle extending and returning the ferrule and its suture to the ferrule compartment.
Figure 30G:
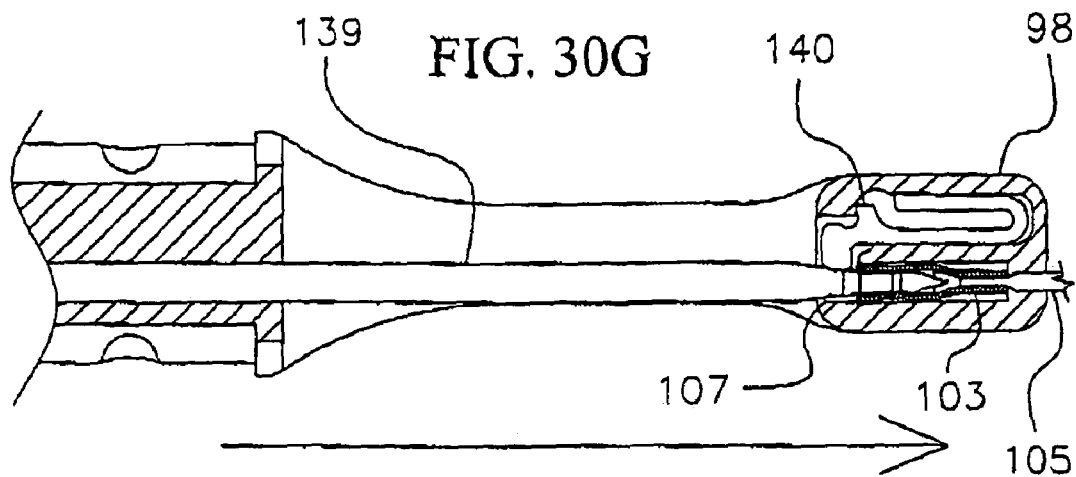
FIG. 30G is a partial cross-sectional view of the distal tip of the fourth preferred embodiment of the tissue suturing instrument of FIG. 1 showing the faceted needle fully extended, the ferrule and its suture returned to the ferrule compartment and the ferrule latch engaged with the proximal face of the ferrule.
Figure 30H:
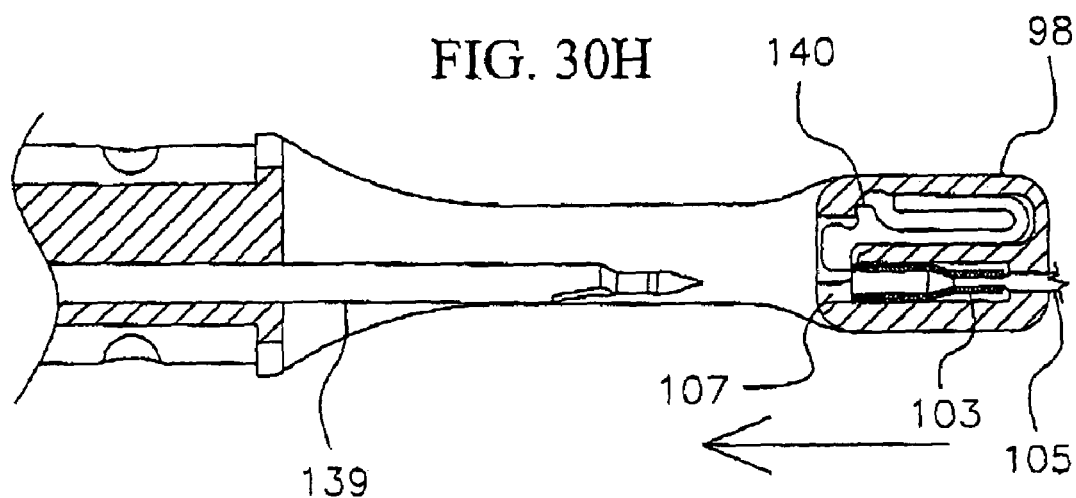
FIG. 30H is a partial cross-sectional view of the distal tip of the fourth preferred embodiment of the tissue suturing instrument of FIG. 1 showing the faceted needle retracting and the ferrule latch retaining the ferrule in its ferrule compartment.
Figure 30J:
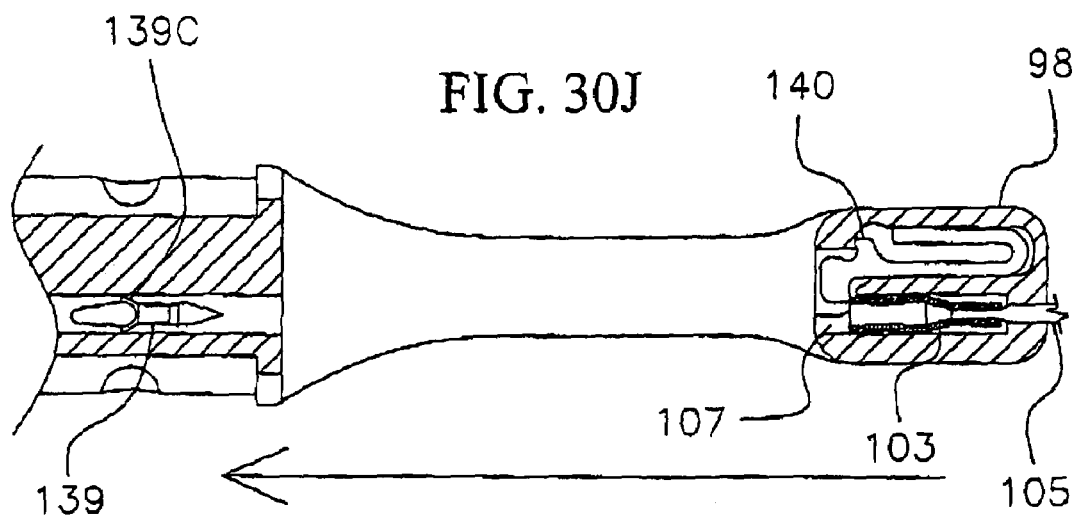
FIG. 30J is a partial cross-sectional view of the distal tip of the fourth preferred embodiment of the tissue suturing instrument of FIG. 1 showing the faceted needle fully retracted and awaiting the next cycle of firing of the instrument.

FIGS. 30A–30J show one complete cycle of the cam needle 139 traversing the jaw 104, picking up a ferrule 103, the ferrule 103 being returned to its ferrule compartment 107 and the ferrule 103 being stripped by the ferrule latch 140. This cycle reloads the ferrule 103 for another stitch placement. FIG. 30 shows the retracted cam needle 139 oriented with a non-faceted shoulder 139c facing the ferrule latch 140, which secures the ferrule 103 with its suture 105 in its ferrule compartment 107 in the distal tip 98. FIG. 30B shows cam needle 139 fully advanced into ferrule 103, with its non-faceted shoulder 139c compressing ferrule latch 140. FIG. 30C shows cam needle 139 pulling ferrule 107 and suture 105 back beyond the compressed ferrule latch 140. At approximately the midpoint of the cam needle 139 retraction, cam needle 139 begins its rotation with ferrule 103 and suture 105 rotating with cam needle 139. FIG. 30E shows cam needle 139 along with its ferrule 103 and suture 105 fully retracted back with its 900 rotation completed. FIG. 30F shows cam needle 139, ferrule 103 and suture 105 advancing back into ferrule compartment 107. A faceted shoulder 139a of cam needle 139 now faces the ferrule latch 140. FIG. 30G shows the cam needle 139, ferrule 103 and suture 105 fully placed back into its ferrule compartment 107. The faceted shoulder 139a of cam needle 139 does not cause ferrule latch 140 to compress up or deflect away from the proximal edge of ferrule 103. FIG. 30H shows the retraction of ferrule 103 stopped by ferrule latch 140, stripping ferrule 103 from its partially retracted cam needle 139. FIG. 30J shows the cam needle 139 now fully retracted back and rotated back 180° so that the opposite side of the non-faceted shoulder 139c is oriented towards the ferrule latch. The ferrule 103 is reloaded back into its ferrule compartment 107 and cam needle 139 is ready to advance through more tissue 120, picking up ferrule 103 and pulling it along with its suture 105 back through another bite of tissue 120.

The invention claimed is:

1. A surgical suturing instrument comprising:
   (a) an elongated shaft;
   (b) a tissue engaging gap formed proximal to an end of the shaft;
   (c) a needle reciprocally movable across the gap from a proximal end of the gap to a distal end of the gap;
   (d) the needle having a ferrule engaging tip
   (e) a ferrule receiving aperture at a distal end of the gap an element cooperating with the aperture sequentially holding and releasing the ferrule so that in a first mode, the needle engages the ferrule and draws a suture across the gap, and in a second mode, the ferrule is retained in the aperture and the needle separates from the ferrule and is retracted across the gap leaving the ferrule in the aperture.

2. The surgical suturing instrument of claim 1 comprising a stripper engaging the ferrule in the second mode and retaining the ferrule in the aperture.

3. The surgical suturing instrument of claim 2 in which the stripper extends from the proximal end of the gap across the gap to the distal end of the gap.

4. The surgical suturing instrument of claim 3 comprising a camming surface adjacent the ferrule receiving aperture guiding an end of the stripper into engagement with the ferrule for holding the ferrule in the aperture and allowing the needle to be withdrawn from the ferrule.

5. The surgical suturing instrument of claim 4 in which the camming surface comprises an alignment ramp angled towards a proximal end of the ferrule.

6. The surgical suturing instrument of claim 1 comprising: a handle.

7. The surgical suturing instrument of claim 6 comprising a needle actuator on the handle for selectively advancing and retracting the needle across the gap.

8. The surgical suturing instrument of claim 7 comprising a spring biasing the needle actuator to a needle retracted position.

9. The surgical suturing instrument of claim 8 in which the needle actuator is pivotally mounted to the handle.

10. The surgical suturing instrument of claim 7 comprising a stripper actuator on the handle for selectively advancing and retracting the stripper across the gap.

11. The surgical suturing instrument of claim 10 in which the stripper actuator comprises a push button.

12. The surgical suturing instrument of claim 11 in which the push button comprises a thumb operated button.

13. The surgical suturing instrument of claim 12 comprising a spring biasing the stripper actuator to a retracted position.

14. The surgical suturing instrument of claim 10 in which the stripper actuator is coupled to the needle actuator.

15. The surgical suturing instrument of claim 14 comprising a spring lock for locking the stripper in an extended position engaging the ferrule.

16. The surgical suturing instrument of claim 15 in which the needle actuator releases the spring lock after the needle has been withdrawn from the ferrule.

17. The surgical suturing instrument of claim 1 in which the needle has an unsymmetrical cross section.

18. The surgical suturing instrument of claim 17 comprising a means for rotating the needle between a first rotational position in the first mode and a second rotational position in the second mode.

19. The surgical suturing instrument of claim 18 comprising a ferrule latch activated by the needle for selectively retaining the ferrule in the gap.

20. The surgical suturing instrument of claim 1 comprising a clamp for retaining the ferrule in the ferrule receiving aperture in the second mode and releasing the ferrule in the first mode.

21. The surgical suturing instrument of claim 20 comprising a clamp activator reciprocally movable to engage the clamp to cause it to retain the ferrule in the ferrule receiving aperture in the second mode and release the ferrule in the first mode.

22. A surgical suturing instrument for placing multiple suture loops comprising:
   (a) an elongated shaft;
   (b) a reciprocating suture pickup member mounted on said shaft;
   (c) a suture holder engaged by said reciprocating suture pick up member the suture holder having an element sequentially coupling a suture to the pick up member for drawing the suture through a first tissue section and releasing the suture from the pick up member for repeated coupling and drawing the suture through a second tissue section spaced from the first tissue section.

23. The surgical suturing instrument of claim 22 comprising a stripper selectively engaging a suture holding member for releasing the suture from the pickup member.

24. The surgical suturing instrument of claim 23 in which the stripper comprises a reciprocating member selectively movable into a position for stripping the suture from the pickup member.

25. The surgical suturing instrument of claim 24 in which the stripper extends from the proximal end of the gap across the gap to the distal end of the gap.

26. The surgical suturing instrument of claim 24 comprising a camming surface adjacent the ferrule receiving aperture guiding an end of the stripper into engagement with the ferrule for holding the ferrule in the aperture and allowing the needle to be withdrawn from the ferrule.

27. The surgical suturing instrument of claim 24 in which the camming surface comprises an alignment ramp angled towards a proximal end of the ferrule.

28. The surgical suturing instrument of claim 26 comprising a needle actuator on the handle for selectively advancing and retracting the needle across the gap.

29. The surgical suturing instrument of claim 28 comprising a spring biasing the needle actuator to a needle retracted position.

30. The surgical suturing instrument of claim 29 comprising a stripper actuator on the handle for selectively advancing and retracting the stripper across the gap.

31. The surgical suturing instrument of claim 30 in which the stripper actuator is coupled to the needle actuator.

32. A surgical suturing instrument comprising:
(a) a reciprocating tissue penetrating member;
(b) a suture holder;
(c) means for alternately coupling the reciprocating tissue penetrating member to the suture holder for drawing a length of suture through a tissue section and releasing the reciprocating tissue penetrating member from the suture holder.

33. The surgical suturing instrument of claim 32 comprising a squeezable handle coupled to the reciprocating tissue penetrating member for reciprocating the tissue penetrating member.

34. The surgical suturing instrument of claim 32 comprising a stripper for holding the suture holder and allowing the reciprocating tissue penetrating member to separate therefrom.

35. The surgical suturing instrument of claim 34 in which the stripper is coupled to the squeezable handle.

36. The surgical suturing instrument of claim 34 comprising a plunger coupled to the stripper.

37. A method of closing a wound with a stitch at a remote surgical site comprising:
(a) disposing a suture on one side of a section of tissue proximal to the wound;
(b) passing a needle through the section of tissue proximal to the wound;
(c) capturing the suture with the needle;
(d) drawing the suture through the section of tissue;
(e) releasing the suture from the needle; and
(f) repeating steps b–e without drawing the suture from the remote surgical site.

38. The method of claim 37 in which the suture has a ferrule attached to an end of the suture, and in which the step of capturing the suture with a needle comprises engaging the suture with an end of the needle.

39. The method of claim 37 comprising repeating steps b–e to form a figure 8 knot.

40. The method of claim 37 comprising repeating steps b–e to form a running stitch.

41. The method of claim 39 comprising securing the ends of the suture together to form the knot.

42. The method of claim 40 comprising independently securing each end of the suture forming the running stitch.

43. The method of claim 42 in which securing each end of the suture comprises passing at least one end through a bolster and securing the end with the bolster disposed between the end and the wound.

44. The method of claim 37 further comprising securing a suture at a wound site comprising passing the end of the suture through a bolster and securing the suture with the bolster disposed between the end of the suture and the wound.

45. The method of claim 44 comprising securing a section of a second suture to the bolster, and securing the suture and the second suture together at a location on the opposite side of the bolster from the wound.

* * * * *